(12) United States Patent
Gerlach et al.

(10) Patent No.: US 8,791,118 B2
(45) Date of Patent: Jul. 29, 2014

(54) PYRIDOPYRAZINES AS HIGHLY SELECTIVE RAS-RAF-MEK-ERK SIGNAL TRANSDUCTION PATHWAY INHIBITORS

(75) Inventors: Matthias Gerlach, Brachttal (DE); Irene Seipelt, Offenbach (DE); Lars Blumenstein, Frankfurt am Main (DE); Gilbert Mueller, Frankfurt am Main (DE); Eckhard Guenther, Maintal (DE); Tilmann Schuster, Grossostheim (DE); Michael Teifel, Weiterstadt (DE)

(73) Assignee: Aeterna Zentaris GmbH, Frankfurt am Main (DE)

( * ) Notice: Subject to any disclaimer, the term of this patent is extended or adjusted under 35 U.S.C. 154(b) by 48 days.

(21) Appl. No.: 13/439,150

(22) Filed: Apr. 4, 2012

(65) Prior Publication Data
US 2012/0258080 A1 Oct. 11, 2012

Related U.S. Application Data

(60) Provisional application No. 61/472,245, filed on Apr. 6, 2011.

(30) Foreign Application Priority Data

Apr. 6, 2011 (EP) .................................. 11161248

(51) Int. Cl.
*A61K 31/4985* (2006.01)
*C07D 487/04* (2006.01)

(52) U.S. Cl.
USPC ........... 514/249; 544/117; 544/350; 544/359; 546/199; 546/268.1; 548/304.4; 548/364.7; 548/518; 548/560; 549/356; 549/429

(58) Field of Classification Search
CPC ........................ A61K 31/4985; C07D 487/04

USPC ........... 514/249; 544/117, 350, 359; 546/199, 546/268.1; 548/304.4, 364.7, 518, 560; 549/356, 429
See application file for complete search history.

(56) References Cited

U.S. PATENT DOCUMENTS

| 7,276,507 B2 | 10/2007 | Claus et al. |
| 7,323,468 B2 | 1/2008 | Claus et al. |
| 2007/0123494 A1 | 5/2007 | Seipelt et al. |
| 2007/0149484 A1 | 6/2007 | Claus et al. |
| 2007/0275972 A1 | 11/2007 | Claus et al. |
| 2008/0113991 A1 | 5/2008 | Claus et al. |
| 2009/0275534 A1 | 11/2009 | Gerlach et al. |

OTHER PUBLICATIONS

U.S. Appl. No. 13/439,107, filed Apr. 4, 2012, Gerlach et al.
U.S. Appl. No. 13/455,187, filed Apr. 25, 2012, Gerlach et al.
U.S. Appl. No. 13/455,435, filed Apr. 25, 2012, Gerlach et al.
U.S. Appl. No. 13/770,470, filed Feb. 19, 2013, Claus et al.
U.S. Appl. No. 13/542,101, filed Jul. 5, 2012, Gerlach et al.
U.S. Appl. No. 13/523,968, filed Jun. 15, 2012, Claus et al.

*Primary Examiner* — Douglas M Willis
(74) *Attorney, Agent, or Firm* — Oblon, Spivak, McClelland, Maier & Neustadt, L.L.P.

(57) ABSTRACT

The invention provides new pyridopyrazine compounds according to formula (I)

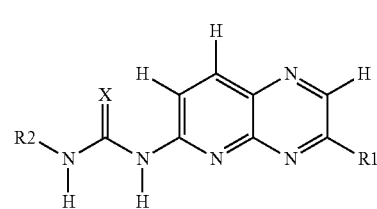

which are highly selective as Ras-Raf-Mek-Erk signal transduction pathway inhibitors and in particular are highly selective Erk inhibitors.

10 Claims, No Drawings

PYRIDOPYRAZINES AS HIGHLY SELECTIVE RAS-RAF-MEK-ERK SIGNAL TRANSDUCTION PATHWAY INHIBITORS

FIELD OF THE INVENTION

The present invention relates to pyridopyrazine derivatives with new biological action and their use for the treatment of physiological and/or pathophysiological states mediated and/or modulated by signal transduction pathways in mammals and in particular in humans.

BACKGROUND OF THE INVENTION

The signal transduction cascade ras-Raf-Mek-Erk plays a central role in cell growth, cell proliferation, apoptosis, adhesion, migration and glucose metabolism. Consequently, the fundamental involvement in the pathogenesis of diseases such as cancer, neurodegeneration and inflammatory diseases is proven for the ras-Raf-Mek-Erk signal pathway. The individual components of these signal cascades are therefore important therapeutic points of attack for intervention in various disease processes (Weinstein-Oppenheimer C. R. et al. 2000, Chang F. et al. 2003, Katso R. et al 2001 and Lu Y. et al 2003).

The molecular and biochemical properties of the ras-Raf-Mek-Erk signal pathways is first described separately hereinafter.

A plurality of growth factors, cytokines and oncogenes transduce their growth-promoting signals via the activation of G-protein coupled ras which leads to the activation of serine threonine kinase Raf and to the activation of mitogen-activated protein kinase kinase 1 and 2 (MAPKK1/2 or Mek1/2) and results in the phosphorylation and activation of MAPK 1 and 2—also known as extracellular signal regulated kinase (Erk1 and 2). Compared to other signal pathways, the ras-Raf-Mek-Erk signal pathway combines a large number of proto-oncogenes, including ligands, tyrosine kinase receptors, G-proteins, kinases and nuclear transcription factors. Tyrosine kinases such as, for example, EGFR (Mendelsohn J. et al., 2000) frequently mediate constitutively active signals to the downstream ras-Raf-Mek-Erk signal pathway in tumour events caused by overexpression and mutation. Ras mutations are mutated in 30% of all human tumours (Khleif S, N. et al., 1999, Marshall C., 1999), the highest incidence of 90% being found in pancreatic carcinomas (Friess H. et al., 1996, Sirivatanauksorn V. et al., 1998). For c-Raf a deregulated expression and/or activation has been described in various tumours (Hoshino R. et al., 1999, McPhillips F. et al., 2001). B-Raf point mutants were detected in 66% of all human malignant melanomas, 14% of all ovarian carcimomas and 12% of all carcinomas of the colon (Davies H. et al., 2002). It is therefore not surprising that Erk1/2 is primarily involved in many cellular processes such as cell growth, cell profileration and cell differentiation (Lewis T. S. et al., 1998, Chang F. et al., 2003).

In addition, the members of the Raf kinases also have Mek-Erk-independent anti-apoptotic functions whose molecular steps have not yet been fully described. Ask1, Bcl-2, Akt and Bag1 have been described as possible interaction partners for the Mek-Erk-independent Raf activity (Chen J et al., 2001, Troppmaier J. et al., 2003, Rapp U. R. et al., 2004, Gotz R. et al., 2005). It is assumed nowadays that both Mek-Erk-dependent and Mek-Erk-independent signal transduction mechanisms control the activation of the upstream ras and Raf stimuli.

Various inhibitors of individual components of the ras-Raf-Mek-Erk signal pathway have already been published and patented.

The present state of development in the field of kinase inhibitors, in particular of the ras-Raf-Mek-Erk and PI3K-Akt pathway, is described in the reviews of H. T. Arkenau et al, 2011, M. S. Chapman & J. N. Miner, 2011 and P. Liu et al, 2009. These publications contain comprehensive listings of the published low-molecular ras-Raf-Mek-Erk- and PI3K inhibitors.

The kinase inhibitor Sorafenib (Bay 43-9006; WO 99/32111, WO 03/068223) which was approved in, 2006 shows a relatively non-specific inhibition pattern of serine/threonine and of tyrosine kinases such as Raf, VEGFR2/3, Flt-3, PDGFR, c-Kit and other kinases. Great importance is attached to this inhibitor in angiogenesis-induced advanced tumour diseases (e.g. in renal cell carcinoma) and also in melanomas having a high B-Raf mutation rate. No inhibition of the kinases in the PI3K-Akt signal pathway has been described for Bay 43-9006. Other Raf-specific inhibitors like PLX-4032 and GSK2118436 (Arkenau H. T. et al, 2011) are currently under clinical evaluation.

Several Mek1/2 inhibitors (AZD-6244, XL-518, GSK1120212 and others) currently undergo clinical testing (reviewed by M S Chapman & J N Miner, 2011). However, no interaction with Erk1 or Erk2 nor any PI3K-Akt signal pathway inhibiting function or its simultaneous modulation has yet been disclosed for these Mek inhibitors.

Patent specification WO 2009/077766 describes pyrido[2,3-b]pyrazines as RAF inhibitors.

In addition, the patent specifications WO 2008/040820, WO 2008/009908 and WO 2005/123733 describe pyrido[2,3-b]pyrazines as agrochemical fungicides and herbicides, respectively.

The Korean invention KR 2008004646 relates to 2-alkenyloxy-3-ethynylpyrido[2,3-b]pyrazine derivatives and their pharmaceutically salts which with inhibit the expression of hypoxia-inducible transcriptional factor 1 (HIF-1) gene.

Patent specifications WO 04/104002 and WO 04/104003 describe pyrido[2,3-b]pyrazines, which can be substituted in the 6- or 7-position with urea, thiourea, amidine or guanidine groups. These compounds possess properties as inhibitors or modulators of kinases, in particular of tyrosine and serine/threonine kinases, and a use as a medicament is specified. However, no use of these compounds as modulators of lipid kinases, alone or in combination with tyrosine and serine/threonine kinases has been described.

In addition, patent specification WO 99/17759 describes pyrido[2,3-b]pyrazines which, among other things, carry alkyl-, aryl- and heteroaryl-substituted carbamates in the 6-position. These compounds are to be used to modulate serine threonine protein kinases.

Patent specification WO 05/007099 describes, among other things, urea-substituted pyrido[2,3-b]pyrazines as inhibitors of the serine/threonine kinase PKB. A use in the treatment of cancer diseases is specified for these compounds. However, no specific examples of urea-substituted pyridopyrazines with these biological properties are given.

Further examples of pyrido[2,3-b]pyrazines substituted with urea in the 6- and 7-position are given in patent specification WO 05/056547. The compounds in this patent specification are described as inhibitors of protein kinases, in particular GSK-3, Syk and JAK-3. A use in the treatment of proliferative diseases is given for these compounds among other things. No use of these compounds as modulators of lipid kinases, alone or in combination with serine/threonine kinases is described.

The patent application WO 04/005472 describes, among other things pyrido[2,3-b]pyrazines substituted with carbamate in the 6-position which inhibit the growth of bacteria as antibacterial substances. No antitumour effect is described.

Certain diphenyl quinoxalines and pyrido[2,3-b]pyrazines with special alkylpyrrolidine, alkylpiperidine or alkyl sulfonamides group at a phenyl ring which can additionally also bear urea or carbamate substitutions in the 6- or 7-position are described in patent specifications WO 03/084473, WO 03/086394 and WO 03/086403 as inhibitors of the activity of the serine/threonine kinase Akt. A use in the treatment of cancer diseases is specified for these compounds. No defined indication of a biological effect is given for the pyrido[2,3-b]pyrazine compounds described therein as examples.

Patent specification WO 03/024448 describes amide and acrylamide-substituted pyrido[2,3-b]pyrazines which can also contain carbamates as additional substituents and can be used as histone deacetylase inhibitors for the treatment of cell proliferation diseases.

The publication (S. Laufer, J. Med. Chem. 2010, 53(3), 1128-1137) describes pyridinylpyridopyrazines as lead compounds for novel p38α Mitogen-Activated Protein Kinase Inhibitors.

In another publication (M. R. Dobler, Pest Management Science, 2010, 66(2), 178-185) pyrido[2,3-b]pyrazines are described as tubulin polymerisation promoters.

In the publication (Temple C. et al. 1990) the synthesis of a 6-ethylcarbamate-substituted pyrido[2,3-b]pyrazine derivative is described as one example. No antitumour effect is disclosed or made obvious.

The synthesis of further derivatives of 6-ethylcarbannate-substituted pyrido[2,3-b]pyrazine is described in a publication by R. D. Elliott (J. Org. Chem. 1968). No biological effect of these compounds is described or disclosed.

The publication by C. Temple (1968) describes the synthesis and investigation of 6-ethylcarbamate-substituted pyrido[2,3-b]pyrazines as potential antimalarial drugs. No antitumour effect is disclosed or made obvious.

Several PI3K inhibitors (NVP-Bez-235, GDC-0941, XL-147 and others) undergo clinical trials (reviewed by Maira S. M., et al, 2010).

DESCRIPTION OF THE INVENTION

The object of the present invention is to provide new compounds which can be used for the treatment or prevention of physiological and/or pathophysiological states in mammals, in particular in humans, which are mediated by ras-Raf-Mek-Erk signal transduction pathway.

The inventive object was surprisingly achieved in one aspect by preparing a compound according to the general formula (I)

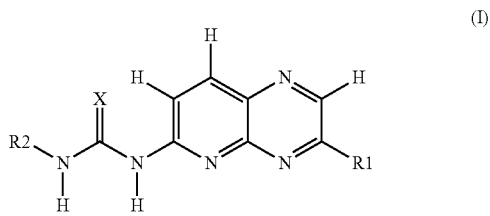

wherein the substituents R1, R2, X have the following meaning:
X O or S
R1
(I) unsubstituted or substituted aryl, wherein the aryl group can be substituted with one or more, the same or different F, Cl, Br, I, $CF_3$, CN, $NH_2$, NH-alkyl, NH-cycloalkyl, NH-heterocyclyl, NH-aryl, NH-heteroaryl, NH-alkyl-cycloalkyl, NH-alkyl-heterocyclyl, NH-alkyl-aryl, NH-alkyl-heteroaryl, NH-alkyl-$NH_2$, NH-alkyl-OH, N(alkyl)$_2$, NHC(O)-alkyl, NHC(O)-cycloalkyl, NHC(O)-heterocyclyl, NHC(O)-aryl, NHC(O)-heteroaryl, NHC(O)-alkyl-aryl, NHC(O)-alkyl-heteroaryl, $NHSO_2$-alkyl, $NHSO_2$-cycloalkyl, $NHSO_2$-heterocyclyl, $NHSO_2$-aryl, $NHSO_2$-heteroaryl, $NHSO_2$-alkyl-aryl, $NHSO_2$-alkyl-heteroaryl, $NO_2$, SH, S-alkyl, S-aryl, S-heteroaryl, OH, $OCF_3$, O-alkyl, O-cycloalkyl, O-heterocyclyl, O-aryl, O-heteroaryl, O-alkyl-cycloalkyl, O-alkyl-heterocyclyl, O-alkyl-aryl, O-alkyl-heteroaryl, O-alkyl-OH, O—$(CH_2)_n$—O, O—$(—CH_2—CH_2—O—)_n$—$CH_2$—$CH_2$—OH, OC(O)-alkyl, OC(O)-cycloalkyl, OC(O)-heterocyclyl, OC(O)-aryl, OC(O)-heteroaryl, OC(O)-alkyl-aryl, OC(O)-alkyl-heteroaryl, OC(O)—NH-Alkyl, $OSO_3H$, $OSO_2$-alkyl, $OSO_2$-cycloalkyl, $OSO_2$-heterocyclyl, $OSO_2$-aryl, $OSO_2$-heteroaryl, $OSO_2$-alkyl-aryl, $OSO_2$-alkyl-heteroaryl, OP(O)(OH)$_2$, C(O)-alkyl, C(O)-aryl, C(O)-heteroaryl, O—$CO_2$-alkyl, $CO_2H$, $CO_2$-alkyl, $CO_2$-cycloalkyl, $CO_2$-heterocyclyl, $CO_2$-aryl, $CO_2$-heteroaryl, $CO_2$-alkyl-cycloalkyl, $CO_2$-alkyl-heterocyclyl, $CO_2$-alkyl-aryl, $CO_2$-alkyl-heteroaryl, C(O)—$NH_2$, C(O)NH-alkyl, C(O)NH-cycloalkyl, C(O)NH-heterocyclyl, C(O)NH-aryl, C(O)NH-heteroaryl, C(O)NH-alkyl-cycloalkyl, C(O)NH-alkyl-heterocyclyl, C(O)NH-alkyl-aryl, C(O)NH-alkyl-heteroaryl, C(O)N(alkyl)$_2$, C(O)N(cycloalkyl)$_2$, C(O)N(aryl)$_2$, C(O)N(heteroaryl)$_2$, SO-alkyl, SO-aryl, $SO_2$-alkyl, $SO_2$-heterocyclyl; $SO_2$-aryl, $SO_2NH_2$, $SO_2$NH-alkyl, $SO_2$NH-aryl, $SO_2$NH-heteroaryl, $SO_2$NH-alkyl-aryl, $SO_3H$, $SO_2$O-alkyl, $SO_2$O-aryl, $SO_2$O-alkyl-aryl, alkyl, cycloalkyl, heterocyclyl, aryl or heteroaryl, n can have the value 0, 1, 2 or 3 and the alkyl-, cycloalkyl-, heterocyclyl-, aryl-, heteroaryl-, alkyl-cycloalkyl-, alkyl-heterocyclyl-, alkyl-aryl- and alkyl-heteroaryl substituents for their part can in turn be substituted,
(II) unsubstituted or substituted heteroaryl, wherein the heteroaryl group can be substituted with one or more, the same or different F, Cl, Br, I, $CF_3$, CN, $NH_2$, NH-alkyl, NH-cycloalkyl, NH-heterocyclyl, NH-aryl, NH-heteroaryl, NH-alkyl-cycloalkyl, NH-alkyl-heterocyclyl, NH-alkyl-aryl, NH-alkyl-heteroaryl, NH-alkyl-$NH_2$, NH-alkyl-OH, N(alkyl)$_2$, NHC(O)-alkyl, NHC(O)-cycloalkyl, NHC(O)-heterocyclyl, NHC(O)-aryl, NHC(O)-heteroaryl, NHC(O)-alkyl-aryl, NHC(O)-alkyl-heteroaryl, $NHSO_2$-alkyl, $NHSO_2$-cycloalkyl, $NHSO_2$-heterocyclyl, $NHSO_2$-aryl, $NHSO_2$-heteroaryl, $NHSO_2$-alkyl-aryl, $NHSO_2$-alkyl-heteroaryl, $NO_2$, SH, S-alkyl, S-aryl, S-heteroaryl, OH, $OCF_3$, O-alkyl, O-cycloalkyl, O-aryl, O-heteroaryl, O-alkyl-cycloalkyl, O-alkyl-heterocyclyl, O-alkyl-aryl, O-alkyl-heteroaryl, OC(O)-alkyl, OC(O)-cycloalkyl, OC(O)-heterocyclyl, OC(O)-aryl, OC(O)-heteroaryl, OC(O)-alkyl-aryl, OC(O)-alkyl-heteroaryl, $OSO_3H$, $OSO_2$-alkyl, $OSO_2$-cycloalkyl, $OSO_2$-heterocyclyl, $OSO_2$-aryl, $OSO_2$-heteroaryl, $OSO_2$-alkyl-aryl, $OSO_2$-alkyl-heteroaryl, OP(O)(OH)$_2$, C(O)-alkyl, C(O)-aryl, C(O)-heteroaryl, $CO_2H$, $CO_2$-alkyl, $CO_2$-cycloalkyl, $CO_2$-heterocyclyl, $CO_2$-aryl, $CO_2$-heteroaryl, $CO_2$-alkyl-cycloalkyl, $CO_2$-alkyl-heterocyclyl, $CO_2$-alkyl-aryl, $CO_2$-alkyl-heteroaryl, C(O)—$NH_2$, C(O)NH-alkyl, C(O)NH-cycloalkyl, C(O)NH-heterocyclyl, C(O)NH-aryl, C(O)NH-heteroaryl, C(O)NH-alkyl-cycloalkyl, C(O)NH-alkyl-heterocyclyl, C(O)NH-alkyl-aryl, C(O)NH-alkyl-heteroaryl, C(O)N(alkyl)$_2$, C(O)N(cycloalkyl)$_2$, C(O)N(aryl)$_2$, C(O)N(heteroaryl)$_2$, $SO_2NH_2$, $SO_2$NH-alkyl, $SO_2$NH-aryl, $SO_2$NH-heteroaryl, $SO_2$NH-alkyl-aryl, $SO_3H$, $SO_2$O-alkyl, $SO_2$O-aryl, $SO_2$O-alkyl-aryl, alkyl, cycloalkyl, heterocyclyl, alkyl-cycloalkyl, alkyl-heterocyclyl, alkyl-aryl, alkyl-heteroaryl, aryl or heteroaryl, and the alkyl-, cycloalkyl-, heterocyclyl-, alkyl-cycloalkyl, alkyl-heterocyclyl, alkyl-aryl, alkyl-heteroaryl, aryl- and heteroaryl substituents for their part can in turn be substituted, (III) NR3R4, wherein R3 and R4 independently of one another can be hydrogen, alkyl, cycloalkyl, heterocyclyl, aryl, heteroaryl, alkyl-cycloalkyl, alkyl-heterocyclyl, alkyl-aryl or alkyl-heteroaryl and the alkyl-, cycloalkyl-, heterocyclyl-, aryl- and heteroaryl-, alkyl-cycloalkyl, alkyl-heterocyclyl, alkyl-aryl or alkyl-heteroaryl substituents for their part can in turn be substituted, or R3 and R4 together mean cycloalkyl or heterocyclyl, wherein cycloalkyl and heterocyclyl for their part can in turn be substituted.

and R2

(I) unsubstituted or substituted alkyl-aryl wherein the alkyl-aryl group can be substituted with one or more, the same or different F, Cl, Br, I, $CF_3$, CN, $NH_2$, NH-alkyl, NH-cycloalkyl, NH-heterocyclyl, NH-aryl, NH-heteroaryl, NH-alkyl-cycloalkyl, NH-alkyl-heterocyclyl, NH-alkyl-aryl, NH-alkyl-heteroaryl, N(alkyl)$_2$, NHC(O)-alkyl, NHC(O)-cycloalkyl, NHC(O)-heterocyclyl, NHC(O)-aryl, NHC(O)-heteroaryl, NHC(O)-alkyl-aryl, NHC(O)-alkyl-heteroaryl, $NHSO_2$-alkyl, $NHSO_2$-cycloalkyl, $NHSO_2$-heterocyclyl, $NHSO_2$-aryl, $NHSO_2$-heteroaryl, $NHSO_2$-alkyl-aryl, $NHSO_2$-alkyl-heteroaryl, $NO_2$, SH, S-alkyl, S-cycloalkyl, S-heterocyclyl, S-aryl, S-heteroaryl, =O, OH, $OCF_3$, O-alkyl, O-cycloalkyl, O-heterocyclyl, O-aryl, O-heteroaryl, O-alkyl-cycloalkyl, O-alkyl-heterocyclyl, O-alkyl-aryl, O-alkyl-heteroaryl, OC(O)-alkyl, OC(O)-cycloalkyl, OC(O)-heterocyclyl, OC(O)-aryl, OC(O)-heteroaryl, OC(O)-alkyl-aryl, OC(O)-alkyl-heteroaryl, $OSO_3H$, $OSO_2$-alkyl, $OSO_2$-cycloalkyl, $OSO_2$-heterocyclyl, $OSO_2$-aryl, $OSO_2$-heteroaryl, $OSO_2$-alkyl-aryl, $OSO_2$-alkyl-heteroaryl, OP(O)(OH)$_2$, C(O)-alkyl, C(O)-aryl, C(O)-heteroaryl, $CO_2H$, $CO_2$-alkyl, $CO_2$-cycloalkyl, $CO_2$-heterocyclyl, $CO_2$-aryl, $CO_2$-heteroaryl, $CO_2$-alkyl-cycloalkyl, $CO_2$-alkyl-heterocyclyl, $CO_2$-alkyl-aryl, $CO_2$-alkyl-heteroaryl, C(O)—$NH_2$, C(O)NH-alkyl, C(O)NH-cycloalkyl, C(O)NH-heterocyclyl, C(O)NH-aryl, C(O)NH-heteroaryl, C(O)NH-alkyl-cycloalkyl, C(O)NH-alkyl-heterocyclyl, C(O)NH-alkyl-aryl, C(O)NH-alkyl-heteroaryl, C(O)N(alkyl)$_2$, C(O)N(cycloalkyl)$_2$, C(O)N(aryl)$_2$, C(O)N(heteroaryl)$_2$, SO-alkyl, SO-aryl, $SO_2$-alkyl, $SO_2$-aryl, $SO_2NH_2$, $SO_2NH$-alkyl, $SO_2NH$-aryl, $SO_2NH$-heteroaryl, $SO_2NH$-alkyl-aryl, $SO_3H$, $SO_2O$-alkyl, $SO_2O$-aryl, $SO_2O$-alkyl-aryl, alkyl, cycloalkyl, heterocyclyl, aryl or heteroaryl, (II) unsubstituted or substituted alkyl-heteroaryl wherein the alkyl-heteroaryl group can be substituted with one or more, the same or different F, Cl, Br, I, $CF_3$, CN, $NH_2$, NH-alkyl, NH-cycloalkyl, NH-heterocyclyl, NH-aryl, NH-heteroaryl, NH-alkyl-cycloalkyl, NH-alkyl-heterocyclyl, NH-alkyl-aryl, NH-alkyl-heteroaryl, N(alkyl)$_2$, NHC(O)-alkyl, NHC(O)-cycloalkyl, NHC(O)-heterocyclyl, NHC(O)-aryl, NHC(O)-heteroaryl, NHC(O)-alkyl-aryl, NHC(O)-alkyl-heteroaryl, $NHSO_2$-alkyl, $NHSO_2$-cycloalkyl, $NHSO_2$-heterocyclyl, $NHSO_2$-aryl, $NHSO_2$-heteroaryl, $NHSO_2$-alkyl-aryl, $NHSO_2$-alkyl-heteroaryl, $NO_2$, SH, S-alkyl, S-cycloalkyl, S-heterocyclyl, S-aryl, S-heteroaryl, OH, $OCF_3$, O-alkyl, O-cycloalkyl, O-heterocyclyl, O-aryl, O-heteroaryl, O-alkyl-cycloalkyl, O-alkyl-heterocyclyl, O-alkyl-aryl, O-alkyl-heteroaryl, OC(O)-alkyl, OC(O)-cycloalkyl, OC(O)-heterocyclyl, OC(O)-aryl, OC(O)-heteroaryl, OC(O)-alkyl-aryl, OC(O)-alkyl-heteroaryl, $OSO_3H$, $OSO_2$-alkyl, $OSO_2$-cycloalkyl, $OSO_2$-heterocyclyl, $OSO_2$-aryl, $OSO_2$-heteroaryl, $OSO_2$-alkyl-aryl, $OSO_2$-alkyl-heteroaryl, OP(O)(OH)$_2$, C(O)-alkyl, C(O)-aryl, C(O)-heteroaryl, $CO_2H$, $CO_2$-alkyl, $CO_2$-cycloalkyl, $CO_2$-heterocyclyl, $CO_2$-aryl, $CO_2$-heteroaryl, $CO_2$-alkyl-cycloalkyl, $CO_2$-alkyl-heterocyclyl, $CO_2$-alkyl-aryl, $CO_2$-alkyl-heteroaryl, C(O)—$NH_2$, C(O)NH-alkyl, C(O)NH-cycloalkyl, C(O)NH-heterocyclyl, C(O)NH-aryl, C(O)NH-heteroaryl, C(O)NH-alkyl-cycloalkyl, C(O)NH-alkyl-heterocyclyl, C(O)NH-alkyl-aryl, C(O)NH-alkyl-heteroaryl, C(O)N(alkyl)$_2$, C(O)N(cycloalkyl)$_2$, C(O)N(aryl)$_2$, C(O)N(heteroaryl)$_2$, SO-alkyl, SO-aryl, $SO_2$-alkyl, $SO_2$-aryl, $SO_2NH_2$, $SO_2NH$-alkyl, $SO_2NH$-aryl, $SO_2NH$-heteroaryl, $SO_2NH$-alkyl-aryl, $SO_3H$, $SO_2O$-alkyl, $SO_2O$-aryl, $SO_2O$-alkyl-aryl, cycloalkyl, heterocyclyl, aryl or heteroaryl, its physiologically tolerated salts, in the form of its racemates, in the form of its pure enantiomers and/or diastereomers or in the form of mixtures of these enantiomers and/or diastereomers or in the form of its tautomers;

which can be used for the production of a medicament for the treatment or prevention of physiological and/or pathophysiological states in mammals mediated by the ras-Raf-Mek-Erk signal transduction pathway.

In a preferred embodiment, compounds according to the general formula (I) are prepared, wherein the alkyl group is selected from the group consisting of: "methyl, ethyl, n-propyl, 2-propyl, n-butyl, sec.-butyl, tert.-butyl, n-pentyl, iso-pentyl, neo-pentyl, n-hexyl, 2-hexyl, n-octyl, ethylenyl (vinyl), ethynyl, propenyl (—CH2CH=CH2; —CH=CH—CH3, —C(=CH2)-CH3), propinyl (—CH2—C≡CH, —C≡C—CH$_3$), butenyl, butinyl, pentenyl, pentinyl, hexenyl, hexinyl, heptenyl, heptinyl, octenyl, octinyl" which can be used for the production of a medicament for the treatment or prevention of physiological and/or pathophysiological states in mammals mediated by signal transduction pathways selected from the group consisting of:

the PI3K-Akt signal transduction pathway and/or the ras-Raf-Mek-Erk signal transduction pathway.

In a further preferred embodiment, compounds according to the general formula (I) are prepared for the aforementioned use, wherein the heterocyclyl group is selected from the group consisting of: "tetrahydrofuryl, tetrahydropyranyl, pyrrolidinyl, piperidinyl, piperazinyl, morpholinyl".

In a further preferred embodiment, compounds according to the general formula (I) are prepared for the aforementioned use, wherein the heteroaryl group is selected from the group consisting of: "pyrrolyl, furyl, thienyl, thiazolyl, oxazolyl, isoxazolyl, pyrazolyl, imidazolyl, pyridinyl, pyrimidinyl, pyridazinyl, pyrazinyl, phthalazinyl, indolyl, indazolyl, indolizinyl, benzimidazolyl, quinolinyl, isoquinolinyl, quinoxalinyl, quinazolinyl, carbazolyl, phenazinyl, phenothiazinyl, acridinyl".

In a further preferred embodiment compounds according to the general formula (I) are prepared for the aforementioned use, wherein the alkyl group is selected from the group consisting of: "methyl, ethyl, n-propyl, 2-propyl, n-butyl, sec.-butyl, tert.-butyl, n-pentyl, iso-pentyl, neo-pentyl, n-hexyl, 2-hexyl, n-octyl, ethylenyl (vinyl), ethynyl, propenyl (—CH2CH=CH2; —CH=CH—CH3, —C(=CH2)-CH3), propinyl (—CH2—C≡CH, —C≡CH—CH3), butenyl, butinyl, pentenyl, pentinyl, hexenyl, hexinyl, heptenyl, heptinyl, octenyl, octinyl" and/or wherein the heterocyclyl group is selected from the group consisting of: "tetrahydrofuryl, tetrahydropyranyl, pyrrolidinyl, piperidinyl, piperazinyl, morpholinyl" and/or the heteroaryl group is selected from the group consisting of: "pyrrolyl, furyl, thienyl, thiazolyl, oxazolyl, isoxazolyl, pyrazolyl, imidazolyl, pyridinyl, pyrimidinyl, pyridazinyl, pyrazinyl, phthalazinyl, indolyl, indazolyl, indolizinyl, benzimidazolyl, quinolinyl, isoquinolinyl, quinoxalinyl, quinazolinyl, carbazolyl, phenazinyl, phenothiazinyl, acridinyl".

The inventive object was surprisingly achieved in a further aspect by preparing pyridopyrazine compounds selected from the group consisting of:

Compound 90: 1-[3-(4-{2-[2-(2-Hydroxy-ethoxy)-ethoxy]-ethoxy}-phenyl)-pyrido[2,3-b]pyrazin-6-yl]-3-(4-phenyl-butyl)-urea

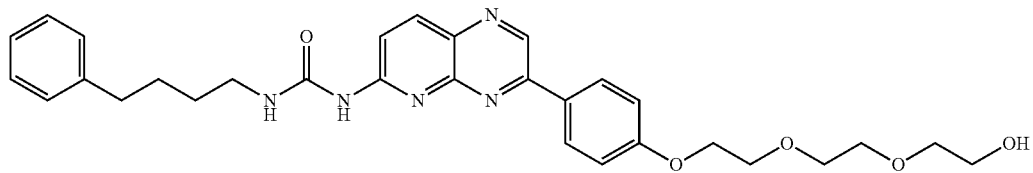 [SMILES: O=C(NCCCCc1ccccc1)Nc1ccc2ncc(-c3ccc(OCCOCCOCCO)cc3)nc2n1]

Compound 91: 1-[3-(3,5-Dimethyl-1H-pyrazol-4-yl)-pyrido[2,3-b]pyrazin-6-yl]-3-(4-phenyl-butyl)-urea

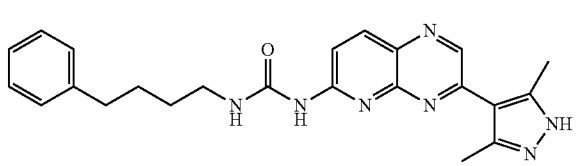 [SMILES: Cc1n[nH]c(C)c1-c1cnc2ccc(NC(=O)NCCCCc3ccccc3)nc2n1]

Compound 92: 1-(4-Phenyl-butyl)-3-[3-(2,3,4-tri-methoxy-phenyl)-pyrido[2,3-b]pyrazin-6-yl]-urea

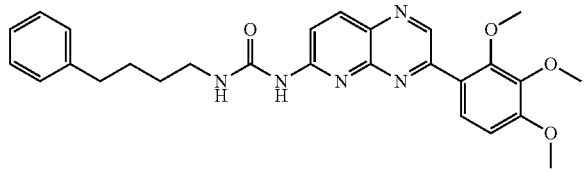 [SMILES: COc1ccc(-c2cnc3ccc(NC(=O)NCCCCc4ccccc4)nc3n2)c(OC)c1OC]

Compound 93: 1-[3-(4-Methyl-piperazin-1-yl)-pyrido[2,3-b]pyrazin-6-yl]-3-(4-phenyl-butyl)-urea

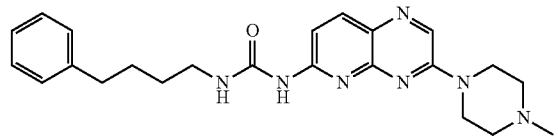 [SMILES: CN1CCN(c2cnc3ccc(NC(=O)NCCCCc4ccccc4)nc3n2)CC1]

Compound 94: 1-[3-(3H-Benzoimidazol-5-yl)-pyrido[2,3-b]pyrazin-6-yl]-3-(4-phenyl-butyl)-urea

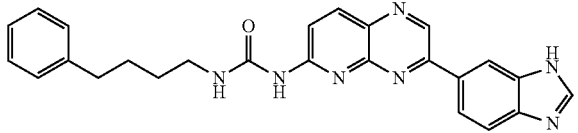 [SMILES: O=C(NCCCCc1ccccc1)Nc1ccc2ncc(-c3ccc4nc[nH]c4c3)nc2n1]

Compound 95: 1-[3-(3-Amino-phenyl)-pyrido[2,3-b]pyrazin-6-yl]-3-(4-phenyl-butyl)-urea

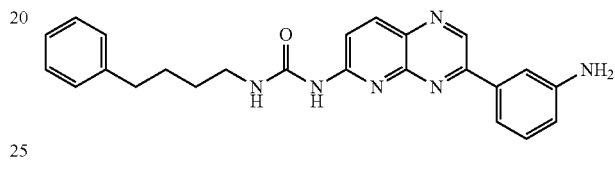

Compound 96: 1-(4-Phenyl-butyl)-3-(3-piperazin-1-yl-pyrido[2,3-b]pyrazin-6-yl)-urea; hydrochloride

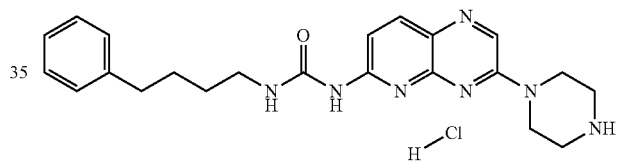

Compound 97: 1-[3-(1-Methyl-1H-pyrazol-4-yl)-pyrido[2,3-b]pyrazin-6-yl]-3-(4-p-tolyl-butyl)-urea

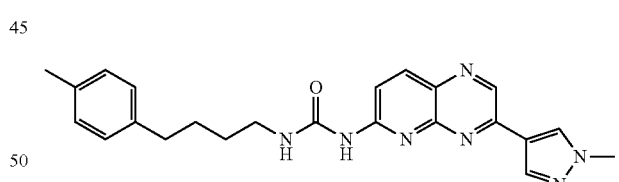

Compound 98: 1-[3-(3,4-Dimethoxy-phenyl)-pyrido[2,3-b]pyrazin-6-yl]-3-((R)-1-methyl-4-phenyl-butyl)-urea

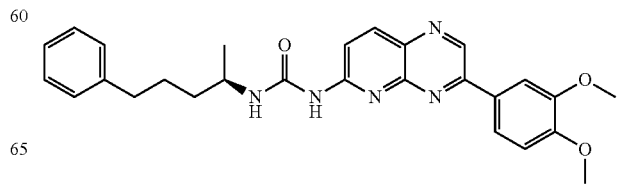

Compound 99: 1-[4-(4-Fluoro-phenyl)-butyl]-3-[3-(1-methyl-1H-pyrazol-4-yl)-pyrido[2,3-b]pyrazin-6-yl]-urea

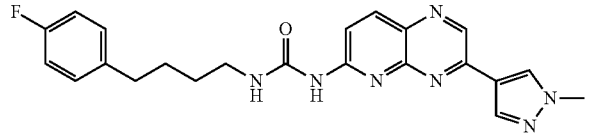 [SMILES: Cn1cc(-c2cnc3ccc(NC(=O)NCCCCc4ccc(F)cc4)nc3n2)cn1]

Compound 100: 1-(4-Methyl-4-phenyl-pentyl)-3-[3-(1-propyl-1H-pyrazol-4-yl)-pyrido[2,3-b]pyrazin-6-yl]-urea

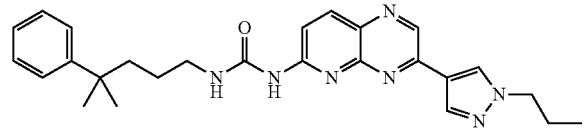 [SMILES: CCCn1cc(-c2cnc3ccc(NC(=O)NCCCC(C)(C)c4ccccc4)nc3n2)cn1]

Compound 101: 1-[3-(2,4-Dimethoxy-phenyl)-pyrido[2,3-b]pyrazin-6-yl]-3-(4-phenyl-butyl)-urea

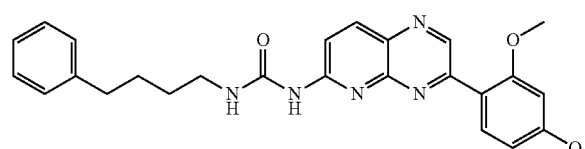

Compound 102: 1-[3-(2-Ethoxy-phenyl)-pyrido[2,3-b]pyrazin-6-yl]-3-(4-phenyl-butyl)-urea

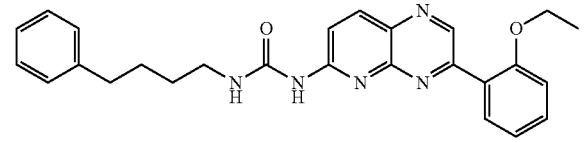 [SMILES: CCOc1ccccc1-c1cnc2ccc(NC(=O)NCCCCc3ccccc3)nc2n1]

Compound 103: 1-[3-(3,5-Dichloro-4-hydroxy-phenyl)-pyrido[2,3-b]pyrazin-6-yl]-3-(4-phenyl-butyl)-urea

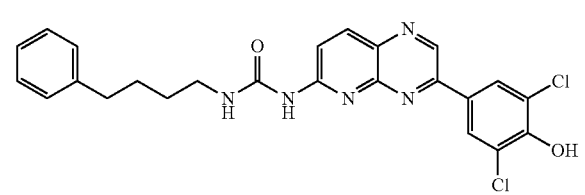 [SMILES: O=C(NCCCCc1ccccc1)Nc1ccc2ncc(-c3cc(Cl)c(O)c(Cl)c3)nc2n1]

Compound 104: 1-[3-(3-Hydroxy-phenyl)-pyrido[2,3-b]pyrazin-6-yl]-3-(4-phenyl-butyl)-urea

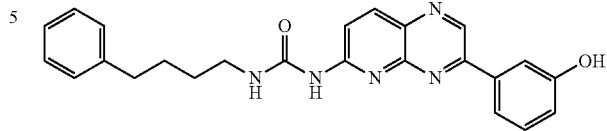

Compound 105: 1-(4-Phenyl-butyl)-3-[3-(2H-pyrazol-3-yl)-pyrido[2,3-b]pyrazin-6-yl]-urea

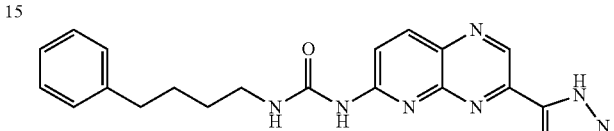

Compound 106: 1-[3-(4-Hydroxy-2-methyl-phenyl)-pyrido[2,3-b]pyrazin-6-yl]-3-(4-phenyl-butyl)-urea

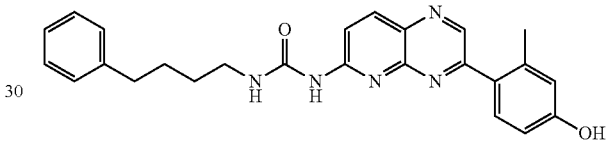

Compound 107: Acetic acid 4-{6-[3-(4-phenyl-butyl)-ureido]-pyrido[2,3-b]pyrazin-3-yl}-phenyl ester

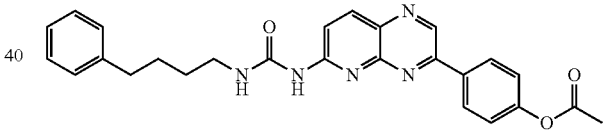

Compound 108: 1-[3-(1-Ethyl-1H-pyrazol-4-yl)-pyrido[2,3-b]pyrazin-6-yl]-3-(4-phenyl-butyl)-urea

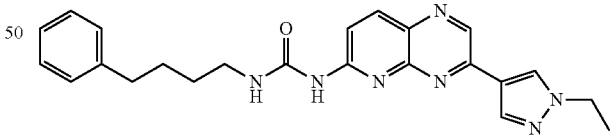

Compound 109: 1-[3-(3-Bromo-4-hydroxy-phenyl)-pyrido[2,3-b]pyrazin-6-yl]-3-(4-phenyl-butyl)-urea

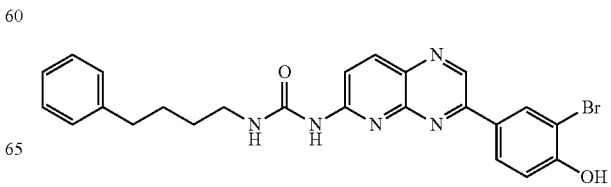

Compound 110: 1-(4-Phenyl-butyl)-3-(3-pyridin-3-yl-pyrido[2,3-b]pyrazin-6-yl)-urea

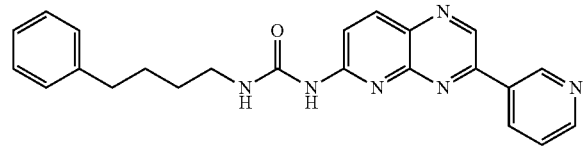 [SMILES: O=C(NCCCCc1ccccc1)Nc1ccc2ncc(-c3cccnc3)nc2n1]

Compound 111: 1-[3-(1-Methyl-1H-pyrazol-4-yl)-pyrido[2,3-b]pyrazin-6-yl]-3-(1,2,3,4-tetrahydro-naphthalen-2-ylmethyl)-urea

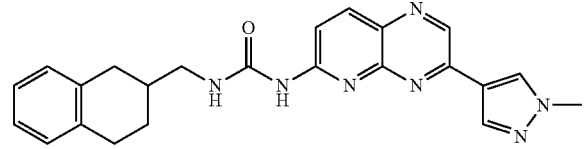 [SMILES: Cn1cc(-c2cnc3ccc(NC(=O)NCC4CCc5ccccc5C4)nc3n2)cn1]

Compound 112: 1-[3-(2,3-Dimethoxy-phenyl)-pyrido[2,3-b]pyrazin-6-yl]-3-((R)-1-methyl-4-phenyl-butyl)-urea

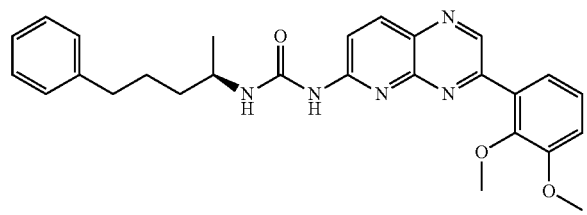 [SMILES: COc1cccc(-c2cnc3ccc(NC(=O)N[C@H](C)CCCc4ccccc4)nc3n2)c1OC]

Compound 113: 1-[3-(5-Methyl-1-phenyl-1H-pyrazol-4-yl)-pyrido[2,3-b]pyrazin-6-yl]-3-(4-phenyl-butyl)-urea

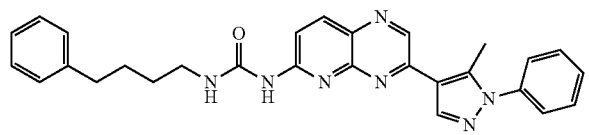 [SMILES: Cc1c(-c2cnc3ccc(NC(=O)NCCCCc4ccccc4)nc3n2)cnn1-c1ccccc1]

Compound 114: 1-[3-(1-Butyl-1H-pyrazol-4-yl)-pyrido[2,3-b]pyrazin-6-yl]-3-(4-phenyl-butyl)-urea

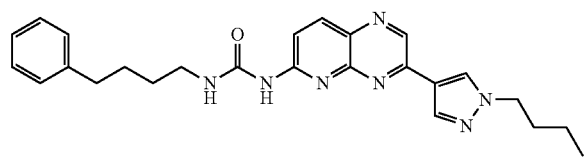 [SMILES: CCCCn1cc(-c2cnc3ccc(NC(=O)NCCCCc4ccccc4)nc3n2)cn1]

Compound 115: 1-[4-(4-Methoxy-phenyl)-butyl]-3-[3-(1-methyl-1H-pyrazol-4-yl)-pyrido[2,3-b]pyrazin-6-yl]-urea

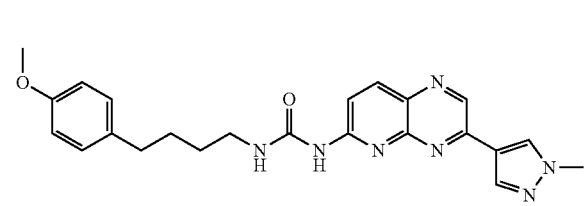 [SMILES: COc1ccc(CCCCNC(=O)Nc2ccc3ncc(-c4cnn(C)c4)nc3n2)cc1]

Compound 116: 1-(4-Phenyl-butyl)-3-[3-(piperidin-4-ylamino)-pyrido[2,3-b]pyrazin-6-yl]-urea

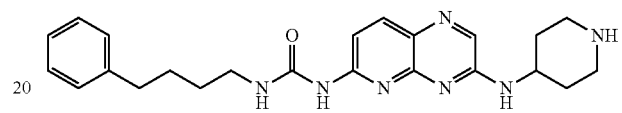

Compound 117: 1-(4-Phenyl-butyl)-3-{3-[(pyridin-4-ylmethyl)-amino]-pyrido[2,3-b]pyrazin-6-yl}-urea

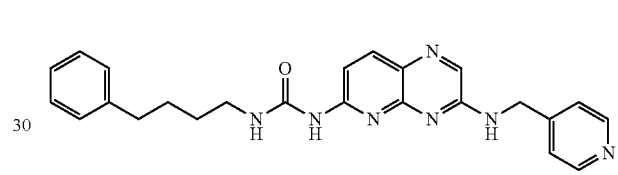

Compound 118: 1-[3-(4-Methoxy-phenyl)-pyrido[2,3-b]pyrazin-6-yl]-3-(4-phenyl-butyl)-urea

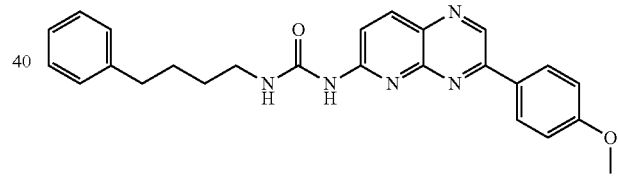

Compound 119: 1-(4-Phenyl-butyl)-3-(3-propylamino-pyrido[2,3-b]pyrazin-6-yl)-urea

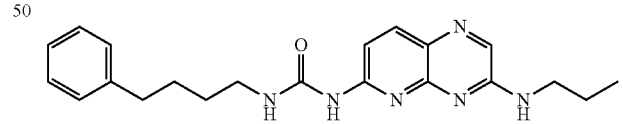

Compound 120: 1-(4-Phenyl-butyl)-3-(3-o-tolyl-pyrido[2,3-b]pyrazin-6-yl)-urea

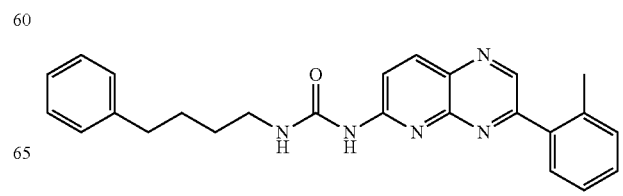

Compound 121: 3-{6-[3-(4-Phenyl-butyl)-ureido]-pyrido[2,3-b]pyrazin-3-yl}-benzoic acid ethyl ester

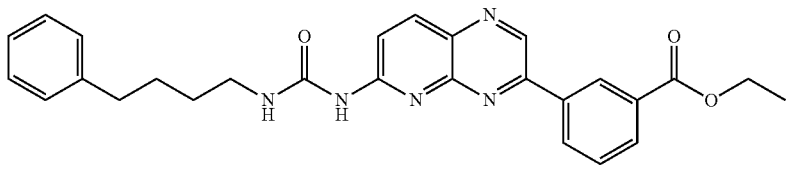 [SMILES: CCOC(=O)c1cccc(-c2cnc3ccc(NC(=O)NCCCCc4ccccc4)nc3n2)c1]

Compound 122: Ethyl-carbamic acid 4-{6-[3-(4-phenyl-butyl)-ureido]-pyrido[2,3-b]pyrazin-3-yl}-phenyl ester

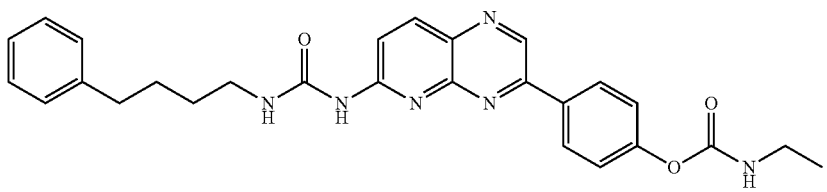 [SMILES: CCNC(=O)Oc1ccc(-c2cnc3ccc(NC(=O)NCCCCc4ccccc4)nc3n2)cc1]

Compound 123: 1-[3-(4-Amino-3-methoxy-phenyl)-pyrido[2,3-b]pyrazin-6-yl]-3-(4-phenyl-butyl)-urea

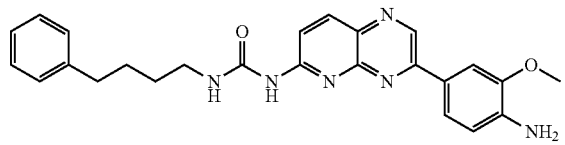 [SMILES: COc1cc(-c2cnc3ccc(NC(=O)NCCCCc4ccccc4)nc3n2)ccc1N]

Compound 124: 1-[3-(2-Methoxy-phenyl)-pyrido[2,3-b]pyrazin-6-yl]-3-(4-phenyl-butyl)-urea

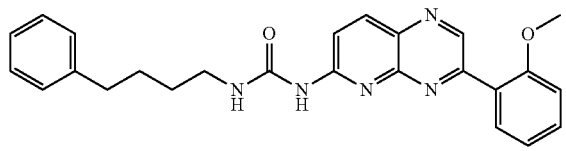 [SMILES: COc1ccccc1-c1cnc2ccc(NC(=O)NCCCCc3ccccc3)nc2n1]

Compound 125: 1-((R)-1-Methyl-4-phenyl-butyl)-3-[3-(2,3,4-trimethoxy-phenyl)-pyrido[2,3-b]pyrazin-6-yl]-urea

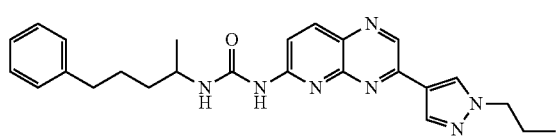 [SMILES: CCCn1cc(-c2cnc3ccc(NC(=O)NC(C)CCCc4ccccc4)nc3n2)cn1]

Compound 126: 1-(1-Methyl-4-phenyl-butyl)-3-[3-(1-propyl-1H-pyrazol-4-yl)-pyrido[2,3-b]pyrazin-6-yl]-urea

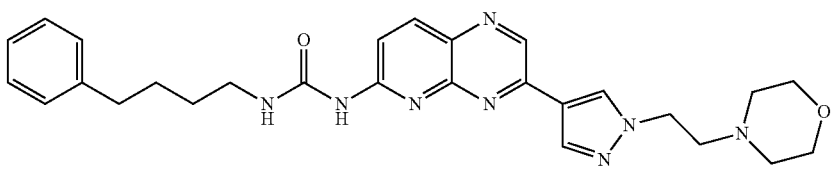 [SMILES: O=C(NCCCCc1ccccc1)Nc1ccc2ncc(-c3cnn(CCN4CCOCC4)c3)nc2n1]

Compound 127: 1-{3-[1-(2-Morpholin-4-yl-ethyl)-1H-pyrazol-4-yl]-pyrido[2,3-b]pyrazin-6-yl}-3-(4-phenyl-butyl)-urea Compound 128: 1-[3-(2-Ethoxy-phenyl)-pyrido[2,3-b]pyrazin-6-yl]-3-((R)-1-methyl-4-phenyl-butyl)-urea

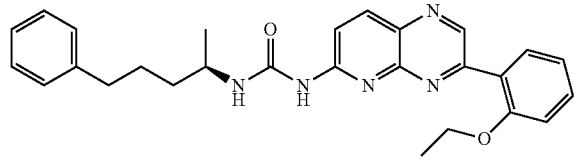 [SMILES: CCOc1ccccc1-c1cnc2ccc(NC(=O)N[C@H](C)CCCc3ccccc3)nc2n1]

Compound 129: 1-[3-(3-Chloro-4-hydroxy-phenyl)-pyrido[2,3-b]pyrazin-6-yl]-3-((R)-1-methyl-4-phenyl-butyl)-urea

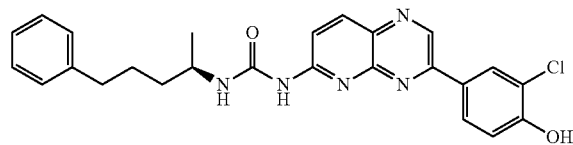 [SMILES: C[C@H](CCCc1ccccc1)NC(=O)Nc1ccc2ncc(-c3ccc(O)c(Cl)c3)nc2n1]

Compound 130: 1-[3-(2-Amino-phenyl)-pyrido[2,3-b]pyrazin-6-yl]-3-(4-phenyl-butyl)-urea

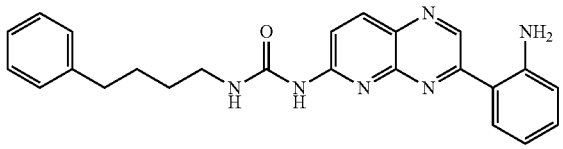 [SMILES: Nc1ccccc1-c1cnc2ccc(NC(=O)NCCCCc3ccccc3)nc2n1]

Compound 131: 1-(4-Oxo-4-phenyl-butyl)-3-[3-(1-propyl-1H-pyrazol-4-yl)-pyrido[2,3-b]pyrazin-6-yl]-urea

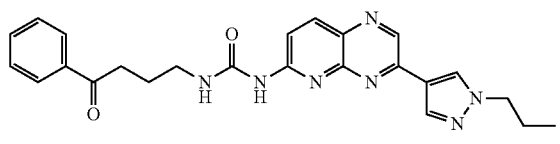 [SMILES: CCCn1cc(-c2cnc3ccc(NC(=O)NCCCC(=O)c4ccccc4)nc3n2)cn1]

Compound 132: Carbonic acid ethyl ester 4-{6-[3-(4-phenyl-butyl)-ureido]-pyrido[2,3-b]pyrazin-3-yl}-phenyl ester

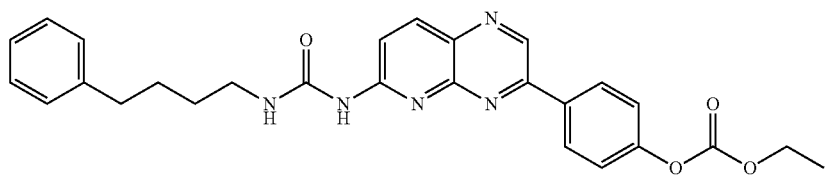 [SMILES: CCOC(=O)Oc1ccc(-c2cnc3ccc(NC(=O)NCCCCc4ccccc4)nc3n2)cc1]

Compound 133: 1-[3-(2-Hydroxy-phenyl)-pyrido[2,3-b]pyrazin-6-yl]-3-(4-phenyl-butyl)-urea

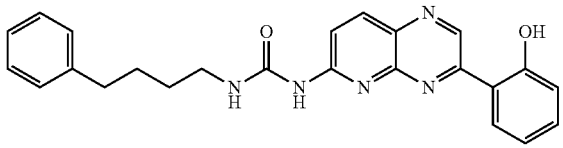 [SMILES: O=C(NCCCCc1ccccc1)Nc1ccc2ncc(-c3ccccc3O)nc2n1]

Compound 134: 1-[3-(4-Hydroxy-cyclohexylamino)-pyrido[2,3-b]pyrazin-6-yl]-3-(4-phenyl-butyl)-urea

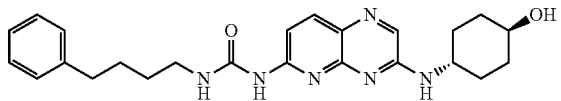 [SMILES: O=C(NCCCCc1ccccc1)Nc1ccc2ncc(N[C@H]3CC[C@H](O)CC3)nc2n1]

Compound 135: 2,2-Dimethyl-propionic acid 4-{6-[3-(4-phenyl-butyl)-ureido]-pyrido[2,3-b]pyrazin-3-yl}-phenyl ester

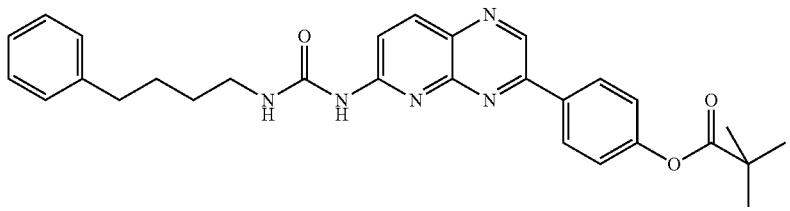 [SMILES: CC(C)(C)C(=O)Oc1ccc(-c2cnc3ccc(NC(=O)NCCCCc4ccccc4)nc3n2)cc1]

Compound 137: 1-[3-(4-Methylsulfanyl-phenyl)-pyrido[2,3-b]pyrazin-6-yl]-3-(4-phenyl-butyl)-urea

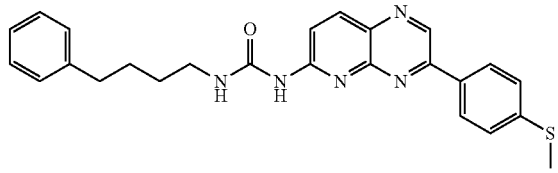 [SMILES: CSc1ccc(-c2cnc3ccc(NC(=O)NCCCCc4ccccc4)nc3n2)cc1]

Compound 138: 1-[3-(3-Cyano-phenyl)-pyrido[2,3-b]pyrazin-6-yl]-3-(4-phenyl-butyl)-urea

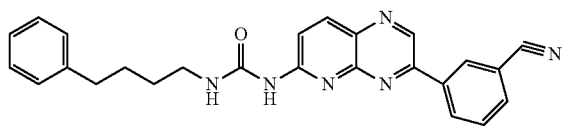 [SMILES: N#Cc1cccc(-c2cnc3ccc(NC(=O)NCCCCc4ccccc4)nc3n2)c1]

Compound 139: 1-(4-Phenyl-butyl)-3-[3-(3,4,5-trimethoxy-phenylamino)-pyrido[2,3-b]pyrazin-6-yl]-urea

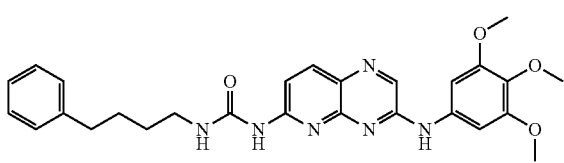 [SMILES: COc1cc(Nc2cnc3ccc(NC(=O)NCCCCc4ccccc4)nc3n2)cc(OC)c1OC]

Compound 140: 1-{3-[(S)-1-(3-Chloro-phenyl)-2-hydroxy-ethylamino]-pyrido[2,3-b]pyrazin-6-yl}-3-(4-phenyl-butyl)-urea

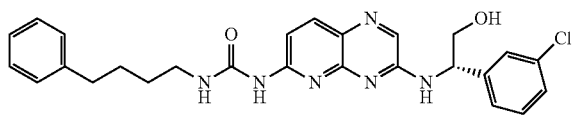 [SMILES: O=C(NCCCCc1ccccc1)Nc1ccc2ncc(N[C@H](CO)c3cccc(Cl)c3)nc2n1]

Compound 141: 1-[3-(3-Hydroxy-4,5-dimethoxy-phenylamino)-pyrido[2,3-b]pyrazin-6-yl]-3-(4-phenyl-butyl)-urea

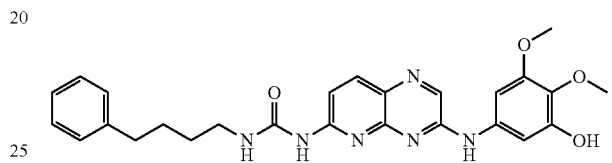

Compound 142: 1-{3-[1-(3-Chloro-phenyl)-2-hydroxy-ethylamino]-pyrido[2,3-b]pyrazin-6-yl}-3-(4-phenyl-butyl)-urea

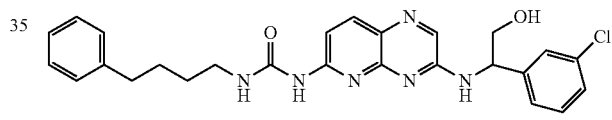

Compound 144: 1-[3-(4-Fluoro-2-hydroxy-phenyl)-pyrido[2,3-b]pyrazin-6-yl]-3-(4-phenyl-butyl)-urea

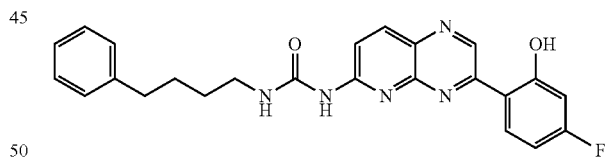

Compound 145: 1-{3-[4-Methoxy-3-(morpholine-4-sulfonyl)-phenyl]-pyrido[2,3-b]pyrazin-6-yl}-3-(4-phenyl-butyl)-urea

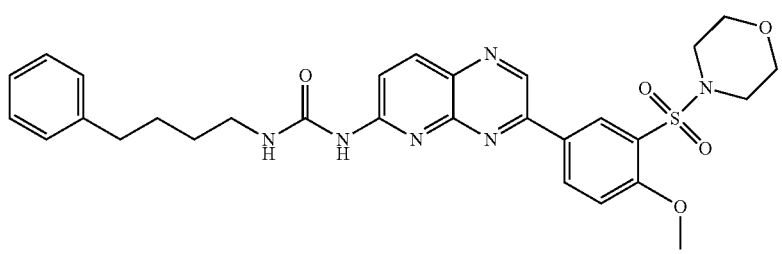 [SMILES: COc1ccc(-c2cnc3ccc(NC(=O)NCCCCc4ccccc4)nc3n2)cc1S(=O)(=O)N1CCOCC1]

Compound 146: 1-[3-(2-Methoxy-pyridin-3-yl)-pyrido[2,3-b]pyrazin-6-yl]-3-(4-phenyl-butyl)-urea

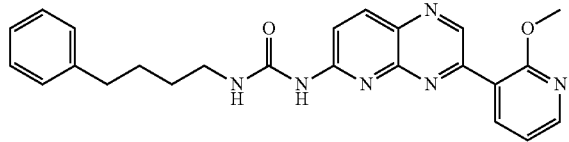 [SMILES: COc1ncccc1-c1cnc2ccc(NC(=O)NCCCCc3ccccc3)nc2n1]

Compound 147: 1-[3-(4-Hydroxy-phenyl)-pyrido[2,3-b]pyrazin-6-yl]-3-((R)-1-methyl-4-phenyl-butyl)-urea

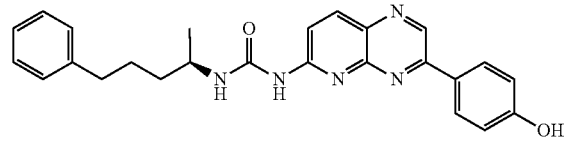 [SMILES: C[C@H](CCCc1ccccc1)NC(=O)Nc1ccc2ncc(-c3ccc(O)cc3)nc2n1]

Compound 148: 1-[3-(3-Hydroxy-4-methoxy-phenyl)-pyrido[2,3-b]pyrazin-6-yl]-3-((R)-1-methyl-4-phenyl-butyl)-urea

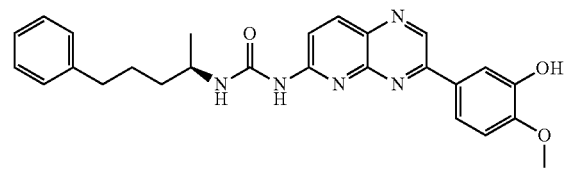 [SMILES: COc1ccc(-c2cnc3ccc(NC(=O)N[C@H](C)CCCc4ccccc4)nc3n2)cc1O]

Compound 149: 1-(3-Furan-3-yl-pyrido[2,3-b]pyrazin-6-yl)-3-((R)-1-methyl-4-phenyl-butyl)-urea

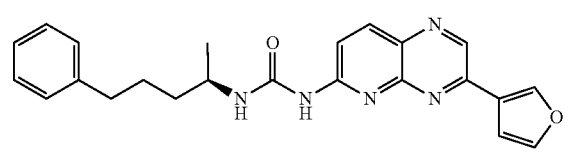 [SMILES: C[C@H](CCCc1ccccc1)NC(=O)Nc1ccc2ncc(-c3ccoc3)nc2n1]

Compound 150: 1-((R)-1-Methyl-4-phenyl-butyl)-3-(3-pyridin-3-yl-pyrido[2,3-b]pyrazin-6-yl)-urea

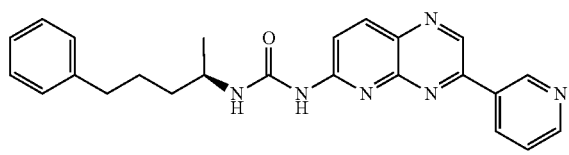 [SMILES: C[C@H](CCCc1ccccc1)NC(=O)Nc1ccc2ncc(-c3cccnc3)nc2n1]

Compound 151: 1-[3-(3-Hydroxy-4-methoxy-phenyl)-pyrido[2,3-b]pyrazin-6-yl]-3-(4-phenyl-butyl)-urea

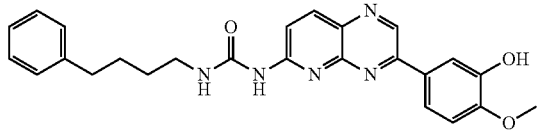 [SMILES: COc1ccc(-c2cnc3ccc(NC(=O)NCCCCc4ccccc4)nc3n2)cc1O]

Compound 152: 1-(3-Furan-3-yl-pyrido[2,3-b]pyrazin-6-yl)-3-(4-phenyl-butyl)-urea

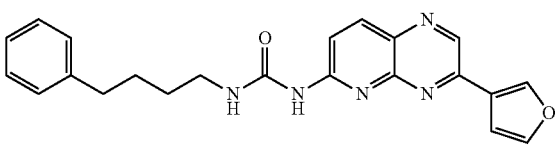 [SMILES: O=C(NCCCCc1ccccc1)Nc1ccc2ncc(-c3ccoc3)nc2n1]

Compound 153: 1-((R)-1-Methyl-4-phenyl-butyl)-3-[3-(4-methyl-piperazin-1-yl)-pyrido[2,3-b]pyrazin-6-yl]-urea

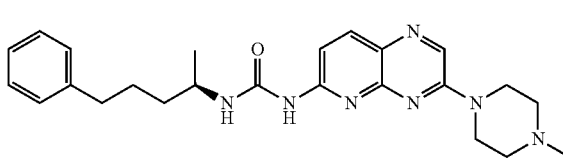

Compound 154: 1-((R)-1-Methyl-4-phenyl-butyl)-3-(3-piperidin-1-yl-pyrido[2,3-b]pyrazin-6-yl)-urea

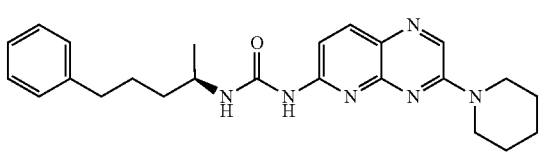 [SMILES: C[C@H](CCCc1ccccc1)NC(=O)Nc1ccc2ncc(N3CCCCC3)nc2n1]

Compound 155: 1-[3-(1-Methyl-1H-pyrazol-4-yl)-pyrido[2,3-b]pyrazin-6-yl]-3-(4-phenyl-butyl)-urea

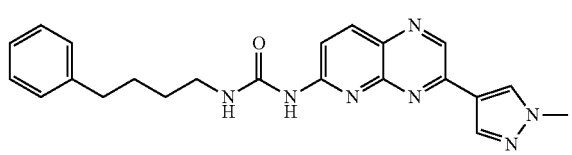 [SMILES: Cn1cc(-c2cnc3ccc(NC(=O)NCCCCc4ccccc4)nc3n2)cn1]

Compound 156: 1-[3-(4-Hydroxymethyl-2-methoxy-phenyl)-pyrido[2,3-b]pyrazin-6-yl]-3-((R)-1-methyl-4-phenyl-butyl)-urea

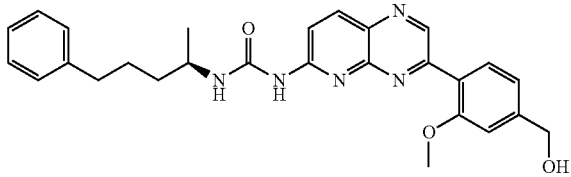 [SMILES: COc1cc(CO)ccc1-c1cnc2ccc(NC(=O)N[C@H](C)CCCc3ccccc3)nc2n1]

Compound 157: 1-((R)-1-Methyl-4-phenyl-butyl)-3-(3-pyridin-4-yl-pyrido[2,3-b]pyrazin-6-yl)-urea

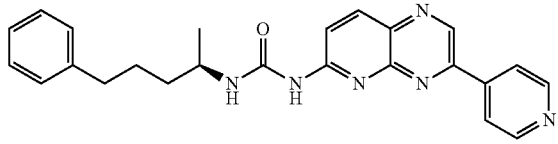 [SMILES: C[C@H](CCCc1ccccc1)NC(=O)Nc1ccc2ncc(-c3ccncc3)nc2n1]

Compound 158: 1-[3-(3-Hydroxymethyl-2-methoxy-phenyl)-pyrido[2,3-b]pyrazin-6-yl]-3-((R)-1-methyl-4-phenyl-butyl)-urea

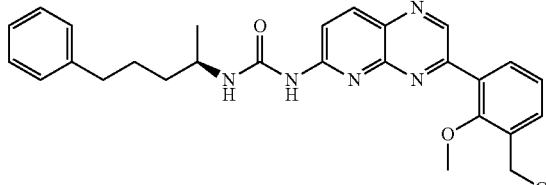

Compound 159: 1-(4-Phenyl-butyl)-3-[3-(1H-pyrazol-4-yl)-pyrido[2,3-b]pyrazin-6-yl]-urea

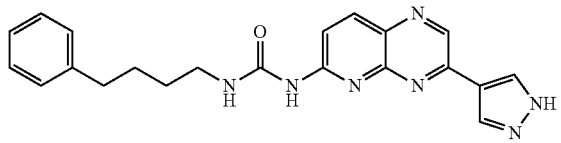 [SMILES: O=C(NCCCCc1ccccc1)Nc1ccc2ncc(-c3cn[nH]c3)nc2n1]

Compound 160: 1-[3-(4-Hydroxy-phenyl)-pyrido[2,3-b]pyrazin-6-yl]-3-(4-phenyl-butyl)-urea

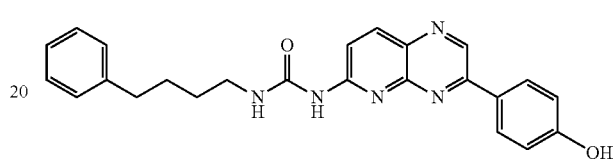

Compound 161: 1-[3-(2-Methoxy-pyridin-3-yl)-pyrido[2,3-b]pyrazin-6-yl]-3-((R)-1-methyl-4-phenyl-butyl)-urea

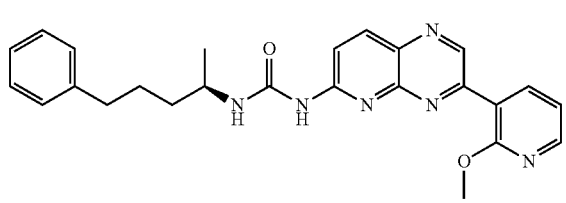 [SMILES: COc1ncccc1-c1cnc2ccc(NC(=O)N[C@H](C)CCCc3ccccc3)nc2n1]

Compound 162: 1-{3-[1-(3-Hydroxy-propyl)-1H-pyrazol-4-yl]-pyrido[2,3-b]pyrazin-6-yl}-3-(4-phenyl-butyl)-urea

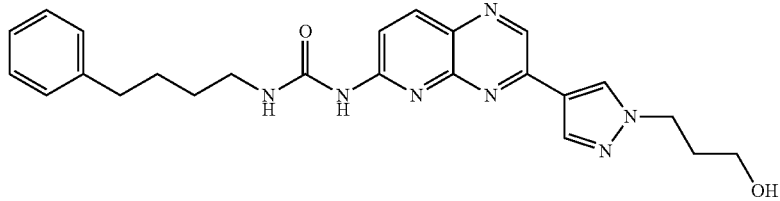 [SMILES: O=C(NCCCCc1ccccc1)Nc1ccc2ncc(-c3cnn(CCCO)c3)nc2n1]

Compound 163: 1-{3-[1-(2,2-Difluoro-ethyl)-1H-pyrrol-3-yl]-pyrido[2,3-b]pyrazin-6-yl}-3-(4-phenyl-butyl)-urea

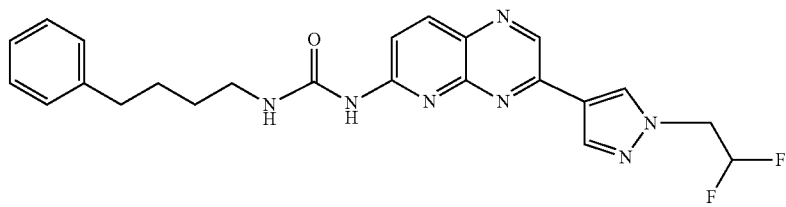 [SMILES: O=C(NCCCCc1ccccc1)Nc1ccc2ncc(-c3cnn(CC(F)F)c3)nc2n1]

Compound 164: 1-(1-Methyl-4-phenyl-butyl)-3-[3-(1-methyl-1H-pyrazol-4-yl)-pyrido[2,3-b]pyrazin-6-yl]-urea

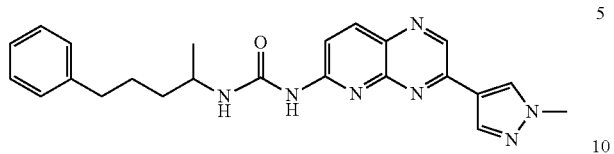

Compound 165: Phosphoric acid mono-(4-{6-[3-(4-phenyl-butyl)-ureido]-pyrido[2,3-b]pyrazin-3-yl}-phenyl) ester

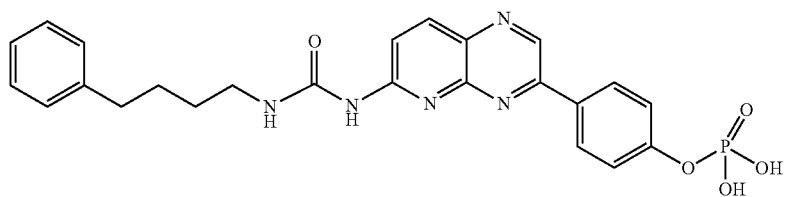 [SMILES: O=C(NCCCCc1ccccc1)Nc1ccc2ncc(-c3ccc(OP(=O)(O)O)cc3)nc2n1]

Compound 166: 1-((R)-1-Methyl-4-phenyl-butyl)-3-(3-morpholin-4-yl-pyrido[2,3-b]pyrazin-6-yl)-urea

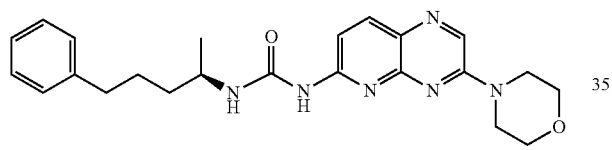

Compound 167: 1-[3-(4-Hydroxymethyl-phenyl)-pyrido[2,3-b]pyrazin-6-yl]-3-((R)-1-methyl-4-phenyl-butyl)-urea

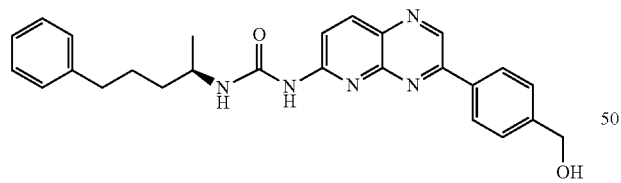

Compound 168: 1-((R)-1-Methyl-4-phenyl-butyl)-3-{3-[1-(2-morpholin-4-yl-ethyl)-1H-pyrazol-4-yl]-pyrido[2,3-b]pyrazin-6-yl}-urea

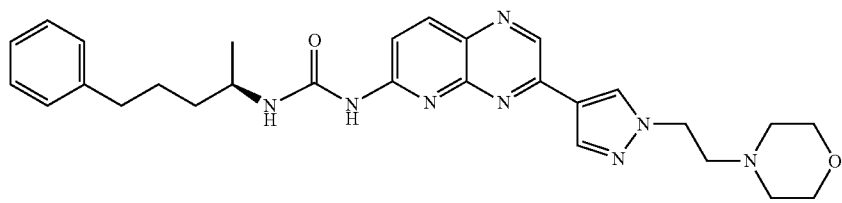 [SMILES: C[C@H](CCCc1ccccc1)NC(=O)Nc1ccc2ncc(-c3cnn(CCN4CCOCC4)c3)nc2n1]

Compound 169: 1-(4-Methyl-4-phenyl-pentyl)-3-[3-(1-methyl-1H-pyrazol-4-yl)-pyrido[2,3-b]pyrazin-6-yl]-urea

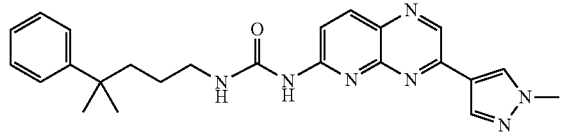 [SMILES: Cn1cc(-c2cnc3ccc(NC(=O)NCCCC(C)(C)c4ccccc4)nc3n2)cn1]

Compound 170: 1-((R)-1-Methyl-4-phenyl-butyl)-3-[3-(1-propyl-1H-pyrazol-4-yl)-pyrido[2,3-b]pyrazin-6-yl]-urea

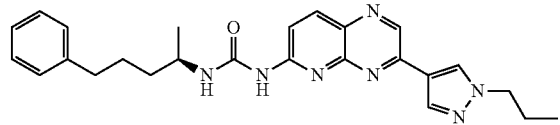

Compound 171: 1-((R)-1-Methyl-4-phenyl-butyl)-3-[3-(1H-pyrazol-4-yl)-pyrido[2,3-b]pyrazin-6-yl]-urea

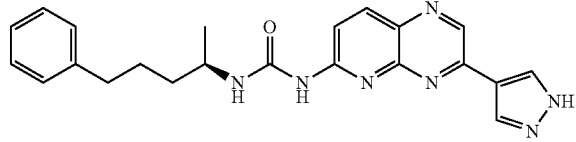 [SMILES: C[C@H](CCCc1ccccc1)NC(=O)Nc1ccc2ncc(-c3cn[nH]c3)nc2n1]

Compound 172: 1-(4-Phenyl-butyl)-3-(3-pyrrolidin-1-yl-pyrido[2,3-b]pyrazin-6-yl)-urea

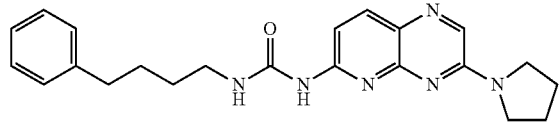 [SMILES: O=C(NCCCCc1ccccc1)Nc1ccc2ncc(N3CCCC3)nc2n1]

Compound 173: 1-((R)-1-Methyl-4-phenyl-butyl)-3-(3-pyrrolidin-1-yl-pyrido[2,3-b]pyrazin-6-yl)-urea

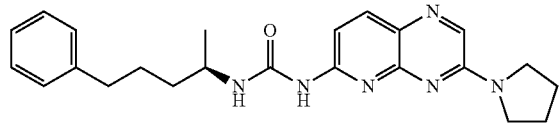 [SMILES: C[C@H](CCCc1ccccc1)NC(=O)Nc1ccc2ncc(N3CCCC3)nc2n1]

Compound 174: 1-[3-(3-Fluoro-4-hydroxy-phenyl)-pyrido[2,3-b]-pyrazin-6-yl]-3-(4-phenyl-butyl)-urea

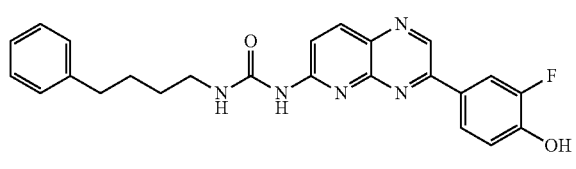 [SMILES: O=C(NCCCCc1ccccc1)Nc1ccc2ncc(-c3ccc(O)c(F)c3)nc2n1]

Compound 175: 1-[3-(3-Hydroxymethyl-phenyl)-pyrido[2,3-b]pyrazin-6-yl]-3-(4-phenyl-butyl)-urea

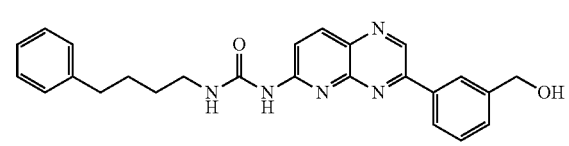 [SMILES: O=C(NCCCCc1ccccc1)Nc1ccc2ncc(-c3cccc(CO)c3)nc2n1]

Compound 176: 1-(3-Morpholin-4-yl-pyrido[2,3-b]pyrazin-6-yl)-3-(4-phenyl-butyl)-urea

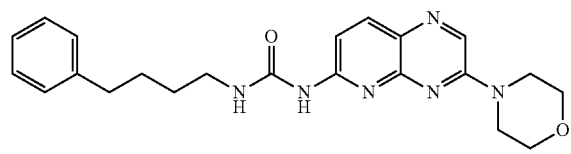 [SMILES: O=C(NCCCCc1ccccc1)Nc1ccc2ncc(N3CCOCC3)nc2n1]

Compound 177: 1-[3-(3,5-Dimethyl-1H-pyrazol-4-yl)-pyrido[2,3-b]pyrazin-6-yl]-3-((R)-1-methyl-4-phenyl-butyl)-urea

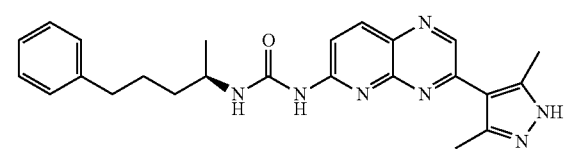 [SMILES: Cc1n[nH]c(C)c1-c1cnc2ccc(NC(=O)N[C@H](C)CCCc3ccccc3)nc2n1]

Compound 178: 1-[3-(3,4-Dimethoxy-phenyl)-pyrido[2,3-b]pyrazin-6-yl]-3-(4-phenyl-butyl)-urea

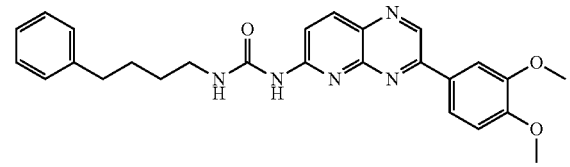 [SMILES: COc1ccc(-c2cnc3ccc(NC(=O)NCCCCc4ccccc4)nc3n2)cc1OC]

Compound 179: 1-[3-(2-Methoxy-phenyl)-pyrido[2,3-b]pyrazin-6-yl]-3-((R)-1-methyl-4-phenyl-butyl)-urea

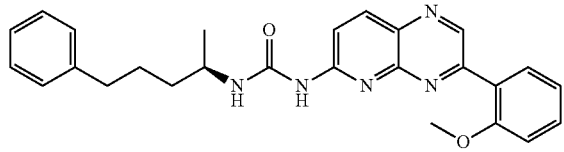 [SMILES: COc1ccccc1-c1cnc2ccc(NC(=O)N[C@H](C)CCCc3ccccc3)nc2n1]

Compound 180: 1-((R)-1-Methyl-4-phenyl-butyl)-3-[3-(1-methyl-1H-pyrazol-4-yl)-pyrido[2,3-b]pyrazin-6-yl]urea

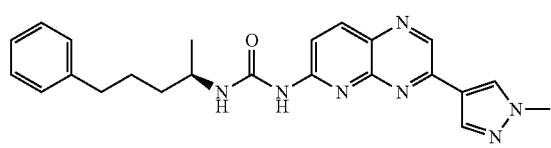 [SMILES: C[C@H](CCCc1ccccc1)NC(=O)Nc1ccc2ncc(-c3cnn(C)c3)nc2n1]

Compound 181: 1-[3-(3-Hydroxymethyl-phenyl)-pyrido[2,3-b]pyrazin-6-yl]-3-((R)-1-methyl-4-phenyl-butyl)-urea

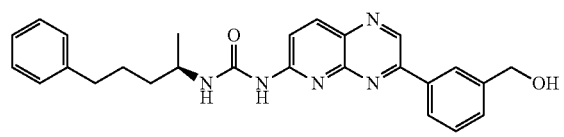 [SMILES: C[C@H](CCCc1ccccc1)NC(=O)Nc1ccc2ncc(-c3cccc(CO)c3)nc2n1]

Compound 182: 1-[3-(4-Hydroxymethyl-phenyl)-pyrido[2,3-b]pyrazin-6-yl]-3-(4-phenyl-butyl)-urea

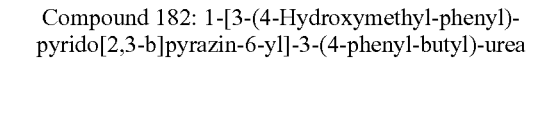

Compound 183: 1-[3-(2,4-Dimethoxy-phenyl)-pyrido[2,3-b]pyrazin-6-yl]-3-((R)-1-methyl-4-phenyl-butyl)-urea

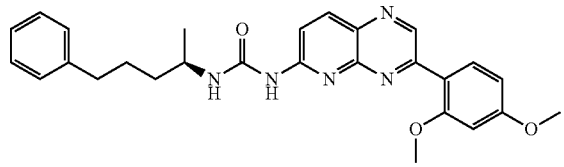 [SMILES: COc1ccc(-c2cnc3ccc(NC(=O)N[C@H](C)CCCc4ccccc4)nc3n2)c(OC)c1]

Compound 184: 1-(4-Phenyl-butyl)-3-(3-pyridin-4-yl-pyrido[2,3-b]pyrazin-6-yl)-urea

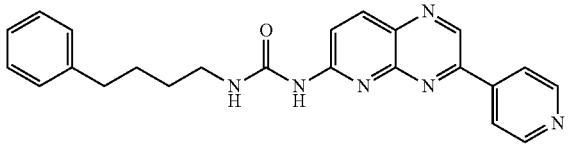 [SMILES: O=C(NCCCCc1ccccc1)Nc1ccc2ncc(-c3ccncc3)nc2n1]

Compound 185: 1-[3-(3-Fluoro-4-hydroxy-phenyl)-pyrido[2,3-b]pyrazin-6-yl]-3-((R)-1-methyl-4-phenyl-butyl)-urea

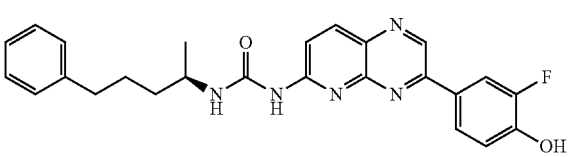 [SMILES: C[C@H](CCCc1ccccc1)NC(=O)Nc1ccc2ncc(-c3ccc(O)c(F)c3)nc2n1]

Compound 186: 1-[3-(3-Chloro-4-hydroxy-phenyl)-pyrido[2,3-b]pyrazin-6-yl]-3-(4-phenyl-butyl)-urea

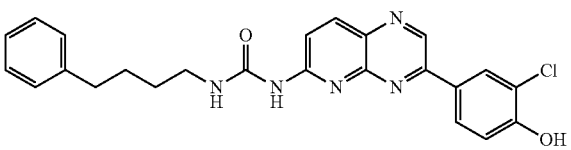 [SMILES: O=C(NCCCCc1ccccc1)Nc1ccc2ncc(-c3ccc(O)c(Cl)c3)nc2n1]

Compound 187: 1-[3-((S)-3-Methyl-morpholin-4-yl)-pyrido[2,3-b]pyrazin-6-yl]-3-((R)-1-methyl-4-phenyl-butyl)-urea

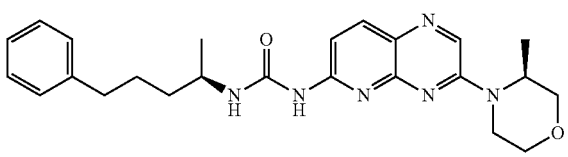 [SMILES: C[C@H](CCCc1ccccc1)NC(=O)Nc1ccc2ncc(N3CCOC[C@@H]3C)nc2n1]

Compound 188: 1-[3-(4-{2-[2-(2-Hydroxy-ethoxy)-ethoxy]-ethoxy}-phenyl)-pyrido[2,3-b]pyrazin-6-yl]-3-((R)-1-methyl-4-phenyl-butyl)-urea

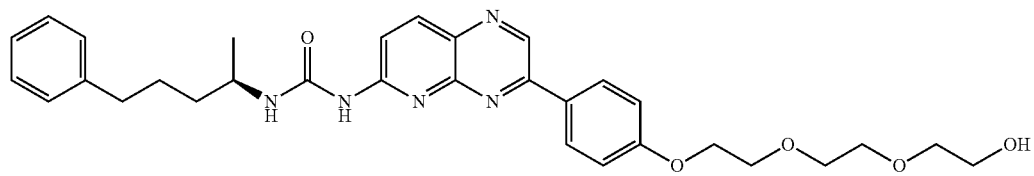 [SMILES: C[C@H](CCCc1ccccc1)NC(=O)Nc1ccc2ncc(-c3ccc(OCCOCCOCCO)cc3)nc2n1]

Compound 189: 1-{3-[1-(2-Hydroxy-ethyl)-1H-pyrazol-4-yl]-pyrido[2,3-b]pyrazin-6-yl}-3-(4-phenyl-butyl)-urea

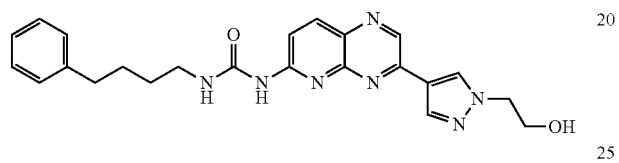

Compound 194: 2-Methoxy-4-{6-[3-(4-phenyl-butyl)-ureido]-pyrido[2,3-b]pyrazin-3-yl}-benzoic acid

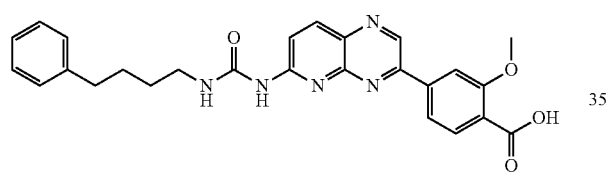

Compound 195: (S)-2-Amino-3-(4-{6-[3-((R)-1-methyl-4-phenyl-butyl)-ureido]-pyrido[2,3-b]pyrazin-3-yl}-phenyl)-propionic acid; hydrochloride

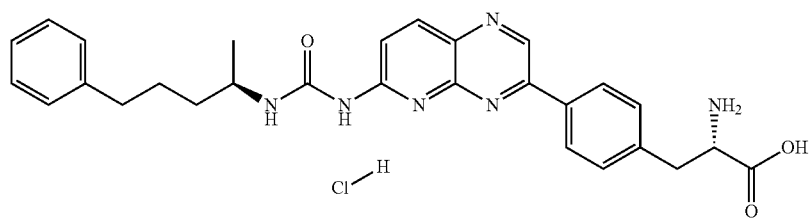 [SMILES: C[C@H](CCCc1ccccc1)NC(=O)Nc1ccc2ncc(-c3ccc(C[C@H](N)C(=O)O)cc3)nc2n1 ; Cl]

Compound 196: 3-{6-[3-((R)-1-Methyl-4-phenyl-butyl)-ureido]-pyrido[2,3-b]pyrazin-3-yl}-benzoic acid

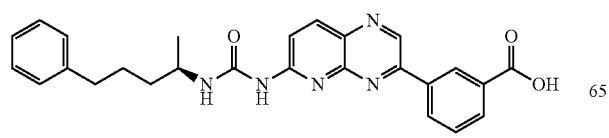

Compound 197: (S)-2-Amino-3-(4-{6-[3-(4-phenyl-butyl)-ureido]-pyrido[2,3-b]pyrazin-3-yl}-phenyl)-propionic acid

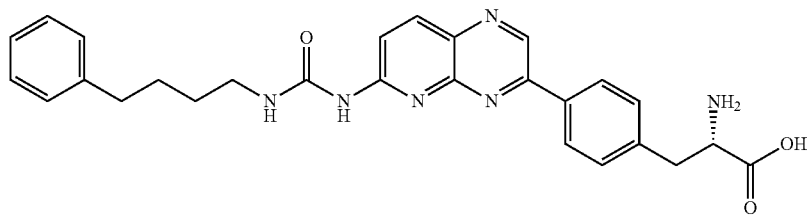 [SMILES: N[C@@H](Cc1ccc(-c2cnc3ccc(NC(=O)NCCCCc4ccccc4)nc3n2)cc1)C(=O)O]

Compound 198: 3-{6-[3-(4-Phenyl-butyl)-ureido]-pyrido[2,3-b]pyrazin-3-yl}-benzoic acid

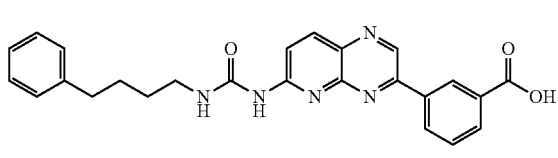 [SMILES: O=C(NCCCCc1ccccc1)Nc1ccc2ncc(-c3cccc(C(=O)O)c3)nc2n1]

Compound 199: 1-{3-[4-(2-Methoxy-ethoxy)-phenyl]-pyrido[2,3-b]pyrazin-6-yl}-3-(4-phenyl-butyl)-urea

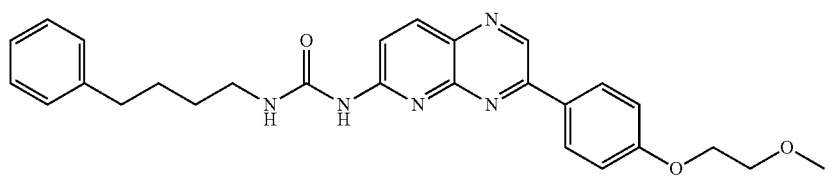 [SMILES: COCCOc1ccc(-c2cnc3ccc(NC(=O)NCCCCc4ccccc4)nc3n2)cc1]

Compound 200: rac 1-{3-[4-(2-Hydroxy-propoxy)-phenyl]-pyrido[2,3-b]pyrazin-6-yl}-3-(4-phenyl-butyl)-urea

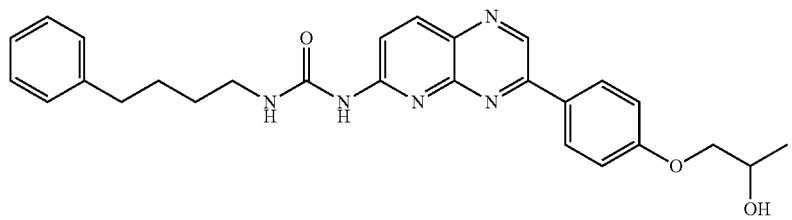 [SMILES: CC(O)COc1ccc(-c2cnc3ccc(NC(=O)NCCCCc4ccccc4)nc3n2)cc1]

Compound 201: 1-(3-{4-[2-(2-Hydroxy-ethoxy)-ethoxy]-phenyl}-pyrido[2,3-b]pyrazin-6-yl)-3-(4-phenyl-butyl)-urea

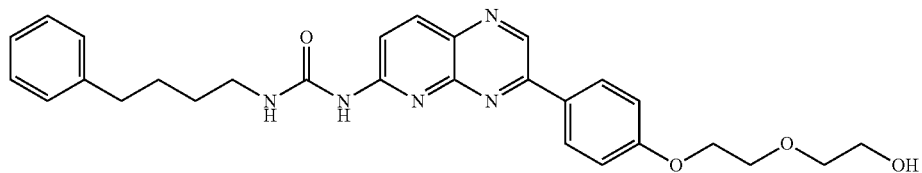 [SMILES: O=C(NCCCCc1ccccc1)Nc1ccc2ncc(-c3ccc(OCCOCCO)cc3)nc2n1]

Compound 202

1-{3-[4-(2-Morpholin-4-yl-ethoxy)-phenyl]-pyrido[2,3-b]pyrazin-6-yl}-3-(4-phenyl-butyl)-urea

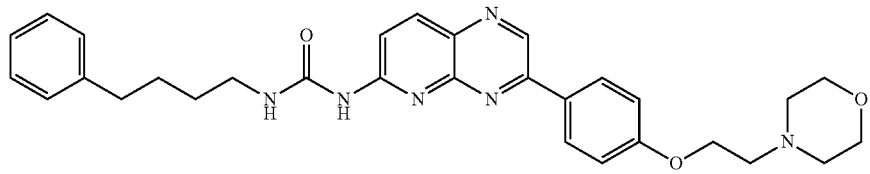 [SMILES: O=C(NCCCCc1ccccc1)Nc1ccc2ncc(-c3ccc(OCCN4CCOCC4)cc3)nc2n1]

Compound 203: 1-[3-(3-Methoxymethyl-phenyl)-pyrido[2,3-b]pyrazin-6-yl]-3-((R)-1-methyl-4-phenyl-butyl)-urea

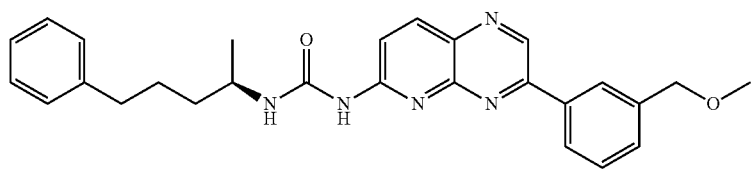 [SMILES: COCc1cccc(-c2cnc3ccc(NC(=O)N[C@H](C)CCCc4ccccc4)nc3n2)c1]

Compound 204: 1-{3-[3-(2-Methoxy-ethoxymethyl)-phenyl]-pyrido[2,3-b]pyrazin-6-yl}-3-((R)-1-methyl-4-phenyl-butyl)-urea

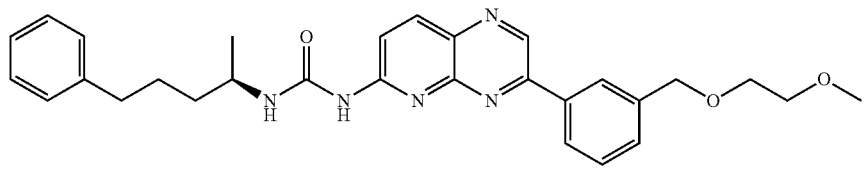 [SMILES: COCCOCc1cccc(-c2cnc3ccc(NC(=O)N[C@H](C)CCCc4ccccc4)nc3n2)c1]

Compound 205: 1-{3-[3-(2-Dimethylamino-ethoxymethyl)-phenyl]-pyrido[2,3-b]pyrazin-6-yl}-3-((R)-1-methyl-4-phenyl-butyl)-urea

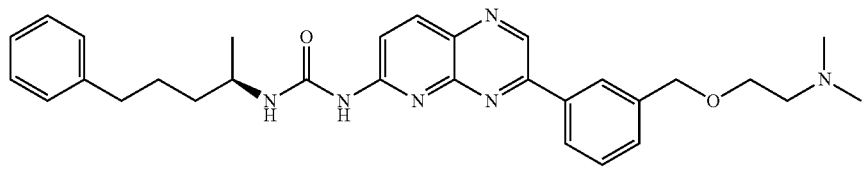 [SMILES: C[C@H](CCCc1ccccc1)NC(=O)Nc1ccc2ncc(-c3cccc(COCCN(C)C)c3)nc2n1]

Compound 206: Methanesulfonic acid 3-{6-[3-((R)-1-methyl-4-phenyl-butyl)-ureido]-pyrido[2,3-b]pyrazin-3-yl}-benzyl ester

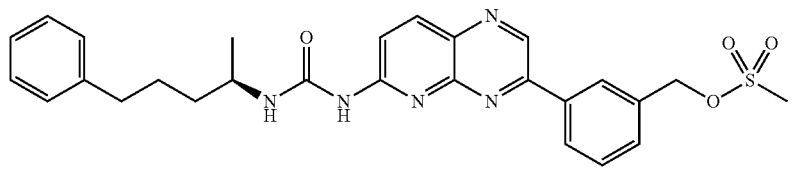 [SMILES: C[C@H](CCCc1ccccc1)NC(=O)Nc1ccc2ncc(-c3cccc(COS(C)(=O)=O)c3)nc2n1]

Compound 207: 1-((R)-1-Methyl-4-phenyl-butyl)-3-{3-[3-(2-morpholin-4-yl-ethoxymethyl)phenyl]pyrido[2,3-b]pyrazin-6-yl}-urea

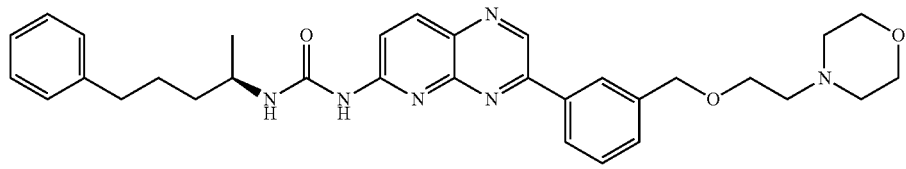 [SMILES: C[C@H](CCCc1ccccc1)NC(=O)Nc1ccc2ncc(-c3cccc(COCCN4CCOCC4)c3)nc2n1]

Compound 208: Ethyl-carbamic acid 3-{6-[3-((R)-1-methyl-4-phenyl-butyl)-ureido]-pyrido[2,3-b]pyrazin-3-yl}-benzyl ester

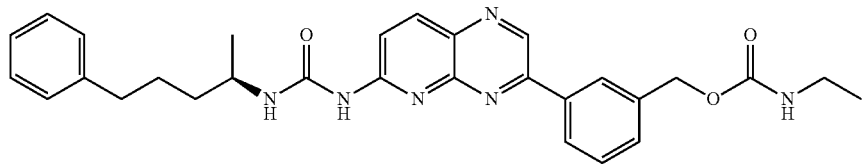 [SMILES: CCNC(=O)OCc1cccc(-c2cnc3ccc(NC(=O)N[C@H](C)CCCc4ccccc4)nc3n2)c1]

Compound 209: 1-((R)-1-Methyl-4-phenyl-butyl)-3-{3-[3-((2R,3R,4S,5S,6R)-3,4,5-trihydroxy-6-hydroxymethyl-tetrahydro-pyran-2-yloxymethyl)-phenyl]-pyrido[2,3-b]pyrazin-6-yl}-urea

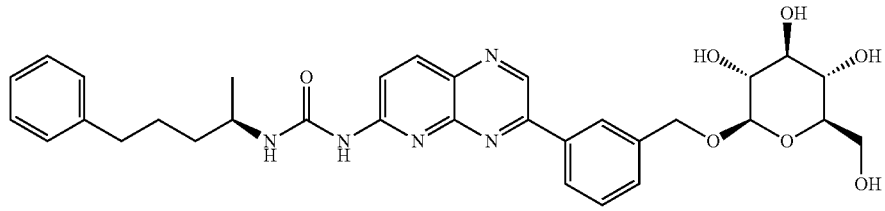 [SMILES: C[C@H](CCCc1ccccc1)NC(=O)Nc1ccc2ncc(-c3cccc(CO[C@@H]4O[C@H](CO)[C@@H](O)[C@H](O)[C@H]4O)c3)nc2n1]

which can be used for the production of a medicament for the treatment or prevention of physiological and/or pathophysiological states in mammals mediated by the ras-Raf-Mek-Erk signal transduction pathway.

In order to avoid ambiguities: when chemical structure and chemical name of the explicit compounds shown above erroneously do not match one another, the chemical structure shall unambiguously define the particular explicit compound.

The afore-mentioned generic compounds having the general formula (I) and preferred embodiments as well as the explicitly specified pyridopyrazine compounds 90 to 189, 194 to 209 are hereinafter designated jointly as "compounds according to the invention".

The expressions and terms specified to explain the compounds according to the invention having the general formula (I), the preferred embodiments and compounds 90 to 189, 194 to 209 basically have the following meanings unless specified otherwise in the description and the claims:

In the context of this invention, the expression "alkyl" encompasses acyclic saturated or unsaturated hydrocarbon radicals which may be branched or straight-chain and have 1 to 8 carbon atoms, i.e. $C_{1-8}$-alkanyls, $C_{2-8}$-alkenyls and $C_{2-8}$-alkynyls. Alkenyls have at least one C—C double bond and alkynyls at least one C—C triple bond. Alkynyls may additionally also have at least one C—C double bond. Preferred alkyl radicals are methyl, ethyl, n-propyl, 2-propyl, n-butyl, sec-butyl, tert-butyl, n-pentyl, iso-pentyl, neo-pentyl, n-hexyl, 2-hexyl, n-heptyl, n-octyl, n-nonyl, n-decyl, n-undecyl, n-dodecyl, ethylenyl (vinyl), ethynyl, propenyl (—CH$_2$CH═CH$_2$; —CH═CH—CH$_3$, —C(═CH$_2$)—CH$_3$), propynyl (—CH$_2$—C≡CH, —C≡C—CH$_3$), butenyl, butynyl, pentenyl, pentynyl, hexenyl, hexynyl, heptenyl, heptynyl, octenyl, octadienyl and octynyl.

For the purposes of this invention, the expression "cycloalkyl" means cyclic nonaromatic hydrocarbons having 1 to 3 rings with 3 to 20, preferably 3 to 12 carbon atoms, which may be saturated or unsaturated, more preferably ($C_3$-$C_8$)cycloalkyl. The cycloalkyl radical may also be part of a bi- or polycyclic system, where, for example, the cycloalkyl radical is fused to an aryl, heteroaryl or heterocyclyl radical as defined herein by any possible and desired ring member(s). The bonding to the compounds of the general formula (I) can be effected via any possible ring member of the cycloalkyl radical. Preferred cycloalkyl radicals are cyclopropyl, cyclobutyl, cyclopentyl, cyclohexyl, cycloheptyl, cyclooctyl, cyclodecyl, cyclohexenyl, cyclopentenyl and cyclooctadienyl.

The expression "heterocyclyl" represents a 3- to 14-membered, preferably 3-, 4-, 5-, 6-, 7- or 8-membered, cyclic organic radical which contains at least 1 heteroatom, optionally 2, 3, 4 or 5 heteroatoms, especially nitrogen, oxygen and/or sulphur, the heteroatoms being the same or different and the cyclic radical being saturated or unsaturated but not aromatic. The heterocyclyl radical may also be part of a bi- or polycyclic system, where, for example, the heterocyclyl radical is fused to an aryl, heteroaryl or cycloalkyl radical as defined herein by any possible and desired ring member(s). The bonding to the compounds of the general formula (I) can be effected via any possible ring member of the heterocyclyl radical. Preferred heterocyclyl radicals are tetrahydrofuryl, pyrrolidinyl, imidazolidinyl, thiazolidinyl, tetrahydropyranyl, piperidinyl, piperazinyl, morpholinyl, thiapyrrolidinyl, oxapiperazinyl, oxapiperidinyl and oxadiazolyl.

In the context of this invention, the expression "aryl" means aromatic hydrocarbons having 3 to 14 carbon atoms, preferably 5 to 14 carbon atoms, more preferably 6 to 14 carbon atoms. The aryl radical may also be part of a bi- or polycyclic system, where, for example, the aryl radical is fused to a heterocyclyl, heteroaryl or cycloalkyl radical as defined herein by any possible and desired ring member(s), for example to tetrahydrofuran, tetrahydrothiophene, pyrrolidine, imidazolidine, thiazolidine, tetrahydropyran, dihydropyran, piperidine, furan, thiophene, imidazole, thiazole, oxazole, isoxazole. The bonding to the compounds of the general formula (I) can be effected via any possible ring member of the aryl radical. Preferred aryl radicals are phenyl, biphenyl, naphthyl and anthracenyl, but likewise indanyl, indenyl or 1,2,3,4-tetrahydronaphthyl.

The expression "heteroaryl" represents a 5-, 6- or 7-membered cyclic aromatic radical which contains at least 1 heteroatom, if appropriate also 2, 3, 4 or 5 heteroatoms, especially nitrogen, oxygen and/or sulphur, the heteroatoms being the same or different. The number of nitrogen atoms is preferably 0 to 3, that of oxygen and sulphur atoms preferably 0 or 1. The heteroaryl radical may also be part of a bi- or polycyclic system, where, for example, the heteroaryl radical is fused to a heterocyclyl, aryl or cycloalkyl radical as defined herein by any possible and desired ring member(s). The bonding to the compounds of the general formula (I) can be effected via any possible ring member of the heteroaryl radical. Preferred heteroaryl radicals are pyrrolyl, furyl, thienyl, thiazolyl, isothiazolyl, oxazolyl, oxadiazolyl, isoxazolyl, pyrazolyl, imidazolyl, triazole, tetrazole, pyridinyl, pyrimidinyl, pyridazinyl, pyrazinyl, triazinyl, phthalazinyl, indolyl, indazolyl, indolizinyl, benzimidazolyl, quinolinyl, isoquinolinyl, quinoxalinyl, quinazolinyl, pteridinyl, carbazolyl, phenazinyl, phenoxazinyl, phenothiazinyl, and acridinyl.

For the purposes of the present invention, the expressions "alkyl-cycloalkyl", "cycloalkylalkyl", "alkyl-heterocyclyl", "heterocyclylalkyl", "alkyl-aryl", "arylalkyl", "alkyl-heteroaryl" and "heteroarylalkyl" mean that alkyl, cycloalkyl, heterocycl, aryl and heteroaryl are each as defined above, and the cycloalkyl, heterocyclyl, aryl and heteroaryl radical is bonded to the compounds of the general formula (I) via an alkyl radical, preferably $C_1$-$C_8$-alkyl radical, more preferably $C_1$-$C_5$-alkyl radical.

In connection with "alkyl", "cycloalkyl", "heterocyclyl", "aryl", "heteroaryl", alkyl-cycloalkyl", "alkyl-heterocyclyl", "alkyl-aryl" and "alkyl-heteroaryl" the term substituted is understood in the sense of this invention unless defined explicitly above in the description and the claims as the substitution of one or more hydrogen groups by F, Cl, Br, I, CN, $CF_3$, $NH_2$, NH-alkyl, NH-aryl, N(alkyl)$_2$, $NO_2$, SH, S-alkyl, $SO_2$-alkyl, OH, $OCHF_2$, $OCF_3$, OMe, OEt, O—CH2—CH2-OMe; O—CH2-CH2-OH; O—$CH_2$—$CH_2$—O—$CH_2$—$CH_2$—OMe; O—CH2-CH2-NMe$_2$; O—CH2-CH2-morpholinyl; O-Alkyl-aryl, O-aryl, —O—CH—O—; O—C(O)—NHEt; $OSO_2$Me, $OSO_3$H, OP(O)(OH)$_2$, CHO, $CO_2$H, $SO_3$H, alkyl, Alkyl-OH or 4-methyl-piperazin-1-ylmethyl. The substituents can be the same or different and the substitutions can take place in any arbitrary and possible position of the alkyl, cycloalkyl, heterocyclyl, aryl and heteroaryl group.

In the context of this invention, the expression "halogen" encompasses the halogen atoms fluorine, chlorine, bromine and iodine.

Multiply substituted groups are to be understood as those which are multiply, e.g. doubly, triply, substituted either at different or at the same atoms, for example, triply substituted at the same C atoms as in the case of $CF_3$, —$CH_2CF_3$ or at different positions as in the case of —CH(OH)—CH═CH—CHCl$_2$. The multiple substitution can take place with the same or different substituents.

Insofar as the compounds according to the invention have at least one centre of asymmetry, they can be present in the form of their racemates, in the form of the pure enantiomers and/or diastereomers or in the form of mixtures of these enantiomers and/or diastereomers. The mixtures can be present in any arbitrary mixture ratio of the stereoisomers.

Thus, for example, the compounds according to the invention which have one or a plurality of centres of chirality and which occur as their racemates can be separated into their optical isomers, that is enantiomers or diastereomers, by methods known per se. The separation can be performed by column separation at chiral phases or by recrystallisation from an optically active solvent or by using an optically active acid or base or by derivatisation with an optically active reagent, such as for example, an optically active alcohol and subsequent separation of the residue.

The inventive compounds may be present in the form of their double bond isomers as "pure" E or Z isomers, or in the form of mixtures of these double bond isomers.

As far as possible, the compounds according to the invention can be present in the form of tautomers.

If they possess a sufficiently basic group, such as for example, a primary, secondary or tertiary amine, the compounds according to the invention can be converted into their physiologically compatible salts using inorganic and organic acids. The pharmaceutically acceptable salts of the compounds according to the invention are preferably formed with hydrochloric acid, bromic acid, sulphuric acid, phosphoric acid, methane sulfonic acid, p-toluene sulfonic acid, carbonic acid, formic acid, acetic acid, trifluoroacetic acid, sulfoacetic acid, oxalic acid, malonic acid, maleic acid, succinic acid, tartaric acid, racemic acid, malic acid, embonic acid, mandelic acid, fumaric acid, lactic acid, citric acid, glutamic acid or asparaginic acid. The salts formed include, among others, hydrochloride, hydrobromide, sulfate, hydrogen sulfate, phosphate, methane sulfonate, tosylate, carbonate, hydrogen carbonate, formiate, acetate, triflate, sulfoacetate, oxalate, malonate, maleate, succinate, tartrate, malate, embonate, mandelate, fumarate, lactate, citrate, glutaminate and aspartate. The stoichiometry of the salts of the compounds according to the invention which are formed can be integer or non-integer multiples of one.

If they contain a sufficiently acidic group, such as the carboxy group, for example, the compounds according to the invention can be converted into their physiologically compatible salts using inorganic and organic bases. Possible inorganic bases are, for example, sodium hydroxide, potassium hydroxide, calcium hydroxide, possible organic bases are ethanol amine, diethanol amine, triethanol amine, cyclohexylamine, dibenzylethylene diamine and lysine. The stoichiometry of the salts of the compounds according to the invention which are formed can be integer or non-integer multiples of one.

Likewise preferred are solvates and in particular hydrates of the compounds according to the invention, which can be obtained, for example, by crystallisation from a solvent or from aqueous solution. In this context, one, two, three or an arbitrary number of solvate or water molecules can combine with the compounds according to the invention to form solvates and hydrates.

It is known that chemical substances form solids which are present in various states of order, which are designated as polymorphous forms or modifications. The various modifications of a polymorphous substance can differ strongly in respect of their physical properties. The compounds according to the invention can be present in various polymorphous forms, in which case certain modifications can be metastable.

The compounds according to the invention can likewise be present in the form of any prodrugs such as, for example, esters, carbonates, carbamates, ureas, amides or phosphates, wherein the actually biologically active form is only released by catabolism.

It is further known that chemical substances are converted to metabolites in the body which optionally can likewise induce the desired biological effect, possibly even in a more distinct form.

Corresponding prodrugs and metabolites of the compounds according to the invention should also be considered as pertaining to the invention.

It was now surprisingly and advantageously determined that the compounds according to the invention can act simultaneously or have a modulating or inhibiting effect on one or more signal transduction pathways or enzymes. In this context, it has been found that the compounds according to the invention can act or have a modulating or inhibiting effect with high selectivity.

The surprising advantageous effects of the compounds according to the invention allow multiple therapy approaches to be pursued in physiological and/or pathophysiological states or clinical pictures which are sensitive for the treatment or modulation of, or are mediated by, one or more signal transduction pathways.

It was further surprisingly and advantageously determined that the compounds according to the invention can also act with high selectivity or have a modulating or inhibiting effect on the ras-Raf-Mek-Erk signal transduction pathway or enzymes thereof and that the multiple mechanisms of action and therapy approaches described above can also be used with this signal pathway or enzymes comprising a pharmacologically active quantity of at least one compound selected from the group consisting of: "compound 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 137, 138, 139, 140, 141, 142, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 194, 195, 196, 197, 198, 199, 200, 201, 202, 203, 204, 205, 206, 207, 208 and/or compound 209" and optionally pharmaceutically compatible excipients and/or adjuvants are covered by the present invention.

The term "modulation" is understood according to the invention as follows: "activation, partial activation, inhibition, partial inhibition". In this case, it is within the specialist knowledge of the average person skilled in the art to measure and determine such activation, partial activation, inhibition, partial inhibition by means of the usual methods of measurement and determination. Thus, a partial activation can be measured and determined in relation to a complete activation; likewise, a partial inhibition in relation to a complete inhibition.

The terms "inhibiting, inhibition and/or retardation" are understood as follows according to the invention: "partial or complete inhibiting, inhibition and/or retardation". In this case, it is within the specialist knowledge of the average person skilled in the art to measure and determine such inhibiting, inhibition, and/or retardation by means of the usual methods of measurement and determination. Thus, a partial inhibiting, inhibition and/or retardation, for example, can be measured and determined in relation to a complete inhibiting, inhibition and/or retardation.

The terms "modulation" and "inhibiting, inhibition and/or retardation" in connection with "enzymes" and/or "kinases" within the scope of this invention relate both to the inactive form (enzymatically inactive) and/or active form (enzymatically active) of the respective enzyme and/or kinase. This means within the scope of this invention that the compound according to the invention can have a modulating effect on the inactive form, active form or both forms of the enzyme and/or kinase.

In a further aspect, the inventive object was surprisingly achieved by preparing the compounds according to the invention which can be used to produce a medicament for the treatment or prevention of physiological and/or pathophysiological states in mammals, wherein the treatment or prevention is effected by modulation of the ras-Raf-Mek-Erk signal transduction pathway.

In a further aspect, the inventive object was surprisingly achieved by preparing the compounds according to the invention which can be used to produce a medicament for the treatment or prevention of physiological and/or pathophysiological states in mammals, mediated by the ras-Raf-Mek-Erk signal transduction pathway.

In a further aspect, the inventive object was surprisingly achieved by preparing the compounds according to the invention which can be used to produce a medicament for the treatment or prevention of physiological and/or pathophysiological states in mammals, wherein the treatment or prevention is effected by modulation of the ras-Raf-Mek-Erk signal transduction pathway.

In a preferred embodiment, the compounds according to the invention are prepared for the uses described above, wherein the modulation of the ras-Raf-Mek-Erk signal transduction pathway is effected by modulation of one or more enzymes selected from the group consisting of: "tyrosine kinase, serine/threonine kinase, receptor tyrosine kinase, cytoplasmic tyrosine kinase, cytoplasmic serine/threonine kinase" and preferably selected from the group consisting of: "Erk, Erk1, Erk2".

In a further aspect, the inventive object was surprisingly achieved by preparing the compounds according to the invention according to the aspects, preferred embodiments and uses described above which can be used to produce a medicament for the treatment or prevention of physiological and/ or pathophysiological states in mammals, wherein the treatment or prevention is effected by modulation of one or more enzymes.

In a further preferred embodiment, the compounds according to the invention are prepared for the uses described above, wherein the modulation is an inhibition.

The compounds according to the invention can be administered within the scope of this invention to all known mammals, in particular, humans, for the treatment and/or prevention.

In another preferred embodiment, the compounds according to the invention are prepared for the uses described above, wherein the mammal is selected from the group consisting of: "human, domesticated animal, cattle, pet, beef cattle, cow, sheep, pig, goat, horse, pony, donkey, hinny, mule, hare, rabbit, cat, dog, guinea pig, hamster, rat, mouse" and is preferably a human.

The compounds according to the invention can be used within the scope of this invention for the treatment and/or prevention of all known physiological and/or pathophysiological states.

In a preferred embodiment, the compounds according to the invention are prepared for the uses described above, wherein the physiological and/or pathophysiological states are selected from the group consisting of: "malignant tumours, benign tumours, inflammatory diseases, inflammations, pain, rheumatic diseases, arthritic diseases, HIV infections, neurological or neurodegenerative diseases, rheumatism, arthritis, AIDS, ARC (AIDS related complex), Kaposi's sarcoma, tumours originating from the brain and/or nervous system and/or meninges, dementia, Alzheimer's disease, hyperproliferative diseases, psoriasis, endometriosis, scarring, benign prostatahyperplasia (BPH), diseases of the immune system, autoimmune diseases, immunodeficiency diseases, colon tumour, gastric tumour, intestinal tumour, pulmonary tumour, pancreatic tumour, ovarian tumour, prostatic tumour, leukaemia, melanoma, hepatic tumour, renal tumour, head tumour, throat tumour, glioma, breast tumour, uterine cancer, endometrial cancer, cervico-uterine carcinoma, brain tumour, adeno-acanthoma, cancer of the bladder, gastric tumour, colorectal tumour, oesophageal cancer, gynocological tumour, ovarian tumour, cancer of the thyroid, lymphoma, chronic leukaemia, acute leukaemia, restenosis, diabetes, diabetic nephropathy, fibrotic diseases, cystic fibrosis, malignant nephrosclerosis, thrombotic microangiopathy syndrome, organ transplant rejection, glomerulopathy, metabolilc diseases, solid/fixed tumours, rheumatic arthritis, diabetic retinopathy, asthma, allergies, allergic diseases, chronic obstructive pulmonary diseases, inflammatory bowel disease, fibrosis, atheriosclerosis, heart diseases, cardiovascular diseases, diseases of the myocardium, vascular diseases, angiogenetic diseases, kidney diseases, rhinitis, Grave's disease, focal ischaemia, cardiac failure, ischaemia, cardiac hypertrophia, renal failure, cardiac myocytic malfunction, high blood pressure, vasoconstriction, stroke, anaphylactic shock, platelet agglutination, skeletomuscular atrophy, obesity, overweight, glucosis homeostasis, congestive cardiac insufficiency, angina, heart attack, cardiac infarction, hyperglycaemia, hypoglycaemia, hypertension".

In a further aspect of the present invention, the inventive object was surprisingly achieved by preparing the compounds according to the aspects, preferred embodiments and uses described above, for use for the production of a medicament for the treatment or prevention of physiological and/or pathophysiological states in mammals, wherein the medicament comprises at least one further pharmacologically active substance.

In a further aspect of the present invention, the inventive object was surprisingly achieved by preparing the compounds according to the aspects, preferred embodiments and uses described above, for use for the production of a medicament for the treatment or prevention of physiological and/or pathophysiological states in mammals, wherein the medicament is administered with at least one further pharmacologically active substance before and/or during and/or after treatment.

In a further aspect of the present invention, the inventive object was surprisingly achieved by preparing the compounds according to the aspects, preferred embodiments and uses described above, for use for the production of a medicament for the treatment or prevention of physiological and/or pathophysiological states in mammals, wherein the medicament is administered before and/or during and/or after treatment with radiation therapy and/or surgery.

The compounds according to the invention can be administered within the scope of this invention with all known pharmacologically active substances in a combination therapy as described.

In a preferred embodiment, the compounds according to the invention are prepared for the uses described above, wherein the further pharmacologically active substance is selected from the group consisting of: "DNA topoisomerase I and/or II inhibitors, DNA intercalators, alkylating agents, microtubuli destabilisors, hormone and/or growth factor receptor agonists and/or antagonists, antibodies against growth factors and their receptors, kinase inhibitors, alkylphospholipids, antimetabolites".

In a preferred embodiment, the compounds according to the invention are prepared for the uses described above, wherein the further pharmacologically active substance is selected from the group consisting of: "asparaginase, bleomycin, carboplatin, carmustin, chlorambucil, cisplatin, colaspase, cyclophosphamide, cytarabine, dacarbazine, dactinomycin, daunorubicin, doxorubicin(adriamycin), epirubicin, etoposide, 5-fluorouracil, hexamethylmelamine, hydroxyurea, ifosfamide, irinotecan, leucovorin, lomustine, mechlorethamine, 6-mercaptopurine, mesna, methotrexate, mitomycin C, mitoxantrone, prednisolone, prednisone, procarbazine, raloxifene, streptozocin, tamoxifen, thioguanine, topotecan, vinblastine, vincristine, vindesine, aminoglutethimide, L-asparaginase, azathioprine, 5-azacytidine cladribine, busulfan, diethylstilbestrol, 2',2'-difluorodeoxycytidine, docetaxel, erythrohydroxynonyladenine, ethinylestradiol, 5-fluorodeoxyuridin, 5-fluorodeoxyuridin monophosphate, fludarabine phosphate, fluoxymesterone, flutamide, hydroxyprogesterone caproate, idarubicin, interferon, medroxyprogesterone acetate, megestrol acetate, melphalan, mitotane, paclitaxel, oxaliplatin, pentostatin, N-phosphonoacetyl-L-aspartate (PALA), plicamycin, semustine, teniposide, testosterone propionate, thiotepa, trimethylmelamine, uridine, vinorelbin, epothilone, gemcitabine, Taxotere, BCNU, CCNU, $DTIC_{1-5}$-fluorouracil, Herceptin, Avastin, Erbitux, Sorafenib, Gleevec, Iressa, Tarceva, rapamycin, perifosine, miltefosine, edelfosine, actinomycin D".

Oral administration can take place, for example, in solid form as tablet, capsule, gel capsule, dragee, granule or powder but also in the form of a potable solution. For oral administration, the new compounds according to the invention, as defined hereinbefore, can be combined with known physiologically compatible adjuvants and excipients usually used, such as gum Arabic, talc, starch, sugar such as, for example, mannite, methyl cellulose, lactose, gelatine, surfactants, magnesium stearate, cyclodextrin, aqueous or non-aqueous excipients, diluents, dispersants, emulsifiers, lubricants, preservatives and flavourings (e.g. ether oils). The compounds according to the invention can also be dispersed in a microparticle, e.g. nanoparticle composition.

Non-oral administration can be effected, for example, by intravenous, subcutaneous or intramuscular injection of sterile aqueous or oily solutions, suspensions or emulsions, by means of implants or by ointments, creams or suppositories. Optionally, administration can be effected as a retard form. Implants can contain inert materials, e.g. biologically degradable polymers or synthetic silicones such as, for example, silicone rubber. Intravaginal administration can be effected by means of vaginal rings, for example. Intrauterine administration can take place, for example, by means of diaphragms or other suitable intrauterine devices. In addition, transdermal administration can be provided, in particular by means of a formulation suitable for this purpose and/or suitable means such as plasters, for example.

As has already been explained, the new compounds according to the invention can also be combined with further pharmaceutically active substances. Within the framework of a combination therapy, the individual active constituents cam be administered simultaneously or separately and either by the same pathway (e.g. oral) or by separate pathways (e.g. oral and as injection). They can be present or administered in the same or different quantities in a unit dose. A certain dosage regime can be applied insofar as this seems appropriate. In this way, a plurality of the new compounds according to the invention can be combined with one another.

The dosage can vary according to the type of indication, the severity of the disease, the type of administration, the age, sex, body weight and sensitivity of the subject to be treated over a wide range. It is within the capabilities of a person skilled in the art to determine a "pharmacologically effective quantity" of the combined pharmaceutical composition. The administration can be made in a single dose or a plurality of separate doses.

A suitable unit dose is 0.001 mg to 100 mg of the active substance, i.e. at least one compound according to the invention and optionally a further pharmaceutically active substance, per kg body weight of a patient.

In a further aspect of the present invention, accordingly pharmaceutical compositions comprising a pharmacologically active quantity of at least one compound selected from the group consisting of: "compound 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 137, 138, 139, 140, 141, 142, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 194, 195, 196, 197, 198, 199, 200, 201, 202, 203, 204, 205, 206, 207, 208 and/or compound 209" and optionally pharmaceutically compatible excipients and/or adjuvants are covered by the present invention.

Preferred and particularly preferred pharmaceutical compositions are those which comprise at least one of the aforesaid preferred compounds according to the invention. Pharmaceutical compositions according to the present invention can also contain, in addition to at least one compound according to the invention, as defined previously, at least one further pharmaceutically active substance, as has been described in detail hereinbefore.

The pharmaceutical compositions according to the invention contain at least one of the new compounds according to the invention, as defined hereinbefore, in a pharmacologically active quantity, preferably in a unit dose, e.g. the aforesaid unit dose and preferably in an administration form which allows oral administration.

With regard to pharmaceutical compositions comprising compounds according to the invention and with regard to the use of the compounds according to the invention as medicaments, reference is made to the statements made in connection with the use of the new compounds according to the invention themselves with regard to the possibilities for usage and administration.

In a further aspect of the present invention, the inventive object was surprisingly solved by preparing a kit comprising a pharmacologically active quantity of at least one preferred compound according to the invention as presented above and a pharmacologically active quantity of at least one further pharmacologically active substance as defined hereinbefore.

The naming of the compounds according to the invention having the general formula (I) together with preferred exemplary embodiments and in particular compounds 90 to 189, 194 to 209 was made using AutoNom 2000-Software (ISIS™/Draw 2.5; MDL).

General Synthetic Regulations for the Compounds According to the Invention

The procedures for manufacturing substituted pyrido[2,3-b]pyrazine according to the invention are explained below.

The compounds according to the invention can be obtained according to the corresponding procedures known to the person skilled in the art. In addition, refer to patent specifications WO 2004/104002, WO 2004/104003, WO2007/054556 and WO 2008/138878 or to the corresponding methods known in the literature to manufacture the compounds in accordance with the invention. In order to manufacture the initial compounds, intermediate compounds and the pyridopyrazine according to the invention, refer amongst other things, to the primary literature below, the content of which is herewith to become an integral part of the disclosure of the present filing application:

1) Houben-Weyl, Methods of Organic Chemistry, Volume 4/1a, pp. 343-350

2) Houben-Weyl, Methods of Organic Chemistry, 4th edition, Volume E 7b (Part 2), p. 579; Degussa GB 1184848 (1970); p. Seko, et al. EP 735025 (1996)

3) D. Catarzi, et al.; J. Med. Chem. 1996, 1330-1336; J. K. Seydel, et al.; J. Med. Chem. 1994, 3016-3022

4) Houben-Weyl, Methods of Organic Chemistry, Volume E 9c, pp. 231-235

5) Houben-Weyl/Science of Synthesis, Volume 16, p. 1269

6) C. L. Leese, H. N. Rydon J. Chem. Soc. 1955, 303-309; T. S. Osdene, G. M. Timmis J. Chem. Soc. 1955, 2033-2035

7) W. He, et al. Bioorg. Med. Chem. Lett. 2003, 13, 3097-3100

8) M. S. A. El-Gaby, et al. Indian J. Chem. Sect. B 2001, 40, 195-200; M. R. Myers, et al. Bioorg. Med. Chem. Lett. 2003, 13, 3091-3096; A. R. Renslo, et al. J. Amer. Chem. Soc. 1999, 121, 7459-7460; C. O. Okafor, et al. J. Heterocyclic Chem. 1983, 20, 199-203; C. R. Hopkins, et al. Tet. Lett. 2004, 45, 8631-8633

9) J. Yin, et al. Org. Lett. 2002, 4, 3481-3484; O. A. El-Sayed, et al. Arch. Pharm. 2002, 335, 403-410; C. Temple, et al. J. Med. Chem. 1992, 35, 988-993

10) A. M. Thompson, et al. *J. Med. Chem.* 2000, 43, 4200-4211; N. A. Dales, et al. *Org. Lett.* 2001, 2313-2316; G. Dannhardt, et al. *Arch. Pharm.* 2000, 267-274; G. S. Poindexter, et al. *Bioorg. Med. Chem.* 2004, 12, 507-521; J.-M. Receveur, et al. *Bioorg. Med. Chem. Lett.* 2004, 14, 5075-5080

11) G. Heinisch, et al. *Arch. Pharm.* 1997, 207-210; K. Matsuno, et al. *J. Med. Chem.* 2002, 45, 4513-4523; A. M. Papini, et al. *J. Med. Chem.* 2004, 47, 5224-5229

12) L. Mao, et al. *Synthesis* 2004, 15, 2535-2539; M. Darabantu, et al. *Tetrahedron* 2005, 61, 2897-2905; E. Ford, et al. *Tet. Lett.* 2000, 41, 3197-3198; T. Shiota, et al. *J. Org. Chem.* 1999, 64, 453-457

13) J. F. Miravet, et al. *Org. Lett.* 2005, 7, 4791-4794; A. L. Castelhano, et al. *Bioorg. Med. Chem. Lett.* 2005, 15, 1501-1504.

14) J. W. Huffmann, et al. *Bioorg. Med. Chem.* 2006, 14, 247-262; T. Liu, et al. *Org. & Biomolecular Chem.* 2005, 3, 1525-1533

The invention will be explained in detail with reference to the following examples without being restricted to these examples.

EXAMPLES

Compound 90

1-[3-(4-{2-[2-(2-Hydroxy-ethoxy)-ethoxy]-ethoxy}-phenyl)-pyrido[2,3-b]pyrazin-6-yl]-3-(4-phenyl-butyl)-urea

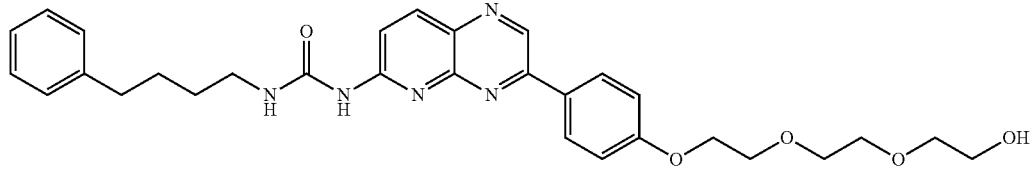 [SMILES: O=C(NCCCCc1ccccc1)Nc1ccc2ncc(-c3ccc(OCCOCCOCCO)cc3)nc2n1]

$^1$H-NMR (DMSO-d$_6$): δ=10.08 (s, 1H), 9.41 (s, 1H), 9.33 (s, 1H), 8.30 (m, 3H), 7.59 (d, 1H), 7.22 (m, 5H), 7.14 (m, 3H), 4.57 (m, 1H), 4.21 (m, 2H), 3.80 (m, 2H), 3.62 (m, 2H), 3.56 (m, 2H), 3.50 (m, 2H), 3.44 (m, 2H), 3.34 (m, 2H), 2.68 (m, 2H), 1.75 (m, 2H), 1.60 (m, 2H) ppm mp: 142° C.

Compound 91

1-[3-(3,5-Dimethyl-1H-pyrazol-4-yl)-pyrido[2,3-b]pyrazin-6-yl]-3-(4-phenyl-butyl)-urea

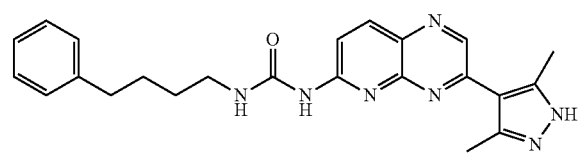 [SMILES: Cc1n[nH]c(C)c1-c1cnc2ccc(NC(=O)NCCCCc3ccccc3)nc2n1]

$^1$H-NMR (DMSO-d$_6$): δ=12.61 (s, 1H), 9.99 (s, 1H), 9.18 (s, 1H), 8.90 (m, 3H), 8.28 (d, 1H), 7.61 (d, 1H), 7.20 (m, 4H), 7.13 (m, 1H), 3.12 (m, 2H), 2.64 (m, 2H), 2.50 (m, 6H), 1.73 (m, 2H), 1.58 (m, 2H), ppm mp: 299-300° C.

Compound 92

1-(4-Phenyl-butyl)-3-[3-(2,3,4-trimethoxy-phenyl)-pyrido[2,3-b]pyrazin-6-yl]-urea

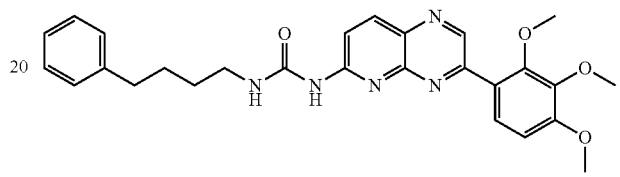

$^1$H-NMR (DMSO-d$_6$): δ=10.10 (s, 1H), 9.32 (s, 1H), 9.11 (s, 1H), 8.35 (d, 1H), 7.62 (m, 2H), 7.20 (m, 4H), 7.12 (m, 1H), 6.99 (d, 1H), 3.89 (s, 3H), 3.84 (s, 3H), 3.82 (s, 3H), 3.33 (m, 2H), 2.64 (m, 2H), 1.71 (m, 2H), 1.58 (m, 2H) ppm mp: 135-138° C.

Compound 93

1-[3-(4-Methyl-piperazin-1-yl)-pyrido[2,3-b]pyrazin-6-yl]-3-(4-phenyl-butyl)-urea

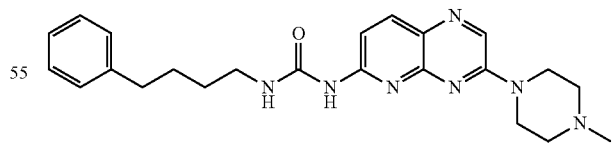

$^1$H-NMR (DMSO-d$_6$): δ=9.73 (s, 1H), 9.39 (s, 1H), 9.11 (s, 1H), 8.63 (s, 1H), 8.04 (d, 1H), 7.21 (m, 6H), 3.75 (m, 4H), 3.28 (m, 2H), 2.64 (m, 2H), 2.39 (m, 4H), 2.22 (s, 3H), 1.73 (m, 2H), 1.54 (m, 2H) ppm mp: 181-183° C.

Compound 94

1-[3-(3H-Benzoimidazol-5-yl)-pyrido[2,3-b]pyrazin-6-yl]-3-(4-phenyl-butyl)-urea

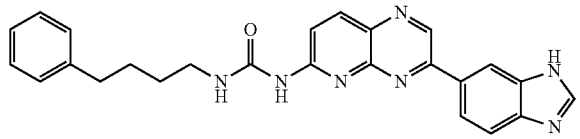 [SMILES: O=C(NCCCCc1ccccc1)Nc1ccc2ncc(-c3ccc4nc[nH]c4c3)nc2n1]

$^1$H-NMR (DMSO-d$_6$□□): □=12.72 (m, 1H), 10.08 (s, 1H), 9.52 (s, 1H), 9.35 (s, 1H), 8.60 (m, 3H), 8.36 (m, 2H), 8.23 (bs, 1H), 7.74 (bs, 1H), 7.62 (m, 1H), 7.20 (m, 5H), 3.35 (m, 2H), 2.67 (m, 2H), 1.76 (m, 2H), 1.61 (m, 2H) ppm mp: 226° C.

Compound 95

1-[3-(3-Amino-phenyl)-pyrido[2,3-b]pyrazin-6-yl]-3-(4-phenyl-butyl)-urea

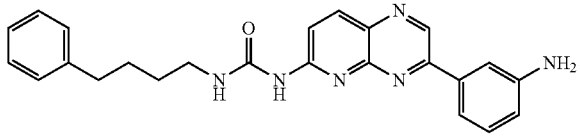 [SMILES: Nc1cccc(-c2cnc3ccc(NC(=O)NCCCCc4ccccc4)nc3n2)c1]

$^1$H-NMR (DMSO-d$_6$□□): □==10.07 (s, 1H), 9.28 (s, 1H), 9.22 (s, 1H), 8.34 (d, 1H), 7.65 (d, 1H), 7.51 (m, 1H), 7.43 (d, 1H), 7.22 (m, 5H), 7.13 (m, 1H), 6.77 (m, 1H), 5.33 (s, 2H), 3.33 (m, 2H), 2.66 (m, 2H), 1.71 (m, 2H), 1.59 (m, 2H) ppm mp: 200-203° C.

Compound 96

1-(4-Phenyl-butyl)-3-(3-piperazin-1-yl-pyrido[2,3-b]pyrazin-6-yl)-urea; hydrochloride

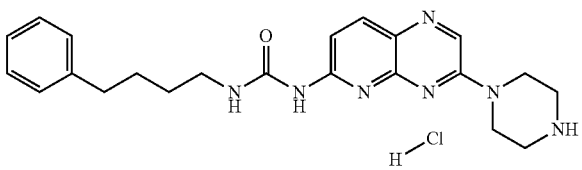

$^1$H-NMR (DMSO-d$_6$□□): □=9.79 (m, 1H), 9.26 (s, 1H), 8.93 (bs, 1H), 8.68 (m, 1H), 8.09 (m, 1H), 7.23 (m, 6H), 3.99 (m, 4H), 3.29 (m, 6H), 2.64 (m, 2H), 1.70 (m, 2H), 1.55 (m, 2H) ppm mp: 209-211° C.

Compound 97

1-[3-(1-Methyl-1H-pyrazol-4-yl)-pyrido[2,3-b]pyrazin-6-yl]-3-(4-p-tolyl-butyl)-urea

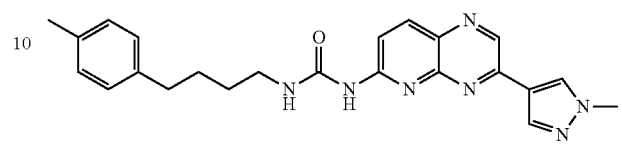

$^1$H-NMR (DMSO-d$_6$□□): □=9.79 (m, 1H), 10.00 (s, 1H), 9.24 (bs, 1H), 9.15 (s, 1H), 8.56 (s, 1H), 8.26 (m, 2H), 7.54 (m, 2H), 7.10 (d, 2H), 7.02 (d, 2H), 3.95 (s, 3H), 3.34 (m, 2H), 2.24 (s, 3H), 1.70 (m, 2H), 1.55 (m, 2H) ppm mp: 202-204° C.

Compound 98

1-[3-(3,4-Dimethoxy-phenyl)-pyrido[2,3-b]pyrazin-6-yl]-3-((R)-1-methyl-4-phenyl-butyl)-urea

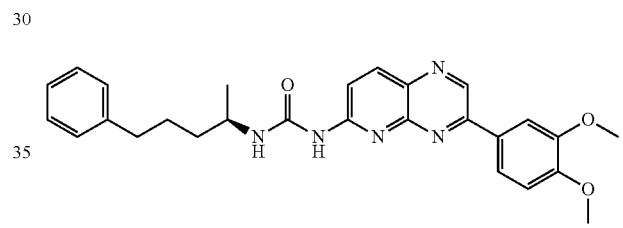

$^1$H-NMR (DMSO-d$_6$□□): □=10.01 (s, 1H), 9.46 (s, 1H), 9.19 (s, 1H), 8.33 (d, 1H), 7.95 (m, 2H), 7.65 (d, 1H), 7.16 (m, 6H), 3.87 (m, 7H), 2.64 (m, 2H), 1.74 (m, 2H), 1.59 (m, 2H), 1.22 (d, 3H) ppm mp: 195-197° C.

Compound 99

1-[4-(4-Fluoro-phenyl)-butyl]-3-[3-(1-methyl-1H-pyrazol-4-yl)-pyrido[2,3-b]pyrazin-6-yl]-urea

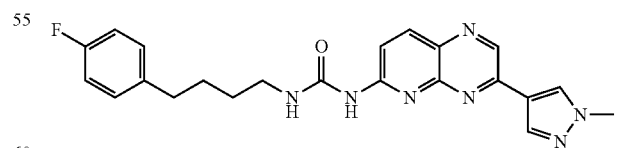

$^1$H-NMR (DMSO-d$_6$□□): □=10.03 (s, 1H), 9.24 (s, 1H), 9.17 (s, 1H), 8.25 (m, 2H), 7.55 (m, 1H), 7.25 (m, 2H), 7.03 (m, 2H), 3.98 (s, 3H), 2.69 (m, 2H), 1.74 (m, 2H), 1.59 (m, 2H) ppm mp: 197-200° C.

Compound 100

1-(4-Methyl-4-phenyl-pentyl)-3-[3-(1-propyl-1H-pyrazol-4-yl)-pyrido[2,3-b]pyrazin-6-yl]-urea

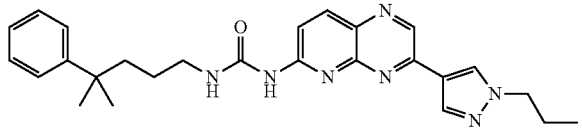 [SMILES: CCCn1cc(-c2cnc3ccc(NC(=O)NCCCC(C)(C)c4ccccc4)nc3n2)cn1]

$^1$H-NMR (DMSO-d$_6$): δ=9.97 (s, 1H), 9.19 (s, 1H), 9.16 (s, 1H), 8.61 (s, 1H), 8.27 (m, 2H), 7.52 (m, 1H), 7.38 (m, 2H), 7.24 (m, 2H), 7.12 (m, 1H), 4.16 (m, 2H), 3.19 (m, 2H), 1.68 (m, 2H), 1.76 (m, 2H), 1.31 (m, 6H), 0.87 (m, 3H) ppm mp: 205-207° C.

Compound 101

1-[3-(2,4-Dimethoxy-phenyl)-pyrido[2,3-b]pyrazin-6-yl]-3-(4-phenyl-butyl)-urea

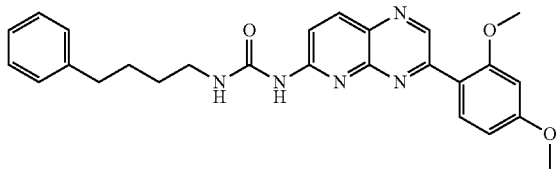 [SMILES: COc1ccc(-c2cnc3ccc(NC(=O)NCCCCc4ccccc4)nc3n2)c(OC)c1]

$^1$H-NMR (DMSO-d$_6$): δ=10.05 (s, 1H), 9.31 (s, 1H), 9.21 (s, 1H), 8.32 (s, 1H), 7.85 (m, 1H), 7.60 (m, 1H), 7.21 (m, 4H), 7.13 (m, 1H), 6.78 (s, 1H), 6.70 (m, 1H), 3.93 (s, 3H), 3.87 (s, 3H), 3.33 (m, 2H), 2.65 (m, 2H), 1.72 (m, 2H), 1.58 (m, 2H) ppm mp: 200-203° C.

Compound 102

1-[3-(2-Ethoxy-phenyl)-pyrido[2,3-b]pyrazin-6-yl]-3-(4-phenyl-butyl)-urea

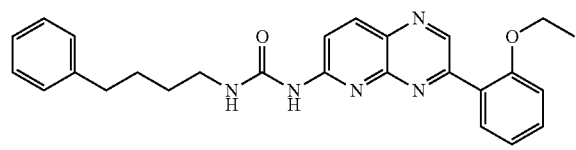 [SMILES: CCOc1ccccc1-c1cnc2ccc(NC(=O)NCCCCc3ccccc3)nc2n1]

$^1$H-NMR (DMSO-d$_6$): δ=10.09 (s, 1H), 9.29 (s, 1H), 9.26 (s, 1H), 8.36 (s, 1H), 7.84 (m, 1H), 7.65 (m, 1H), 7.53 (m, 1H), 7.25 (m, 1H), 7.19 (m, 4H), 7.12 (m, 1H), 4.20 (m, 2H), 2.64 (m, 2H), 1.72 (m, 2H), 1.58 (m, 2H), 1.36 (m, 3H) ppm mp: 173-175° C.

Compound 103

1-[3-(3,5-Dichloro-4-hydroxy-phenyl)-pyrido[2,3-b]pyrazin-6-yl]-3-(4-phenyl-butyl)-urea

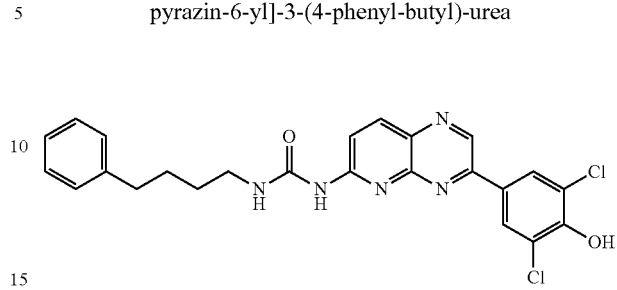

$^1$H-NMR (DMSO-d$_6$): δ=10.87 (s, 1H), 10.12 (s, 1H), 9.47 (s, 1H), 9.35 (s, 1H), 8.36 (m, 3H), 7.62 (m, 1H), 7.21 (m, 5H), 7.11 (m, 1H), 2.70 (m, 2H), 1.78 (m, 2H), 1.59 (m, 2H) ppm mp: 271-273° C.

Compound 104

1-[3-(3-Hydroxy-phenyl)-pyrido[2,3-b]pyrazin-6-yl]-3-(4-phenyl-butyl)-urea

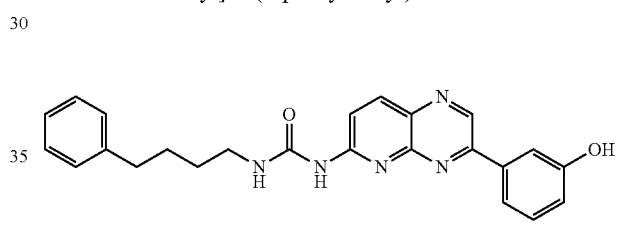

$^1$H-NMR (DMSO-d$_6$): δ=10.10 (s, 1H), 9.75 (s, 1H), 9.36 (s, 1H), 9.25 (s, 1H), 8.36 (m, 1H), 7.73 (m, 2H), 7.65 (m, 1H), 7.38 (m, 1H), 7.21 (m, 4H), 7.12 (m, 1H), 6.989 (m, 1H), 3.34 (m, 2H), 2.67 (m, 2H), 1.73 (m, 2H), 1.59 (m, 2H) ppm mp: 226-228° C.

Compound 105

1-(4-Phenyl-butyl)-3-[3-(2H-pyrazol-3-yl)-pyrido[2,3-b]pyrazin-6-yl]-urea

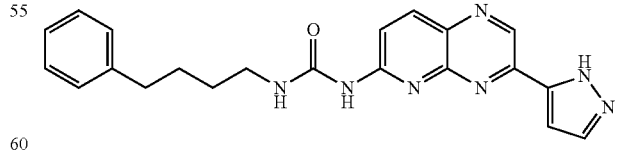

$^1$H-NMR (DMSO-d$_6$): δ=13.44 (s, 1H), 10.07 (s, 1H), 9.38 (s, 1H), 9.27 (s, 1H), 8.33 (m, 1H), 7.95 (m, 1H), 7.62 (m, 1H), 7.24 (m, 4H), 7.16 (m, 1H), 6.97 (m, 1H), 3.33 (m, 2H), 2.67 (m, 2H), 1.73 (m, 2H), 1.60 (m, 2H) ppm mp: 280° C. (dec.)

Compound 106

1-[3-(4-Hydroxy-2-methyl-phenyl)-pyrido[2,3-b]pyrazin-6-yl]-3-(4-phenyl-butyl)-urea

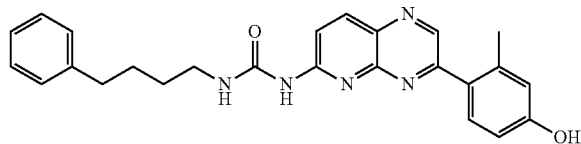 [SMILES: Cc1cc(O)ccc1-c1cnc2ccc(NC(=O)NCCCCc3ccccc3)nc2n1]

$^1$H-NMR (DMSO-d$_6$): δ=10.10 (s, 1H), 9.80 (s, 1H), 9.31 (s, 1H), 8.95 (s, 1H), 8.35 (m, 1H), 7.62 (m, 1H), 7.52 (m, 1H), 7.18 (m, 4H), 7.12 (m, 1H), 6.78 (s, 1H), 2.63 (m, 2H), 2.41 (s, 3H), 1.70 (m, 2H), 1.56 (m, 2H) ppm mp: 207-210° C.

Compound 107

Acetic acid 4-{6-[3-(4-phenyl-butyl)-ureido]-pyrido[2,3-b]pyrazin-3-yl}-phenyl ester

$^1$H-NMR (DMSO-d$_6$): δ=10.13 (s, 1H), 9.45 (s, 1H), 9.31 (s, 1H), 8.36 (m, 3H), 7.65 (m, 1H), 7.35 (d, 2H), 7.21 (m, 4H), 7.12 (m, 1H), 3.34 (m, 2H), 2.67 (m, 2H), 2.33 (s, 3H), 1.75 (m, 2H), 1.60 (m, 2H) ppm mp: 220° C.

Compound 108

1-[3-(1-Ethyl-1H-pyrazol-4-yl)-pyrido[2,3-b]pyrazin-6-yl]-3-(4-phenyl-butyl)-urea

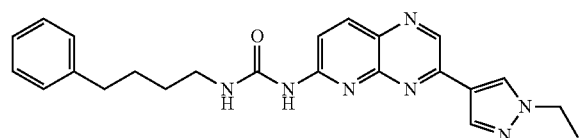

$^1$H-NMR (DMSO-d$_6$): δ=10.01 (s, 1H), 9.26 (s, 1H), 9.16 (s, 1H), 8.62 (s, 1H), 8.26 (m, 2H), 7.55 (m, 1H), 7.23 (m, 4H), 7.14 (m, 1H), 4.23 (m, 2H), 3.33 (m, 2H), 2.68 (s, 3H), 1.73 (m, 2H), 1.60 (m, 2H), 1.44 (t, 3H) ppm mp: 207-208° C.

Compound 109

1-[3-(3-Bromo-4-hydroxy-phenyl)-pyrido[2,3-b]pyrazin-6-yl]-3-(4-phenyl-butyl)-urea

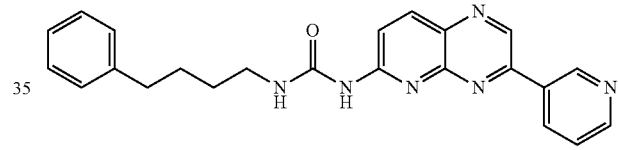

$^1$H-NMR (DMSO-d$_6$): δ=10.95 (s, 1H), 10.08 (s, 1H), 9.40 (s, 1H), 9.35 (s, 1H), 8.51 (m, 1H), 8.32 (m, 1H), 8.20 (m, 1H), 7.59 (m, 1H), 7.22 (m, 4H), 7.13 (m, 2H), 3.33 (m, 2H), 2.70 (m, 2H), 1.77 (m, 2H), 1.59 (m, 2H) ppm mp: 238-241° C.

Compound 110

1-(4-Phenyl-butyl)-3-(3-pyridin-3-yl-pyrido[2,3-b]pyrazin-6-yl)-urea

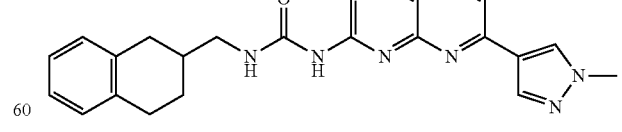

$^1$H-NMR (DMSO-d$_6$): δ=10.17 (s, 1H), 9.52 (s, 1H), 9.49 (m, 1H), 9.27 (s, 1H), 8.76 (m, 1H), 8.64 (m, 1H), 8.39 (m, 1H), 7.68 (m, 1H), 7.61 (m, 1H), 7.21 (m, 4H), 7.12 (m, 1H), 3.34 (m, 2H), 2.67 (m, 2H), 1.74 (m, 2H), 1.60 (m, 2H) ppm

Compound 111

1-[3-(1-Methyl-1H-pyrazol-4-yl)-pyrido[2,3-b]pyrazin-6-yl]-3-(1,2,3,4-tetrahydro-naphthalen-2-ylmethyl)-urea $^1$H-NMR (DMSO-d$_6$): δ=10.08 (s, 1H), 9.60 (s, 1H), 9.15 (s, 1H), 7.52 (s, 1H), 8.27 (d, 1H), 8.23 (s, 1H), 7.53 (d, 1H), 7.09 (m, 4H), 3.95 (s, 3H), 3.36 (m, 2H), 2.94 (m, 1H), 2.85 (m, 2H), 2.62 (m, 1H), 2.03 (m, 2H), 1.55 (m, 1H) ppm mp: 230-233° C.

Compound 112

1-[3-(2,3-Dimethoxy-phenyl)-pyrido[2,3-b]pyrazin-6-yl]-3-((R)-1-methyl-4-phenyl-butyl)-urea

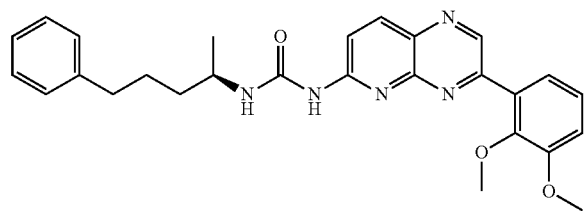 [SMILES: COc1cccc(-c2cnc3ccc(NC(=O)N[C@H](C)CCCc4ccccc4)nc3n2)c1OC]

$^1$H-NMR (DMSO-d$_6$□□): □=10.04 (s, 1H), 9.22 (s, 1H), 9.10 (s, 1H), 7.52 (s, 1H), 8.37 (d, 1H), 7.68 (s, 1H), 7.37 (m, 1H), 7.26 (m, 2H), 7.17 (m, 4H), 7.11 (m, 1H), 3.90 (s, 3H), 3.85 (m, 1H), 3.77 (s, 3H), 2.61 (m, 2H), 1.71 (m, 2H), 1.54 (m, 2H), 1.18 (d, 3H) ppm mp: 150-153° C.

Compound 113

1-[3-(5-Methyl-1-phenyl-1H-pyrazol-4-yl)-pyrido[2,3-b]pyrazin-6-yl]-3-(4-phenyl-butyl)-urea

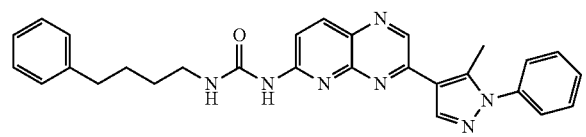 [SMILES: Cc1c(-c2cnc3ccc(NC(=O)NCCCCc4ccccc4)nc3n2)cnn1-c1ccccc1]

$^1$H-NMR (DMSO-d$_6$□□): □=10.11 (s, 1H), 9.25 (s, 2H), 8.58 (s, 1H), 8.31 (d, 1H), 7.57 (m, 6H), 7.14 (m, 4H), 7.05 (m, 1H), 3.31 (m, 2H), 2.65 (s, 3H), 2.62 (m, 2H), 1.73 (m, 2H), 1.57 (m, 2H) ppm mp: 224-226° C.

Compound 114

1-[3-(1-Butyl-1H-pyrazol-4-yl)-pyrido[2,3-b]pyrazin-6-yl]-3-(4-phenyl-butyl)-urea

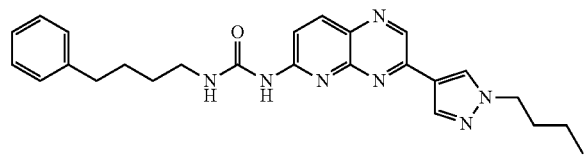 [SMILES: CCCCn1cc(-c2cnc3ccc(NC(=O)NCCCCc4ccccc4)nc3n2)cn1]

$^1$H-NMR (DMSO-d$_6$□□): □=10.01 (s, 1H), 9.26 (s, 1H), 9.16 (s, 1H), 8.61 (s, 1H), 8.27 (m, 2H), 7.55 (d, 1H), 7.23 (m, 4H), 7.13 (m, 1H), 4.19 (m, 2H), 3.33 (m, 2H), 2.68 (m, 2H), 2.55 (m, 2H), 1.81 (m, 2H), 1.72 (m, 2H), 1.59 (m, 2H), 1.28 (m, 2H), 0.90 (t, 3H) ppm

Compound 115

1-[4-(4-Methoxy-phenyl)-butyl]-3-[3-(1-methyl-1H-pyrazol-4-yl)-pyrido[2,3-b]pyrazin-6-yl]-urea

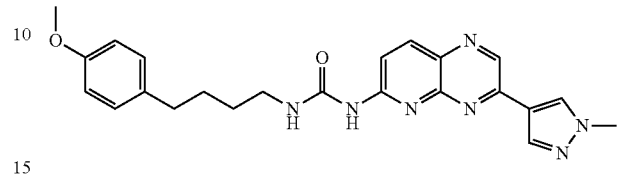

$^1$H-NMR (DMSO-d$_6$□□): □=10.01 (s, 1H), 9.26 (s, 1H), 9.15 (s, 1H), 8.56 (s, 1H), 8.26 (m, 2H), 7.54 (d, 1H), 7.13 (d, 2H), 6.78 (d, 2H), 3.94 (s, 3H), 3.68 (s, 3H), 3.30 (m, 2H), 2.60 (m, 2H), 1.68 (m, 2H), 1.57 (m, 2H), ppm mp: 195-196° C.

Compound 116

1-(4-Phenyl-butyl)-3-[3-(piperidin-4-ylamino)-pyrido[2,3-b]pyrazin-6-yl]-urea

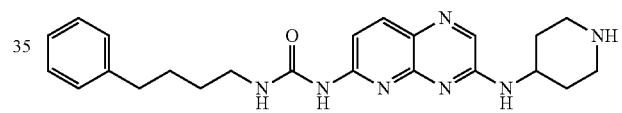

$^1$H-NMR (DMSO-d$_6$□□): □=10.14 (bs, 1H), 9.09 (bs, 1H), 8.71 (s, 1H), 8.12 (m, 4H), 7.22 (m, 6H), 4.61 (m, 2H), 3.38 (m, 2H), 3.27 (m, 2H), 3.12 (m, 2H), 2.65 (m, 2H), 2.03 (m, 2H), 1.71 (m, 2H), 1.55 (m, 4H) ppm mp: 243 (dec.)

Compound 117

1-(4-Phenyl-butyl)-3-{3-[(pyridin-4-ylmethyl)-amino]-pyrido[2,3-b]pyrazin-6-yl}-urea

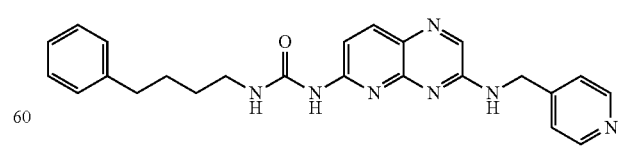

$^1$H-NMR (DMSO-d$_6$□□): □=9.65 (s, 1H), 9.12 (bs, 1H), 8.49 (m, 2H), 8.43 (m, 1H), 8.23 (m, 1H), 8.00 (m, 1H), 7.34 (m, 2H), 7.18 (m, 6H), 4.61 (m, 2H), 3.24 (m, 2H), 2.59 (m, 2H), 1.76 (m, 2H), 1.49 (m, 2H) ppm

Compound 118

1-[3-(4-Methoxy-phenyl)-pyrido[2,3-b]pyrazin-6-yl]-3-(4-phenyl-butyl)-urea

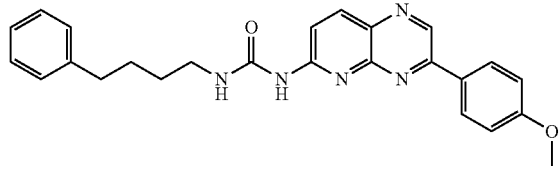 [SMILES: COc1ccc(-c2cnc3ccc(NC(=O)NCCCCc4ccccc4)nc3n2)cc1]

$^1$H-NMR (DMSO-d$_6$): δ=10.08 (s, 1H), 9.41 (s, 1H), 9.33 (s, 1H), 8.31 (m, 3H), 7.59 (m, 1H), 7.22 (m, 4H), 7.12 (m, 3H), 3.87 (s, 3H), 3.34 (m, 2H), 2.68 (m, 2H), 1.75 (m, 2H), 1.59 (m, 2H) ppm mp: 200-203° C.

Compound 119

1-(4-Phenyl-butyl)-3-(3-propylamino-pyrido[2,3-b]pyrazin-6-yl)-urea

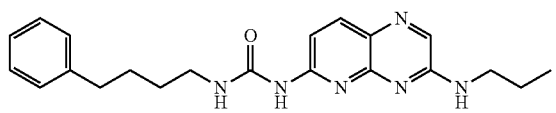 [SMILES: CCCNc1cnc2ccc(NC(=O)NCCCCc3ccccc3)nc2n1]

$^1$H-NMR (DMSO-d$_6$): δ=9.62 (s, 1H), 9.33 (bs, 1H), 8.12 (s, 1H), 7.96 (m, 1H), 7.83 (m, 1H), 7.21 (m, 6H), 3.32 (m, 2H), 3.26 (m, 2H), 2.65 (m, 2H), 1.72 (m, 2H), 1.57 (m, 4H), 0.91 (m, 3H) ppm mp: 118-120° C.

Compound 120

1-(4-Phenyl-butyl)-3-(3-o-tolyl-pyrido[2,3-b]pyrazin-6-yl)-urea

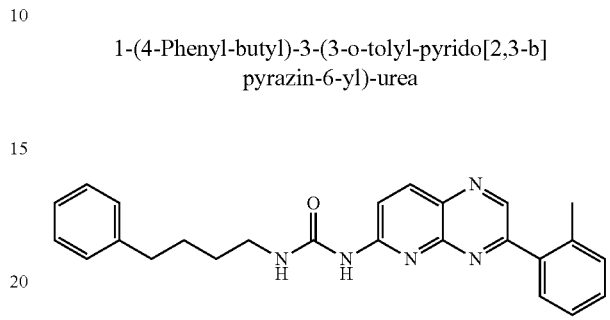

$^1$H-NMR (DMSO-d$_6$): δ=10.15 (s, 1H), 9.27 (bs, 1H), 9.00 (s, 1H), 8.39 (m, 1H), 7.68 (m, 1H), 7.62 (m, 1H), 7.41 (m, 3H), 7.17 (m, 4H), 7.11 (m, 1H), 2.62 (m, 2H), 2.43 (s, 3H), 1.69 (m, 2H), 1.56 (m, 2H) ppm mp: 158-160° C.

Compound 121

3-{6-[3-(4-Phenyl-butyl)-ureido]-pyrido[2,3-b]pyrazin-3-yl}-benzoic acid ethyl ester

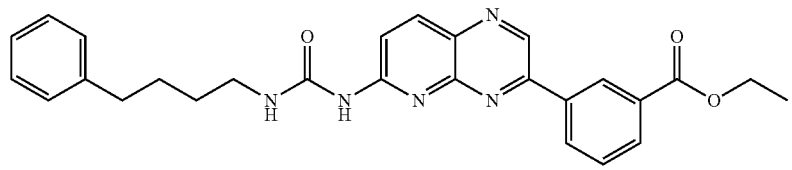 [SMILES: CCOC(=O)c1cccc(-c2cnc3ccc(NC(=O)NCCCCc4ccccc4)nc3n2)c1]

$^1$H-NMR (DMSO-d$_6$): δ=10.16 (s, 1H), 9.52 (s, 1H), 9.28 (bs, 1H), 8.89 (s, 1H), 8.59 (m, 1H), 8.40 (m, 1H), 8.15 (m, 1H), 7.75 (m, 1H), 7.70 (m, 1H), 7.16 (m, 5H), 4.37 (m, 2H), 3.35 (s, 2H), 2.68 (m, 2H), 1.76 (m, 2H), 1.61 (m, 2H), 1.36 (m, 3H) ppm mp: 190-191° C.

Compound 122

Ethyl-carbamic acid 4-{6-[3-(4-phenyl-butyl)-ureido]-pyrido[2,3-b]pyrazin-3-yl}-phenyl ester

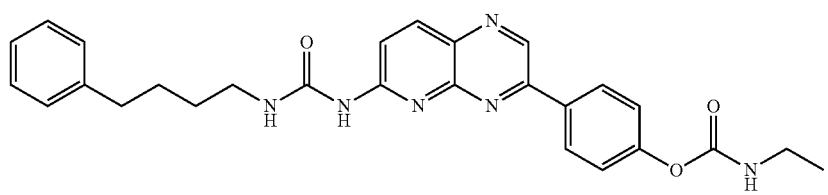 [SMILES: CCNC(=O)Oc1ccc(-c2cnc3ccc(NC(=O)NCCCCc4ccccc4)nc3n2)cc1]

¹H-NMR (DMSO-d₆): δ=10.12 (s, 1H), 9.44 (s, 1H), 9.30 (bs, 1H), 8.33 (m, 3H), 7.86 (m, 1H), 7.64 (m, 1H), 7.31 (m, 2H), 7.21 (m, 4H), 7.12 (m, 1H), 3.34 (m, 2H), 3.13 (m, 2H), 2.67 (m, 2H), 1.74 (m, 2H), 1.60 (m, 2H), 1.11 (m, 3H) ppm mp: 198° C.

Compound 123

1-[3-(4-Amino-3-methoxy-phenyl)-pyrido[2,3-b]pyrazin-6-yl]-3-(4-phenyl-butyl)-urea

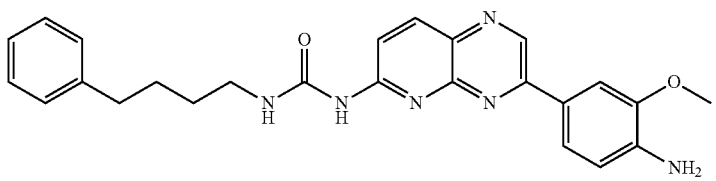 [SMILES: COc1cc(-c2cnc3ccc(NC(=O)NCCCCc4ccccc4)nc3n2)ccc1N]

¹H-NMR (DMSO-d₆): δ=10.00 (s, 1H), 9.35 (s, 1H), 9.31 (bs, 1H), 8.25 (d, 1H), 7.79 (m, 2H), 7.51 (m, 1H), 7.21 (m, 5H), 7.12 (m, 1H), 6.76 (m, 1H), 5.49 (s, 2H), 3.85 (s, 3H), 3.34 (m, 2H), 2.67 (m, 2H), 1.75 (m, 2H), 1.59 (m, 2H) ppm Compound 124

1-[3-(2-Methoxy-phenyl)-pyrido[2,3-b]pyrazin-6-yl]-3-(4-phenyl-butyl)-urea

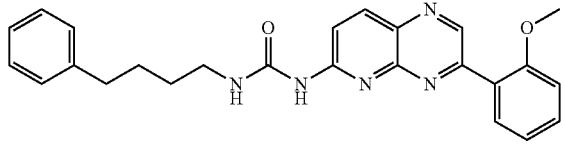 [SMILES: COc1ccccc1-c1cnc2ccc(NC(=O)NCCCCc3ccccc3)nc2n1]

¹H-NMR (DMSO-d₆): δ=10.09 (s, 1H), 9.29 (bs, 1H), 9.20 (s, 1H), 8.35 (d, 1H), 7.81 (m, 1H), 7.64 (m, 1H), 7.55 (m, 1H), 7.27 (m, 1H), 7.19 (m, 4H), 7.13 (m, 2H), 3.91 (s, 3H), 3.33 (m, 2H), 2.64 (m, 2H), 1.70 (m, 2H), 1.57 (m, 2H) ppm mp: 173-177° C.

Compound 125

1-((R)-1-Methyl-4-phenyl-butyl)-3-[3-(2,3,4-tri-methoxy-phenyl)-pyrido[2,3-b]pyrazin-6-yl]-urea ¹H-NMR (DMSO-d₆): δ=10.02 (s, 1H), 9.25 (bs, 1H), 9.11 (s, 1H), 8.34 (d, 1H), 7.64 (m, 1H), 7.61 (m, 1H), 7.18 (m, 4H), 7.12 (m, 1H), 7.01 (m, 1H), 3.89 (m, 4H), 3.85 (s, 3H), 3.84 (s, 3H), 2.62 (m, 2H), 1.71 (m, 2H), 1.56 (m, 2H), 1.19 (d, 3H) ppm mp: 123-125° C.

Compound 126

1-(1-Methyl-4-phenyl-butyl)-3-[3-(1-propyl-1H-pyrazol-4-yl)-pyrido[2,3-b]pyrazin-6-yl]-urea ¹H-NMR (DMSO-d₆): δ=9.91 (s, 1H), 9.16 (s, 1H), 9.13 (s, 1H), 8.61 (s, 1H), 8.27 (m, 2H), 7.59 (m, 1H), 7.20 (m, 4H), 7.12 (m, 1H), 4.16 (m, 2H), 3.87 (m, 1H), 2.66 (m, 2H), 1.85 (m, 2H), 1.73 (m, 2H), 1.57 (m, 2H), 1.21 (d, 3H), 0.86 (t, 3H) ppm mp: 166-168° C.

Compound 127

1-{3-[1-(2-Morpholin-4-yl-ethyl)-1H-pyrazol-4-yl]-pyrido[2,3-b]pyrazin-6-yl}-3-(4-phenyl-butyl)-urea

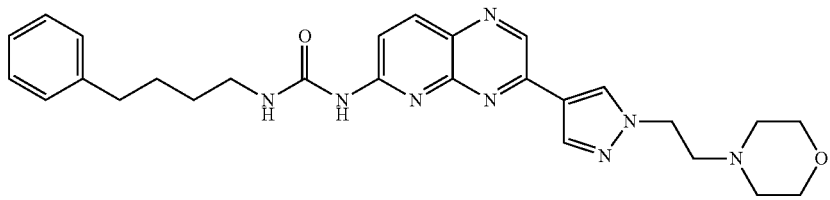 [SMILES: O=C(NCCCCc1ccccc1)Nc1ccc2ncc(-c3cnn(CCN4CCOCC4)c3)nc2n1]

¹H-NMR (DMSO-d₆): δ=10.01 (s, 1H), 9.26 (s, 1H), 9.16 (s, 1H), 8.63 (s, 1H), 8.27 (m, 2H), 7.55 (m, 1H), 7.23 (m, 4H), 7.13 (m, 1H), 4.32 (m, 2H), 3.54 (m, 4H), 3.33 (m, 2H), 2.77 (m, 2H), 2.67 (m, 2H), 2.43 (m, 4H), 1.72 (m, 2H), 1.59 (m, 2H) ppm mp: 190-193° C.

Compound 128

1-[3-(2-Ethoxy-phenyl)-pyrido[2,3-b]pyrazin-6-yl]-3-((R)-1-methyl-4-phenyl-butyl)-urea

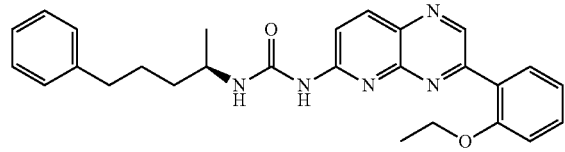 [SMILES: CCOc1ccccc1-c1cnc2ccc(NC(=O)N[C@H](C)CCCc3ccccc3)nc2n1]

¹H-NMR (DMSO-d₆): δ=10.00 (s, 1H), 9.26 (s, 1H), 9.16 (s, 1H), 8.35 (m, 1H), 7.85 (m, 1H), 7.68 (m, 1H), 7.52 (m, 1H), 7.25 (m, 1H), 7.15 (m, 6H), 4.20 (m, 2H), 3.87 (m, 1H), 2.62 (m, 2H), 1.72 (m, 2H), 1.55 (m, 2H), 1.36 (m, 3H), 1.19 (m, 3H) ppm mp: 144-146° C.

Compound 129

1-[3-(3-Chloro-4-hydroxy-phenyl)-pyrido[2,3-b]pyrazin-6-yl]-3-((R)-1-methyl-4-phenyl-butyl)-urea

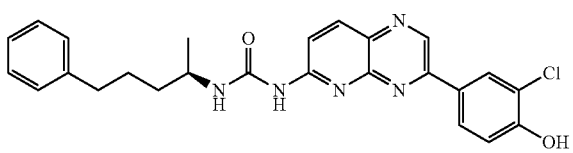 [SMILES: C[C@H](CCCc1ccccc1)NC(=O)Nc1ccc2ncc(-c3ccc(O)c(Cl)c3)nc2n1]

¹H-NMR (DMSO-d₆): δ=10.93 (s, 1H), 9.99 (s, 1H), 9.40 (s, 1H), 9.26 (s, 1H), 8.36 (m, 1H), 8.31 (m, 1H), 8.17 (m, 1H), 7.62 (m, 1H), 7.19 (m, 4H), 7.13 (m, 2H), 3.86 (m, 1H), 2.68 (m, 2H), 1.76 (m, 2H), 1.58 (m, 2H), 1.21 (d, 3H) ppm mp: 225-228° C.

Compound 130

1-[3-(2-Amino-phenyl)-pyrido[2,3-b]pyrazin-6-yl]-3-(4-phenyl-butyl)-urea

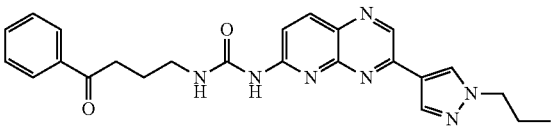 [SMILES: CCCn1cc(-c2cnc3ccc(NC(=O)NCCCC(=O)c4ccccc4)nc3n2)cn1]

¹H-NMR (DMSO-d₆): δ=10.1 (s, 1H), 9.34 (s, 1H), 9.03 (s, 1H), 8.32 (d, 1H), 8.01 (d, 1H), 7.65 (d, 1H), 7.20 (m, 8H), 7.14 (m, 1H), 6.87 (m, 1H), 6.70 (m, 1H), 2.66 (t, 2H), 1.71 (m, 2H), 1.57 (m, 2H) ppm mp: 190-191° C.

Compound 131

1-(4-Oxo-4-phenyl-butyl)-3-[3-(1-propyl-1H-pyrazol-4-yl)-pyrido[2,3-b]pyrazin-6-yl]-urea

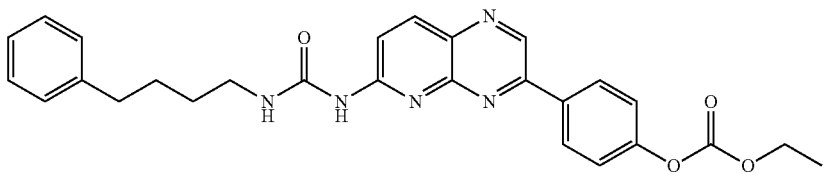 [SMILES: CCOC(=O)Oc1ccc(-c2cnc3ccc(NC(=O)NCCCCc4ccccc4)nc3n2)cc1]

¹H-NMR (DMSO-d₆): δ=10.03 (s, 1H), 9.31 (s, 1H), 8.62 (s, 1H), 8.27 (m, 2H), 7.98 (m, 2H), 7.56 (m, 2H), 7.43 (m, 2H), 4.15 (m, 2H), 3.38 (m, 2H), 3.21 (t, 2H), 1.94 (m, 2H), 1.84 (m, 2H), 0.86 (t, 3H) ppm mp: 210-211° C.

Compound 132

Carbonic acid ethyl ester 4-{6-[3-(4-phenyl-butyl)-ureido]-pyrido[2,3-b]pyrazin-3-yl}-phenyl ester ¹H-NMR (DMSO-d₆): δ=10.14 (s, 1H), 9.46 (s, 1H), 9.30 (s, 1H), 8.38 (m, 3H), 7.65 (d, 1H), 7.45 (d, 2H), 7.17 (m, 5H), 4.30 (m, 2H), 3.34 (m, 2H), 2.67 (t, 2H), 1.74 (m, 2H), 1.60 (m, 2H), 1.32 (t, 3H) ppm mp: 212° C.

Compound 133

1-[3-(2-Hydroxy-phenyl)-pyrido[2,3-b]pyrazin-6-yl]-3-(4-phenyl-butyl)-urea

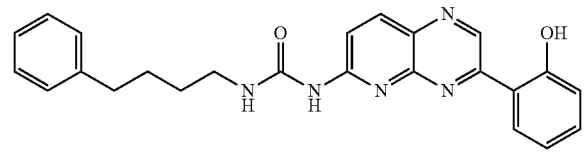

¹H-NMR (DMSO-d₆): δ=12.83 (s, 1H), 10.19 (s, 1H), 9.61 (s, 1H), 8.85 (s, 1H), 8.38 (d, 1H), 8.26 (d, 1H), 7.76 (d, 1H), 7.45 (t, 1H), 7.22 (m, 4H), 7.13 (m, 1H), 7.05 (m, 2H), 2.66 (t, 2H), 1.72 (m, 2H), 1.57 (m, 2H) ppm mp: 247-248° C.

Compound 134

1-[3-(4-Hydroxy-cyclohexylamino)-pyrido[2,3-b]pyrazin-6-yl]-3-(4-phenyl-butyl)-urea

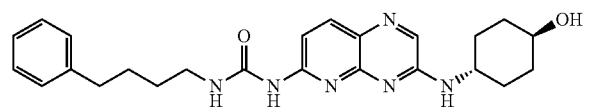 [SMILES: O=C(NCCCCc1ccccc1)Nc1ccc2ncc(N[C@H]3CC[C@H](O)CC3)nc2n1]

¹H-NMR (DMSO-d₆): δ=9.63 (s, 1H), 9.22 (s, 1H), 8.09 (s, 1H), 7.96 (d, 1H), 7.71 (s, 1H), 7.19 (m, 6H), 4.56 (s, 1H), 3.80 (m, 1H), 3.45 (m, 1H), 3.26 (m, 2H), 2.65 (t, 2H), 1.98 (m, 2H), 1.85 (m, 2H), 1.74 (m, 2H), 1.53 (m, 2H), 1.27 (m, 4H) ppm mp: 146° C. (dec.)

Compound 135

2,2-Dimethyl-propionic acid 4-{6-[3-(4-phenyl-butyl)-ureido]-pyrido[2,3-b]pyrazin-3-yl}-phenyl ester

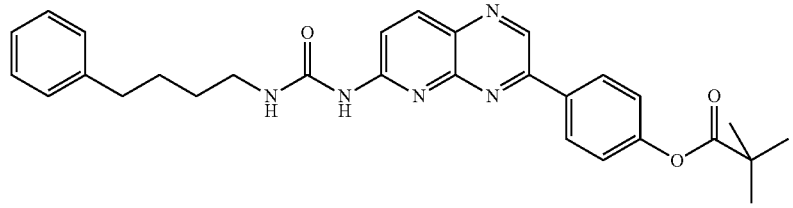 [SMILES: CC(C)(C)C(=O)Oc1ccc(-c2cnc3ccc(NC(=O)NCCCCc4ccccc4)nc3n2)cc1]

¹H-NMR (DMSO-d₆): δ=10.13 (s, 1H), 9.46 (s, 1H), 9.31 (s, 1H), 8.37 (d, 3H), 7.65 (d, 1H), 7.31 (d, 2H), 7.21 (m, 4H), 7.12 (m, 1H), 3.34 (m, 2H), 2.68 (t, 2H), 1.75 (m, 2H), 1.60 (m, 2H), 1.35 (s, 9H) ppm mp: 225° C.

Compound 137

1-[3-(4-Methylsulfanyl-phenyl)-pyrido[2,3-b]pyrazin-6-yl]-3-(4-phenyl-butyl)-urea

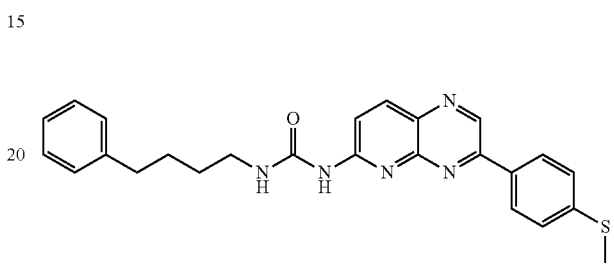

¹H-NMR (DMSO-d₆): δ=10.11 (s, 1H), 9.44 (s, 1H), 9.32 (s, 1H), 8.34 (d, 1H), 8.27 (d, 2H), 7.62 (d, 1H), 7.41 (d, 2H), 7.18 (m, 5H), 3.34 (m, 2H), 2.68 (t, 2H), 2.57 (m, 3H), 1.75 (m, 2H), 1.60 (m, 2H) ppm mp: 227-230° C.

Compound 138

1-[3-(3-Cyano-phenyl)-pyrido[2,3-b]pyrazin-6-yl]-3-(4-phenyl-butyl)-urea

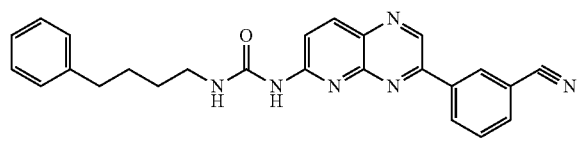 [SMILES: N#Cc1cccc(-c2cnc3ccc(NC(=O)NCCCCc4ccccc4)nc3n2)c1]

¹H-NMR (DMSO-d₆): δ=10.18 (s, 1H), 9.55 (s, 1H), 9.31 (s, 1H), 8.76 (s, 1H), 8.62 (d, 1H), 8.40 (d, 1H), 8.05 (d, 1H), 7.79 (t, 1H), 7.68 (d, 1H), 7.21 (m, 4H), 7.11 (m, 1H), 3.34 (m, 2H), 2.68 (t, 2H), 1.75 (m, 2H), 1.60 (m, 2H) ppm mp: 237-240° C.

Compound 139

1-(4-Phenyl-butyl)-3-[3-(3,4,5-trimethoxy-phenylamino)-pyrido[2,3-b]pyrazin-6-yl]-urea

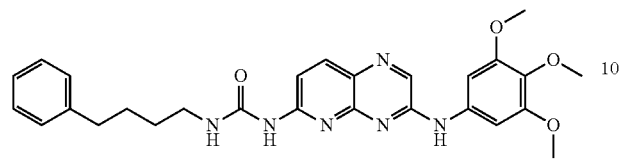

¹H-NMR (DMSO-d₆): δ=10.10 (s, 1H), 9.81 (s, 1H), 9.46 (s, 1H), 8.38 (s, 1H), 8.07 (m, 1H), 7.42 (m, 2H), 7.18 (m, 5H), 3.81 (m, 6H), 3.65 (s, 3H), 3.26 (m, 2H), 2.61 (m, 2H), 1.64 (m, 2H), 1.53 (m, 2H) ppm
mp: 223-225° C.

Compound 140

1-{3-[(S)-1-(3-Chloro-phenyl)-2-hydroxy-ethylamino]-pyrido[2,3-b]pyrazin-6-yl}-3-(4-phenyl-butyl)-urea

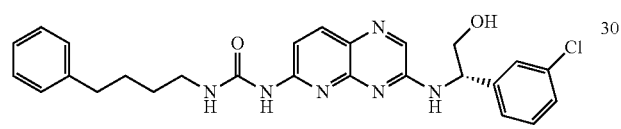

¹H-NMR (DMSO-d₆): δ=9.64 (s, 1H), 9.09 (s, 1H), 8.32 (m, 2H), 7.97 (d, 1H), 7.43 (s, 2H), 7.32 (m, 4H), 7.26 (m, 4H), 7.21 (m, 2H), 7.14 (m, 2H), 5.15 (m, 1H), 5.07 (m, 1H), 4.79 (m, 1H), 3.87 (m, 1H), 3.72 (m, 2H), 3.43 (m, 1H), 3.25 (m, 3H), 2.65 (m, 2H), 1.69 (m, 2H), 1.53 (m, 2H) ppm
mp: 182-184° C.

Compound 141

1-[3-(3-Hydroxy-4,5-dimethoxy-phenylamino)-pyrido[2,3-b]pyrazin-6-yl]-3-(4-phenyl-butyl)-urea

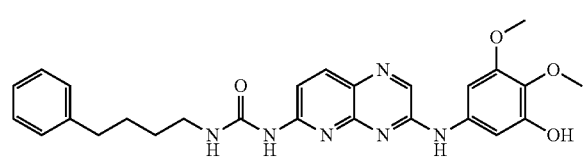 [SMILES: COc1cc(Nc2cnc3ccc(NC(=O)NCCCCc4ccccc4)nc3n2)cc(O)c1OC]

¹H-NMR (DMSO-d₆): δ=9.90 (m, 1H), 9.78 (s, 1H), 9.25 (s, 1H), 9.17 (s, 1H), 8.34 (s, 1H), 8.06 (d, 1H), 7.38 (m, 1H), 7.19 (m, 6H), 7.05 (m, 1H), 3.80 (m, 3H), 3.65 (m, 3H), 3.27 (m, 2H), 2.61 (t, 2H), 1.65 (m, 2H), 1.54 (m, 2H) ppm
mp: 136-139° C.

Compound 142

1-{3-[1-(3-Chloro-phenyl)-2-hydroxy-ethylamino]-pyrido[2,3-b]pyrazin-6-yl}-3-(4-phenyl-butyl)-urea

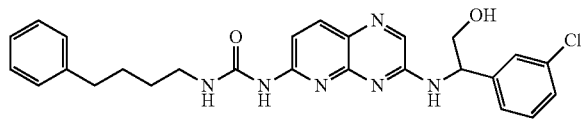 [SMILES: O=C(NCCCCc1ccccc1)Nc1ccc2ncc(NC(CO)c3cccc(Cl)c3)nc2n1]

¹H-NMR (DMSO-d₆): δ=9.65 (s, 1H), 9.09 (s, 1H), 8.31 (m, 2H), 7.98 (d, 1H), 7.44 (m, 2H), 7.24 (m, 4H), 5.14 (m, 1H), 5.06 (t, 1H), 4.79 (m, 1H), 3.87 (m, 1H), 3.73 (m, 2H), 3.44 (m, 1H), 3.26 (m, 2H), 2.65 (m, 2H), 1.71 (m, 2H), 1.54 (m, 2H) ppm
mp: 185-187° C.

Compound 144

1-[3-(4-Fluoro-2-hydroxy-phenyl)-pyrido[2,3-b]pyrazin-6-yl]-3-(4-phenyl-butyl)-urea

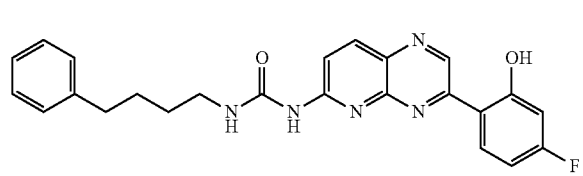 [SMILES: O=C(NCCCCc1ccccc1)Nc1ccc2ncc(-c3ccc(F)cc3O)nc2n1]

¹H-NMR (DMSO-d₆): δ=13.37 (s, 1H), 10.18 (s, 1H), 9.57 (s, 1H), 8.81 (s, 1H), 8.37 (m, 2H), 7.77 (d, 1H), 7.20 (m, 5H), 6.68 (m, 2H), 2.66 (m, 2H), 1.71 (m, 2H), 1.57 (m, 2H) ppm
mp: 248-249° C.

Compound 145

1-{3-[4-Methoxy-3-(morpholine-4-sulfonyl)-phenyl]-pyrido[2,3-b]pyrazin-6-yl}-3-(4-phenyl-butyl)-urea

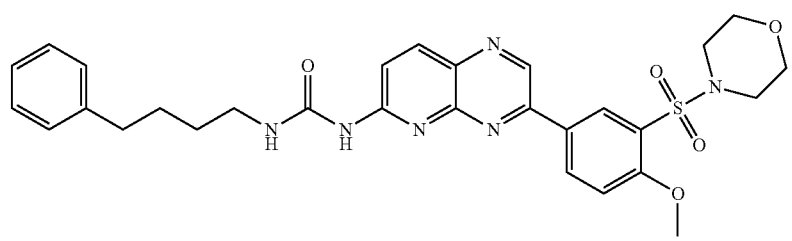 [SMILES: COc1ccc(-c2cnc3ccc(NC(=O)NCCCCc4ccccc4)nc3n2)cc1S(=O)(=O)N1CCOCC1]

¹H-NMR (DMSO-d$_6$): δ=10.12 (s, 1H), 9.46 (s, 1H), 9.22 (s, 1H), 8.73 (m, 1H), 8.62 (m, 1H), 8.37 (d, 1H), 7.68 (d, 1H), 7.47 (d, 1H), 7.19 (m, 4H), 4.03 (s, 3H), 3.58 (m, 4H), 3.32 (m, 2H), 3.12 (m, 2H), 1.75 (m, 2H), 1.59 (m, 2H) ppm
mp: 256-258° C.

Compound 146

1-[3-(2-Methoxy-pyridin-3-yl)-pyrido[2,3-b]pyrazin-6-yl]-3-(4-phenyl-butyl)-urea

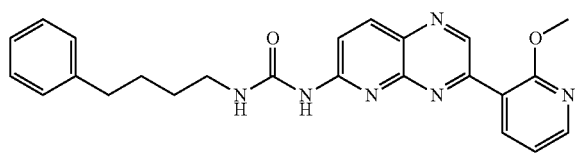 [SMILES: COc1ncccc1-c1cnc2ccc(NC(=O)NCCCCc3ccccc3)nc2n1]

¹H-NMR (DMSO-d$_6$): δ=10.13 (s, 1H), 9.33 (s, 1H), 9.27 (s, 1H), 8.38 (m, 2H), 8.21 (m, 1H), 7.67 (d, 1H), 7.19 (m, 5H), 7.12 (m, 1H), 4.02 (s, 3H), 3.33 (m, 2H), 2.65 (t, 2H), 1.71 (m, 2H), 1.58 (m, 2H) ppm
mp: 194-197° C.

Compound 147

1-[3-(4-Hydroxy-phenyl)-pyrido[2,3-b]pyrazin-6-yl]-3-((R)-1-methyl-4-phenyl-butyl)-urea

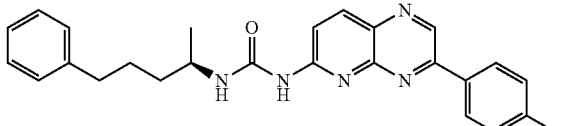

¹H-NMR (DMSO-d$_6$): δ=10.09 (s, 1H), 9.96 (s, 1H), 9.35 (s, 1H), 9.25 (s, 1H), 8.30 (d, 1H), 8.21 (d, 2H), 7.59 (d, 2H), 7.18 (m, 5H), 6.95 (d, 2H), 3.87 (m, 1H), 2.66 (m, 2H), 1.75 (m, 2H), 1.58 (m, 2H), 1.22 (d, 3H) ppm
mp: 226-229° C.

Compound 148

1-[3-(3-Hydroxy-4-methoxy-phenyl)-pyrido[2,3-b]pyrazin-6-yl]-3-((R)-1-methyl-4-phenyl-butyl)-urea

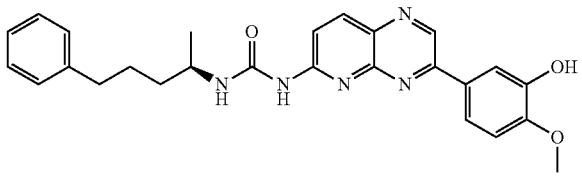 [SMILES: COc1ccc(-c2cnc3ccc(NC(=O)N[C@H](C)CCCc4ccccc4)nc3n2)cc1O]

¹H-NMR (DMSO-d$_6$): δ=9.96 (s, 1H), 9.34 (s, 1H), 9.19 (s, 1H), 8.31 (m, 1H), 7.81 (m, 1H), 7.63 (d, 1H), 7.20 (m, 4H), 7.11 (m, 2H), 3.88 (m, 4H), 2.66 (m, 2H), 1.73 (m, 2H), 1.58 (m, 2H), 1.23 (d, 3H) ppm
mp: 196-198° C.

Compound 149

1-(3-Furan-3-yl-pyrido[2,3-b]pyrazin-6-yl)-3-((R)-1-methyl-4-phenyl-butyl)-urea

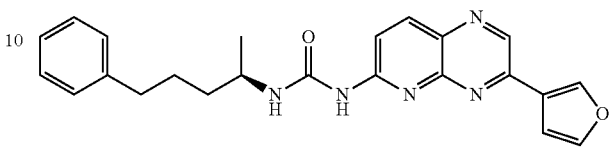

¹H-NMR (DMSO-d$_6$): δ=9.97 (s, 1H), 9.22 (s, 1H), 9.11 (s, 1H), 8.71 (s, 1H), 8.31 (d, 1H), 7.90 (s, 1H), 7.64 (d, 1H), 7.21 (m, 5H), 7.13 (m, 1H), 3.87 (m, 1H), 2.66 (t, 2H), 1.73 (m, 2H), 1.58 (m, 2H), 1.21 (d, 3H) ppm
mp: 218-220° C.

Compound 150

1-((R)-1-Methyl-4-phenyl-butyl)-3-(3-pyridin-3-yl-pyrido[2,3-b]pyrazin-6-yl)-urea

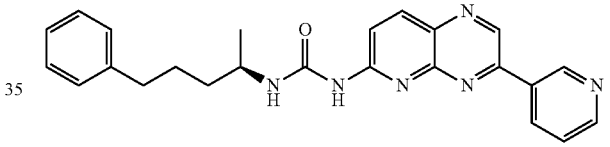

¹H-NMR (DMSO-d$_6$): δ=10.09 (s, 1H), 9.51 (m, 1H), 9.18 (s, 1H), 8.77 (m, 1H), 8.65 (m, 1H), 8.39 (d, 1H), 7.71 (m, 1H), 7.63 (m, 1H), 7.16 (m, 5H), 3.88 (m, 1H), 2.65 (m, 2H), 1.75 (m, 2H), 1.58 (m, 2H), 1.21 (d, 3H) ppm
mp: 218-220° C.

Compound 151

1-[3-(3-Hydroxy-4-methoxy-phenyl)-pyrido[2,3-b]pyrazin-6-yl]-3-(4-phenyl-butyl)-urea

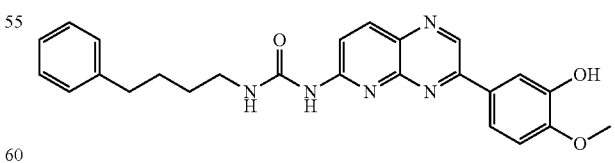

¹H-NMR (DMSO-d$_6$): δ=10.06 (s, 1H), 9.33 (s, 2H), 9.25 (s, 1H), 8.31 (d, 1H), 7.80 (m, 2H), 7.60 (d, 1H), 7.22 (m, 4H), 7.11 (m, 2H), 3.87 (s, 3H), 3.33 (m, 2H), 2.67 (m, 2H), 1.73 (m, 2H), 1.53 (m, 2H) ppm
mp: 230-232° C.

Compound 152

1-(3-Furan-3-yl-pyrido[2,3-b]pyrazin-6-yl)-3-(4-phenyl-butyl)-urea

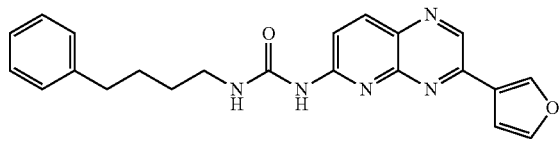 [SMILES: O=C(NCCCCc1ccccc1)Nc1ccc2ncc(-c3ccoc3)nc2n1]

¹H-NMR (DMSO-d₆): δ=10.11 (s, 1H), 9.27 (s, 1H), 9.22 (s, 1H), 8.71 (s, 1H), 8.31 (d, 1H), 7.90 (m, 1H), 7.62 (d, 1H), 7.24 (m, 4H), 7.16 (m, 2H), 3.33 (m, 2H), 2.67 (t, 2H), 1.74 (m, 2H), 1.54 (m, 2H) ppm mp: 212-216° C.

Compound 153

1-((R)-1-Methyl-4-phenyl-butyl)-3-[3-(4-methyl-piperazin-1-yl)-pyrido[2,3-b]pyrazin-6-yl]-urea

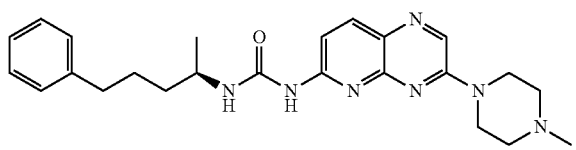 [SMILES: C[C@H](CCCc1ccccc1)NC(=O)Nc1ccc2ncc(N3CCN(C)CC3)nc2n1]

¹H-NMR (DMSO-d₆): δ=9.63 (s, 1H), 9.28 (s, 1H), 8.63 (s, 1H), 8.04 (d, 1H), 7.20 (m, 5H), 3.80 (m, 5H), 2.63 (t, 2H), 2.41 (m, 4H), 2.22 (s, 3H), 1.72 (m, 2H), 1.53 (m, 2H), 1.16 (d, 3H) ppm mp: 172-175° C.

Compound 154

1-((R)-1-Methyl-4-phenyl-butyl)-3-(3-piperidin-1-yl-pyrido[2,3-b]pyrazin-6-yl)-urea

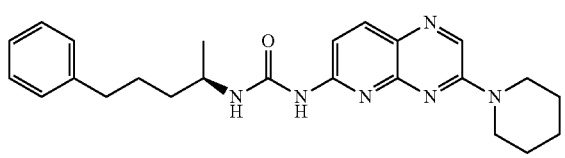 [SMILES: C[C@H](CCCc1ccccc1)NC(=O)Nc1ccc2ncc(N3CCCCC3)nc2n1]

¹H-NMR (DMSO-d₆): δ=9.61 (s, 1H), 9.32 (s, 1H), 8.62 (s, 1H), 8.01 (d, 1H), 7.19 (m, 5H), 3.80 (m, 5H), 2.63 (t, 2H), 1.73 (m, 2H), 1.65 (m, 2H), 1.58 (m, 4H), 1.52 (m, 2H), 1.16 (d, 3H) ppm mp: 171-174° C.

Compound 155

1-[3-(1-Methyl-1H-pyrazol-4-yl)-pyrido[2,3-b]pyrazin-6-yl]-3-(4-phenyl-butyl)-urea

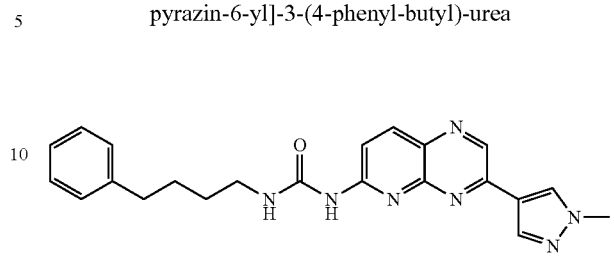

¹H-NMR (DMSO-d₆): δ=10.02 (s, 1H), 9.25 (s, 1H), 9.15 (s, 1H), 8.56 (s, 1H), 8.26 (m, 2H), 7.55 (d, 1H), 7.23 (m, 4H), 7.14 (m, 1H), 3.94 (s, 3H), 3.33 (m, 2H), 2.67 (t, 2H), 1.73 (m, 2H), 1.59 (m, 2H) ppm mp: 198-201° C.

Compound 156

1-[3-(4-Hydroxymethyl-2-methoxy-phenyl)-pyrido[2,3-b]pyrazin-6-yl]-3-((R)-1-methyl-4-phenyl-butyl)-urea

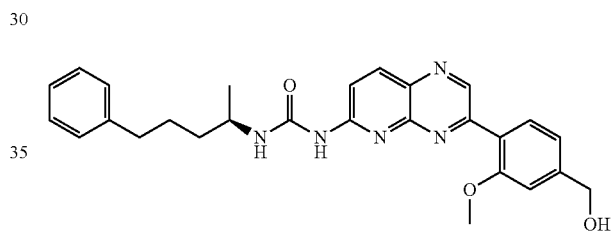

¹H-NMR (DMSO-d₆): δ=9.99 (s, 1H), 9.21 (s, 1H), 9.16 (s, 1H), 8.34 (d, 1H), 7.82 (d, 1H), 7.67 (d, 1H), 7.18 (m, 7H), 5.35 (t, 1H), 4.61 (d, 2H), 3.87 (m, 4H), 2.63 (m, 2H), 1.72 (m, 2H), 1.55 (m, 2H), 1.19 (d, 3H) ppm mp: 168-170° C.

Compound 157

1-((R)-1-Methyl-4-phenyl-butyl)-3-(3-pyridin-4-yl-pyrido[2,3-b]pyrazin-6-yl)-urea

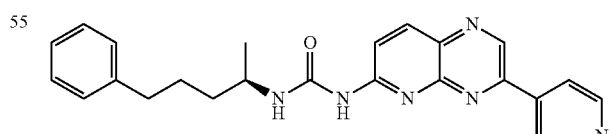

¹H-NMR (DMSO-d₆): δ=10.11 (s, 1H), 9.54 (s, 1H), 9.15 (s, 1H), 8.81 (d, 2H), 8.41 (d, 1H), 8.26 (d, 2H), 7.75 (d, 1H), 7.20 (d, 4H), 7.12 (m, 1H), 3.89 (m, 1H), 2.66 (m, 2H), 1.75 (m, 2H), 1.59 (m, 2H), 1.22 (d, 3H) ppm mp: 223-226° C.

Compound 158

1-[3-(3-Hydroxymethyl-2-methoxy-phenyl)-pyrido[2,3-b]pyrazin-6-yl]-3-((R)-1-methyl-4-phenyl-butyl)-urea

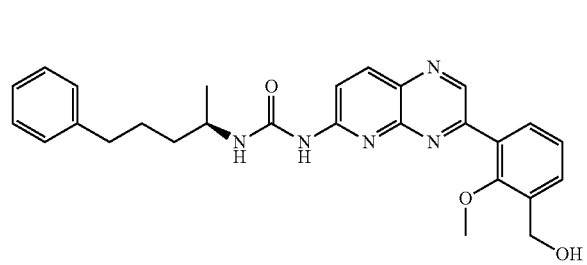 [SMILES: COc1c(CO)cccc1-c1cnc2ccc(NC(=O)N[C@H](C)CCCc3ccccc3)nc2n1]

$^1$H-NMR (DMSO-d$_6$): δ=9.98 (s, 1H), 9.21 (s, 1H), 9.15 (s, 1H), 8.34 (d, 1H), 7.81 (d, 1H), 7.68 (d, 1H), 7.16 (m, 7H), 5.35 (t, 1H), 4.61 (d, 2H), 3.92 (s, 2H), 3.87 (m, 1H), 2.63 (m, 2H), 1.72 (m, 2H), 1.55 (m, 2H), 1.19 (d, 3H) ppm mp: 168-170° C.

Compound 159

1-(4-Phenyl-butyl)-3-[3-(1H-pyrazol-4-yl)-pyrido[2,3-b]pyrazin-6-yl]-urea

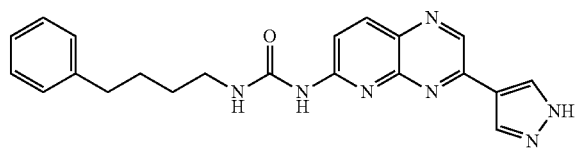 [SMILES: O=C(NCCCCc1ccccc1)Nc1ccc2ncc(-c3cn[nH]c3)nc2n1]

$^1$H-NMR (DMSO-d$_6$): δ=13.39 (s, 1H), 10.01 (s, 1H), 9.27 (s, 1H), 9.21 (s, 1H), 8.63 (s, 1H), 8.28 (m, 2H), 7.55 (d, 1H), 7.23 (m, 4H), 7.14 (m, 1H), 3.32 (m, 2H), 2.67 (m, 2H), 1.74 (m, 2H), 1.60 (m, 2H) ppm mp: 231-232° C.

Compound 160

1-[3-(4-Hydroxy-phenyl)-pyrido[2,3-b]pyrazin-6-yl]-3-(4-phenyl-butyl)-urea

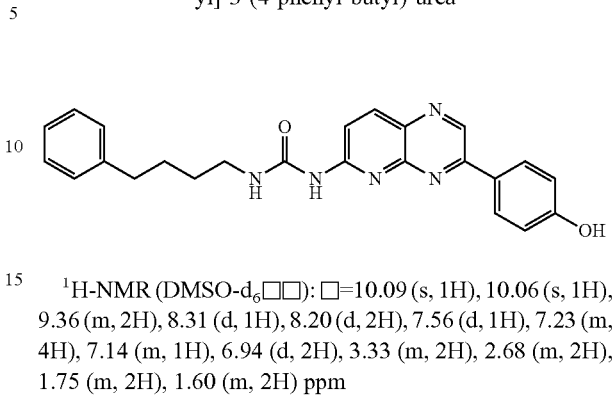

$^1$H-NMR (DMSO-d$_6$): δ=10.09 (s, 1H), 10.06 (s, 1H), 9.36 (m, 2H), 8.31 (d, 1H), 8.20 (d, 2H), 7.56 (d, 1H), 7.23 (m, 4H), 7.14 (m, 1H), 6.94 (d, 2H), 3.33 (m, 2H), 2.68 (m, 2H), 1.75 (m, 2H), 1.60 (m, 2H) ppm mp: 233-235° C.

Compound 161

1-[3-(2-Methoxy-pyridin-3-yl)-pyrido[2,3-b]pyrazin-6-yl]-3-((R)-1-methyl-4-phenyl-butyl)-urea

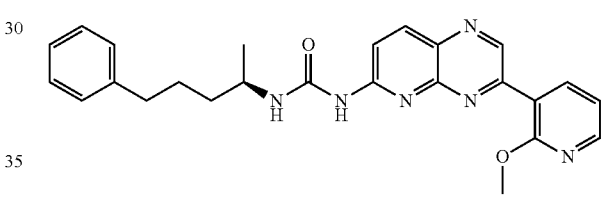

$^1$H-NMR (DMSO-d$_6$): δ=10.04 (s, 1H), 9.32 (s, 1H), 9.13 (s, 1H), 8.38 (m, 2H), 8.31 (d, 1H), 7.71 (d, 1H), 7.17 (m, 6H), 4.02 (s, 3H), 3.87 (m, 1H), 2.63 (m, 2H), 1.72 (m, 2H), 1.56 (m, 2H), 1.20 (d, 3H) ppm mp: 161-163° C.

Compound 162

1-{3-[1-(3-Hydroxy-propyl)-1H-pyrazol-4-yl]-pyrido[2,3-b]pyrazin-6-yl}-3-(4-phenyl-butyl)-urea

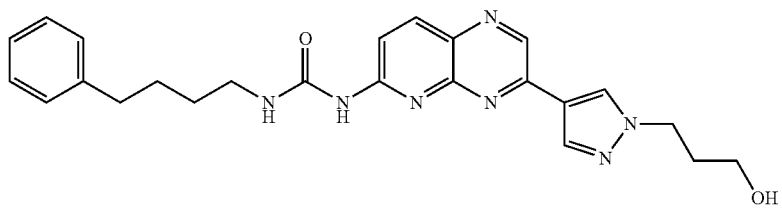 [SMILES: O=C(NCCCCc1ccccc1)Nc1ccc2ncc(-c3cnn(CCCO)c3)nc2n1]

$^1$H-NMR (DMSO-d$_6$): δ=10.01 (s, 1H), 9.24 (s, 1H), 9.16 (s, 1H), 8.61 (s, 1H), 8.27 (m, 2H), 7.55 (d, 1H), 7.23 (m, 4H), 7.14 (m, 1H), 4.63 (t, 1H), 4.26 (t, 2H), 3.43 (m, 2H), 3.33 (m, 2H), 2.67 (t, 2H), 1.98 (m, 2H), 1.73 (m, 2H), 1.59 (m, 2H) ppm mp: 182-184° C.

Compound 163

1-{3-[1-(2,2-Difluoro-ethyl)-1H-pyrrol-3-yl]-pyrido[2,3-b]pyrazin-6-yl}-3-(4-phenyl-butyl)-urea

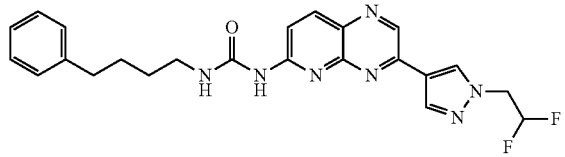 [SMILES: O=C(NCCCCc1ccccc1)Nc1ccc2ncc(-c3cnn(CC(F)F)c3)nc2n1]

¹H-NMR (DMSO-d₆): δ=10.03 (s, 1H), 9.23 (s, 1H), 9.20 (s, 1H), 8.68 (s, 1H), 8.37 (s, 1H), 8.29 (d, 1H), 7.58 (d, 1H), 7.23 (d, 4H), 7.14 (m, 1H), 6.45 (t, 1H), 4.76 (m, 2H), 2.67 (t, 2H), 1.72 (m, 2H), 1.59 (m, 2H) ppm

Compound 164

1-(1-Methyl-4-phenyl-butyl)-3-[3-(1-methyl-1H-pyrazol-4-yl)-pyrido[2,3-b]pyrazin-6-yl]-urea

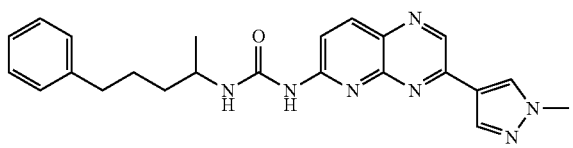 [SMILES: CC(CCCc1ccccc1)NC(=O)Nc1ccc2ncc(-c3cnn(C)c3)nc2n1]

¹H-NMR (DMSO-d₆): δ=9.90 (s, 1H), 9.14 (s, 1H), 9.11 (s, 1H), 8.56 (s, 1H), 8.25 (m, 2H), 7.58 (d, 1H), 7.21 (m, 4 h), 7.12 (m, 1H), 3.94 (s, 3H), 3.87 (m, 1H), 2.64 (m, 2H), 1.77 (m, 2H), 1.57 (m, 2H), 1.21 (d, 3H) ppm
mp: 204-208° C.

Compound 165

Phosphoric acid mono-(4-{6-[3-(4-phenyl-butyl)-ureido]-pyrido[2,3-b]pyrazin-3-yl}-phenyl) ester

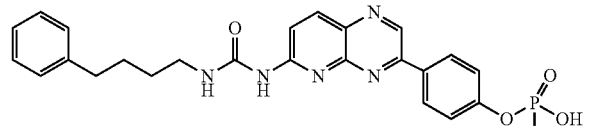

¹H-NMR (MeOD-d₄): δ=12.2 (bs, 1H), 10.11 (s, 1H), 9.42 (s, 1H), 9.28 (s, 1H), 8.32 (m, 3H), 7.64 (d, 1H), 7.36 (d, 2H), 7.22 (m, 4H), 7.14 (m, 1H), 3.33 (m, 2H), 2.67 (m, 2H), 1.75 (m, 2H), 1.59 (m, 2H) ppm
mp: 202° C.

Compound 166

1-((R)-1-Methyl-4-phenyl-butyl)-3-(3-morpholin-4-yl-pyrido[2,3-b]pyrazin-6-yl)-urea

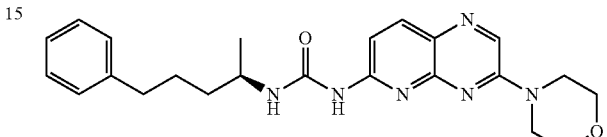

¹H-NMR (MeOD-d₄): δ=9.66 (s, 1H), 9.25 (s, 1H), 8.61 (s, 1H), 8.06 (d, 1H) 7.21 (m, 6H), 3.83 (m, 1H), 3.73 (m, 8H), 2.63 (m, 2H). 1.71 (m, 2H), 1.52 (m, 2H), 1.17 (d, 3H) ppm
mp: 201-203° C.

Compound 167

1-[3-(4-Hydroxymethyl-phenyl)-pyrido[2,3-b]pyrazin-6-yl]-3-((R)-1-methyl-4-phenyl-butyl)-urea

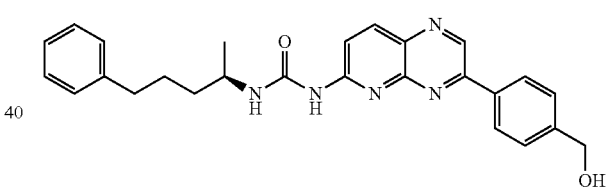

¹H-NMR (MeOD-d₄): δ=10.02 (s, 1H), 9.45 (s, 1H), 9.22 (s, 1H), 8.33 (m, 3H), 7.67 (d, 1H), 7.53 (d, 2H), 7.20 (m, 4H), 7.12 (m, 1H), 5.34 (t, 1H), 4.61 (d, 2H), 3.88 (m, 1H), 2.66 (m, 2H), 1.75 (m, 2H), 1.59 (m, 2H), 1.22 (t, 3H) ppm
mp: 187-190° C.

Compound 168

1-((R)-1-Methyl-4-phenyl-butyl)-3-{3-[1-(2-morpholin-4-yl-ethyl)-1H-pyrazol-4-yl]-pyrido[2,3-b]pyrazin-6-yl}-urea

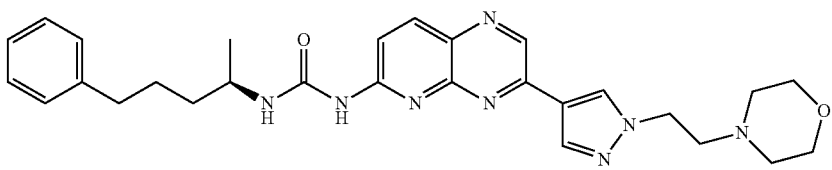 [SMILES: C[C@H](CCCc1ccccc1)NC(=O)Nc1ccc2ncc(-c3cnn(CCN4CCOCC4)c3)nc2n1]

¹H-NMR (DMSO-d$_6$): δ=9.92 (s, 1H), 9.16 (m, 2H), 8.63 (s, 1H), 8.28 (m, 2H), 7.57 (m, 1H), 7.21 (m, 4H), 7.12 (m, 1H), 4.33 (m, 2H), 3.87 (m, 1H), 3.55 (m, 4H), 2.76 (m, 2H), 2.65 (m, 2H), 2.46 (m, 4H), 1.72 (m, 2H), 1.57 (m, 2H), 1.22 (m, 3H) ppm mp: 178-180° C.

Compound 169

1-(4-Methyl-4-phenyl-pentyl)-3-[3-(1-methyl-1H-pyrazol-4-yl)-pyrido[2,3-b]pyrazin-6-yl]-urea

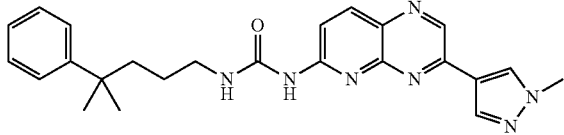 [SMILES: Cn1cc(-c2cnc3ccc(NC(=O)NCCCC(C)(C)c4ccccc4)nc3n2)cn1]

¹H-NMR (DMSO-d$_6$): δ=9.98 (s, 1H), 9.18 (s, 1H), 9.15 (s, 1H), 8.58 (s, 1H), 8.26 (m, 2H), 7.53 (d, 1H), 7.38 (d, 2H), 7.25 (t, 2H), 7.13 (t, 1H), 3.95 (s, 3H), 3.18 (m, 2H), 1.75 (m, 2H), 1.31 (s, 8H) ppm mp: 208-210° C.

Compound 170

1-((R)-1-Methyl-4-phenyl-butyl)-3-[3-(1-propyl-1H-pyrazol-4-yl)-pyrido[2,3-b]pyrazin-6-yl]-urea

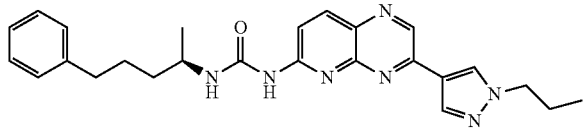 [SMILES: CCCn1cc(-c2cnc3ccc(NC(=O)N[C@H](C)CCCc4ccccc4)nc3n2)cn1]

¹H-NMR (DMSO-d$_6$): δ=9.91 (s, 1H), 9.16 (s, 1H), 9.12 (bs, 1H), 8.61 (s, 1H), 8.27 (m, 2H), 7.58 (d, 1H), 7.21 (m, 4H), 7.12 (m, 1H), 4.16 (m, 2H), 3.87 (m, 1H), 2.66 (m, 2H), 1.85 (m, 2H), 1.72 (m, 2H), 1.22 (d, 3H), 0.87 (t, 3H) ppm mp: 185-188° C.

Compound 171

1-((R)-1-Methyl-4-phenyl-butyl)-3-[3-(1H-pyrazol-4-yl)-pyrido[2,3-b]pyrazin-6-yl]-urea

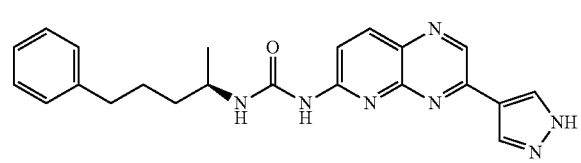 [SMILES: C[C@H](CCCc1ccccc1)NC(=O)Nc1ccc2ncc(-c3cn[nH]c3)nc2n1]

¹H-NMR (DMSO-d$_6$): δ=13.38 (s, 1H), 9.91 (s, 1H), 9.20 (s, 1H), 9.13 (s, 1H), 8.65 (s, 1H), 8.29 (m, 2H), 7.58 (d, 1H), 7.21 (m, 4H), 7.13 (m, 1H), 3.87 (m, 1H), 2.66 (m, 2H), 1.73 (m, 2H), 1.58 (m, 2H), 1.21 (d, 3H) ppm mp: 274-276° C.

Compound 172

1-(4-Phenyl-butyl)-3-(3-pyrrolidin-1-yl-pyrido[2,3-b]pyrazin-6-yl)-urea

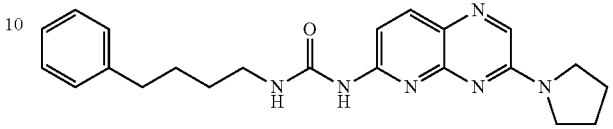

¹H-NMR (DMSO-d$_6$): δ=9.68 (s, 1H), 9.43 (s, 1H), 8.28 (s, 1H), 8.02 (d, 1H), 7.23 (m, 3H), 7.16 (t, 1H), 7.11 (d, 1H), 3.56 (s, 3H), 3.29 (m, 2H), 2.65 (m, 2H), 1.96 (m, 4H), 1.73 (m, 2H), 1.54 (m, 2H) ppm mp: 204-206° C.

Compound 173

1-((R)-1-Methyl-4-phenyl-butyl)-3-(3-pyrrolidin-1-yl-pyrido[2,3-b]pyrazin-6-yl)-urea

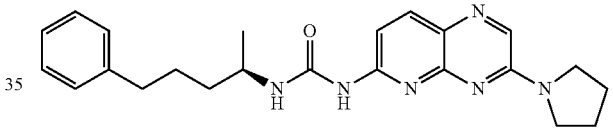

¹H-NMR (DMSO-d$_6$): δ=9.57 (s, 1H), 9.29 (s, 1H), 8.28 (s, 1H), 8.02 (d, 1H), 7.19 (m, 6H), 3.83 (m, 1H), 3.58 (m, 4H), 2.63 (t, 2H), 1.97 (m, 4H), 1.72 (m, 2H), 1.53 (m, 2H), 1.17 (d, 3H) ppm mp: 187-190° C.

Compound 174

1-[3-(3-Fluoro-4-hydroxy-phenyl)-pyrido[2,3-b]pyrazin-6-yl]-3-(4-phenyl-butyl)-urea

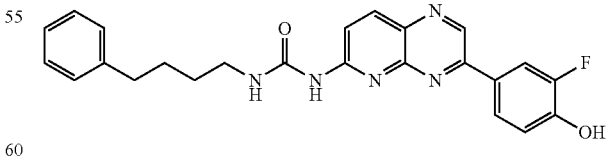

¹H-NMR (DMSO-d$_6$): δ=10.57 (s, 1H), 10.09 (s, 1H), 9.40 (s, 1H), 9.33 (s, 1H), 8.32 (d, 1H), 8.15 (m, 1H), 8.04 (m, 1H), 7.59 (d, 1H), 7.22 (m, 4H), 7.13 (m, 2H), 3.33 (m, 2H), 2.68 (t, 2H), 1.75 (m, 2H), 1.59 (m, 2H) ppm mp: 269-270° C.

Compound 175

1-[3-(3-Hydroxymethyl-phenyl)-pyrido[2,3-b]pyrazin-6-yl]-3-(4-phenyl-butyl)-urea

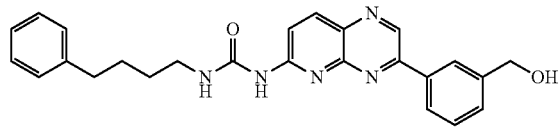 [SMILES: O=C(NCCCCc1ccccc1)Nc1ccc2ncc(-c3cccc(CO)c3)nc2n1]

$^1$H-NMR (DMSO-d$_6$☐☐): ☐=10.11 (s, 1H), 9.43 (s, 1H), 9.27 (s, 1H), 8.37 (d, 1H), 8.28 (s, 1H), 8.18 (m, 1H), 7.66 (d, 1H), 7.54 (m, 2H), 7.21 (m, 4H), 7.12 (m, 1H), 5.33 (t, 1H), 4.62 (d, 2H), 3.34 (m, 2H), 2.68 (t, 2H), 1.75 (m, 2H), 1.59 (m, 2H) ppm mp: 198-200° C.

Compound 176

1-(3-Morpholin-4-yl-pyrido[2,3-b]pyrazin-6-yl)-3-(4-phenyl-butyl)-urea

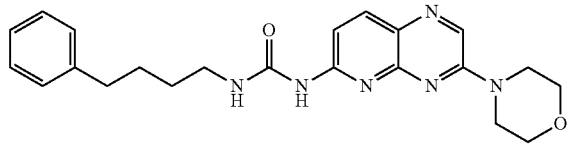 [SMILES: O=C(NCCCCc1ccccc1)Nc1ccc2ncc(N3CCOCC3)nc2n1]

$^1$H-NMR (DMSO-d$_6$☐☐): ☐=9.75 (s, 1H), 9.36 (s, 1H), 8.62 (s, 1H), 8.06 (d, 1H), 7.21 (m, 6H), 3.71 (m, 8H), 3.29 (m, 2H), 2.65 (t, 2H), 1.72 (m, 2H), 1.55 (m, 2H) ppm mp: 200-202° C.

Compound 177

1-[3-(3,5-Dimethyl-1H-pyrazol-4-yl)-pyrido[2,3-b]pyrazin-6-yl]-3-((R)-1-methyl-4-phenyl-butyl)-urea

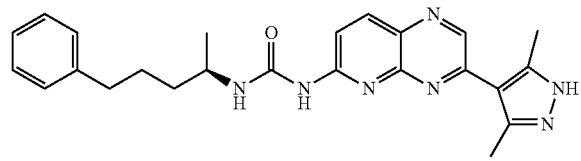 [SMILES: Cc1n[nH]c(C)c1-c1cnc2ccc(NC(=O)N[C@H](C)CCCc3ccccc3)nc2n1]

$^1$H-NMR (DMSO-d$_6$☐☐): ☐=12.70 (s, 1H), 10.02 (s, 1H), 9.42 (s, 1H), 8.92 (s, 1H), 8.28 (d, 1H), 7.53 (d, 1H), 7.17 (m, 4H), 7.12 (m, 1H), 3.87 (m, 1H), 2.61 (m, 2H), 2.54 (s, 3H), 2.48 (s, 3H), 1.70 (m, 2H), 1.55 (m, 2H), 1.19 (d, 3H) ppm mp: 266-269° C.

Compound 178

1-[3-(3,4-Dimethoxy-phenyl)-pyrido[2,3-b]pyrazin-6-yl]-3-(4-phenyl-butyl)-urea

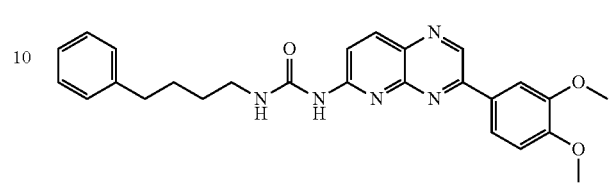

$^1$H-NMR (DMSO-d$_6$☐☐): ☐=10.09 (s, 1H), 9.46 (s, 1H), 9.25 (s, 1H), 8.34 (d, 1H), 7.95 (m, 1H), 7.90 (d, 1H), 7.63 (d, 1H), 7.20 (m, 4H), 7.12 (m, 2H), 3.86 (d, 6H), 3.34 (m, 2H), 2.67 (t, 2H), 1.75 (m, 2H), 1.60 (m, 2H) ppm mp: 210-211° C.

Compound 179

1-[3-(2-Methoxy-phenyl)-pyrido[2,3-b]pyrazin-6-yl]-3-((R)-1-methyl-4-phenyl-butyl)-urea

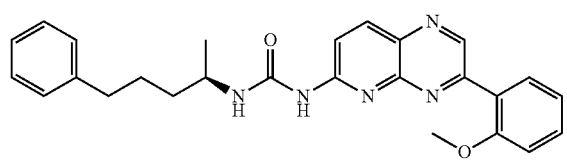 [SMILES: COc1ccccc1-c1cnc2ccc(NC(=O)N[C@H](C)CCCc3ccccc3)nc2n1]

$^1$H-NMR (DMSO-d$_6$☐☐): ☐=10.01 (s, 1H), 9.20 (s, 1H), 9.16 (s, 1H), 8.35 (d, 1H), 7.83 (m, 1H), 7.69 (d, 1H), 7.55 (m, 1H), 7.26 (d, 1H), 7.16 (m, 6H), 3.91 (s, 3H), 3.87 (m, 1H), 2.62 (m, 2H), 1.71 (m, 2H), 1.55 (m, 2H), 1.19 (d, 3H) ppm mp: 137-138° C.

Compound 180

1-((R)-1-Methyl-4-phenyl-butyl)-3-[3-(1-methyl-1H-pyrazol-4-yl)-pyrido[2,3-b]pyrazin-6-yl]-urea

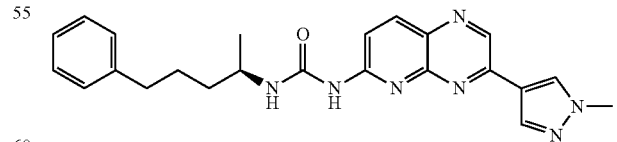

$^1$H-NMR (DMSO-d$_6$☐☐): ☐=9.91 (s, 1H), 9.15 (s, 1H), 9.11 (s, 1H), 8.57 (s, 1H), 8.27 (m, 2H), 7.59 (d, 1H), 7.21 (m, 4H), 7.13 (m, 1H), 3.95 (s, 3H), 3.87 (m, 1H), 2.65 (m, 2H), 1.72 (m, 2H), 1.57 (m, 2H), 1.21 (d, 3H) ppm mp: 225-228° C.

Compound 181

1-[3-(3-Hydroxymethyl-phenyl)-pyrido[2,3-b]pyrazin-6-yl]-3-((R)-1-methyl-4-phenyl-butyl)-urea

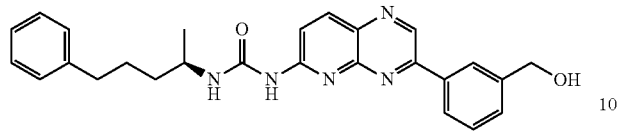

$^1$H-NMR (DMSO-d$_6$): δ=10.02 (s, 1H), 9.43 (s, 1H), 9.18 (s, 1H), 8.36 (d, 1H), 8.29 (s, 1H), 8.20 (d, 1H), 7.70 (d, 1H), 7.55 (m, 2H), 7.19 (d, 4H), 7.11 (m, 1H), 5.34 (s, 1H), 4.63 (s, 2H), 3.87 (m, 1H), 2.66 (m, 2H), 1.75 (m, 2H), 1.58 (m, 2H), 1.21 (d, 3H) ppm mp: 193-195° C.

Compound 182

1-[3-(4-Hydroxymethyl-phenyl)-pyrido[2,3-b]pyrazin-6-yl]-3-(4-phenyl-butyl)-urea

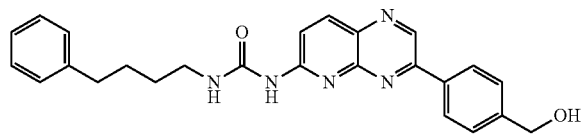 [SMILES: O=C(NCCCCc1ccccc1)Nc1ccc2ncc(-c3ccc(CO)cc3)nc2n1]

$^1$H-NMR (DMSO-d$_6$): δ=10.11 (s, 1H), 9.44 (s, 1H), 9.33 (s, 1H), 8.36 (d, 1H), 8.29 (d, 2H), 7.63 (d, 1H), 7.52 (d, 2H), 7.22 (m, 4H), 7.12 (m, 1H), 5.34 (t, 1H), 4.61 (d, 2H), 3.34 (m, 2H), 2.68 (m, 2H), 1.75 (m, 2H), 1.60 (m, 2H) ppm mp: 213-215° C.

Compound 183

1-[3-(2,4-Dimethoxy-phenyl)-pyrido[2,3-b]pyrazin-6-yl]-3-((R)-1-methyl-4-phenyl-butyl)-urea

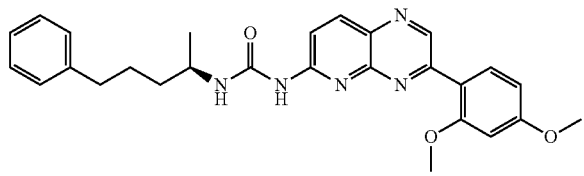 [SMILES: COc1ccc(-c2cnc3ccc(NC(=O)N[C@H](C)CCCc4ccccc4)nc3n2)c(OC)c1]

$^1$H-NMR (DMSO-d$_6$): δ=9.96 (s, 1H), 9.22 (s, 1H), 9.19 (s, 1H), 8.31 (d, 1H), 7.87 (d, 1H), 7.64 (d, 1H), 7.19 (m, 4H), 7.11 (m, 1H), 6.75 (s, 1H), 6.73 (d, 1H), 3.93 (s, 3H) 3.87 (m, 4H), 2.63 (m, 2H), 1.72 (m, 2H), 1.56 (m, 2H), 1.20 (d, 3H) ppm mp: 98-100° C.

Compound 184

1-(4-Phenyl-butyl)-3-(3-pyridin-4-yl-pyrido[2,3-b]pyrazin-6-yl)-urea

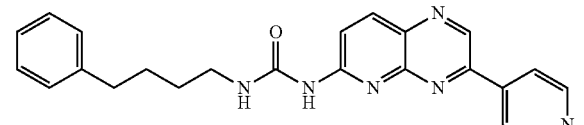

$^1$H-NMR (DMSO-d$_6$): δ=10.21 (s, 1H), 9.54 (s, 1H), 9.26 (s, 1H), 8.80 (d, 2H), 8.41 (d, 1H), 8.24 (d, 2H), 7.73 (d, 1H), 7.21 (m, 4H), 7.13 (m, 1H), 3.35 (m, 2H), 2.68 (t, 2H), 1.75 (m, 2H), 1.60 (m, 2H) ppm mp: 219-222° C.

Compound 185

1-[3-(3-Fluoro-4-hydroxy-phenyl)-pyrido[2,3-b]pyrazin-6-yl]-3-((R)-1-methyl-4-phenyl-butyl)-urea

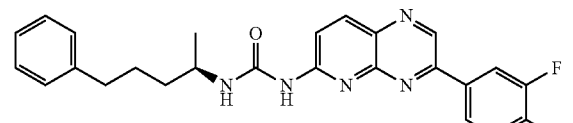

$^1$H-NMR (DMSO-d$_6$): δ=10.58 (s, 1H), 10.00 (s, 1H), 9.40 (s, 1H), 9.23 (s, 1H), 8.32 (d, 1H), 8.15 (d, 1H), 8.05 (d, 1H), 7.62 (d, 1H), 7.18 (m, 6H), 3.87 (m, 1H), 2.66 (m, 2H), 1.75 (m, 2H), 1.58 (m, 2H), 1.21 (d, 3H) ppm mp: 220-222° C.

Compound 186

1-[3-(3-Chloro-4-hydroxy-phenyl)-pyrido[2,3-b]pyrazin-6-yl]-3-(4-phenyl-butyl)-urea

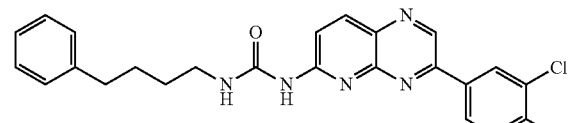

$^1$H-NMR (DMSO-d$_6$): δ=10.96 (s, 1H), 10.08 (s, 1H), 9.40 (s, 1H), 9.35 (s, 1H), 8.35 (m, 2H), 8.16 (m, 1H), 7.59 (d, 1H), 7.22 (m, 4H), 7.13 (m, 2H), 3.34 (m, 2H), 2.69 (t, 2H), 1.76 (m, 2H), 1.59 (m, 2H) ppm mp: 241-243° C.

Compound 187

1-[3-((S)-3-Methyl-morpholin-4-yl)-pyrido[2,3-b]pyrazin-6-yl]-3-((R)-1-methyl-4-phenyl-butyl)-urea

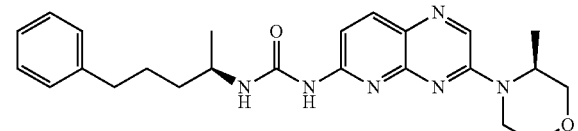

$^1$H-NMR (DMSO-d$_6$): δ=9.72 (s, 1H), 9.20 (s, 1H), 8.59 (s, 1H), 8.02 (m, 1H), 7.21 (m, 6H), 4.61 (m, 1H), 4.21 (m, 1H), 3.94 (m, 1H), 3.82 (m, 1H), 3.74 (m, 1H), 3.48 (m, 1H), 3.25 (m, 1H), 2.62 (m, 2H), 1.71 (m, 2H), 1.52 (m, 2H), 1.24 (m, 3H), 1.17 (m, 3H) ppm

Compound 188

1-[3-(4-{2-[2-(2-Hydroxy-ethoxy)-ethoxy]-ethoxy}-phenyl)-pyrido[2,3-b]pyrazin-6-yl]-3-((R)-1-methyl-4-phenyl-butyl)-urea

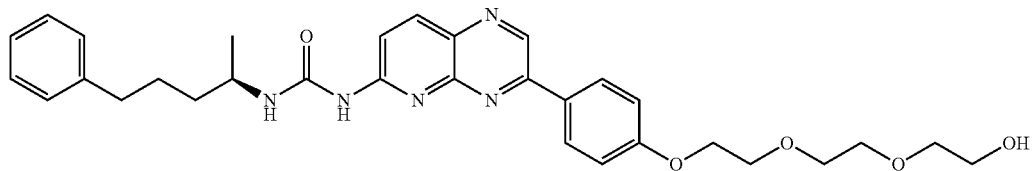 [SMILES: C[C@H](CCCc1ccccc1)NC(=O)Nc1ccc2ncc(-c3ccc(OCCOCCOCCO)cc3)nc2n1]

¹H-NMR (DMSO-d₆): δ=9.99 (s, 1H), 9.41 (s, 1H), 9.23 (s, 1H), 8.31 (m, 3H), 7.62 (m, 1H), 7.17 (m, 7H), 4.22 (m, 2H), 3.79 (m, 1H), 3.62 (m, 2H), 3.56 (m, 2H), 3.44 (m, 2H), 2.66 (m, 2H), 1.75 (m, 2H), 1.59 (m, 2H), 1.22 (m, 3H) ppm

Compound 189

1-{3-[1-(2-Hydroxy-ethyl)-1H-pyrazol-4-yl]-pyrido[2,3-b]pyrazin-6-yl}-3-(4-phenyl-butyl)-urea

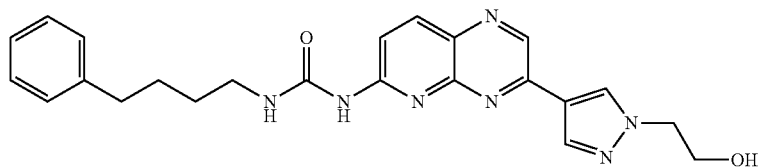 [SMILES: O=C(NCCCCc1ccccc1)Nc1ccc2ncc(-c3cnn(CCO)c3)nc2n1]

¹H-NMR (DMSO-d₆): δ=10.01 (s, 1H), 9.24 (s, 1H), 9.18 (s, 1H), 8.59 (s, 1H), 8.28 (m, 2H), 7.55 (m, 1H), 7.23 (m, 4H), 7.15 (m, 1H), 4.98 (m, 1H), 4.24 (m, 2H), 3.80 (m, 2H), 3.33 (m, 2H), 2.67 (m, 2H), 1.73 (m, 2H), 1.59 (m, 2H) ppm

Compound 194

2-Methoxy-4-{6-[3-(4-phenyl-butyl)-ureido]-pyrido[2,3-b]pyrazin-3-yl}-benzoic acid

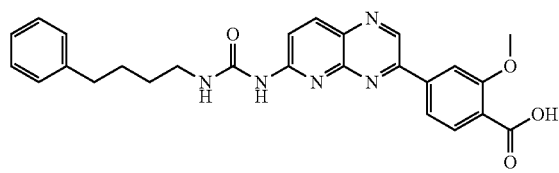 [SMILES: COc1cc(-c2cnc3ccc(NC(=O)NCCCCc4ccccc4)nc3n2)ccc1C(=O)O]

¹H-NMR (DMSO-d₆): δ=12.84 (s, 1H), 10.17 (s, 1H), 9.54 (s, 1H), 9.22 (s, 1H), 8.39 (d, 1H), 7.99 (s, 1H), 7.94 (d, 1H), 7.80 (d, 1H), 7.71 (d, 1H), 7.19 (m, 4H), 7.11 (m, 1H), 3.93 (s, 3H), 3.34 (m, 2H), 2.66 (m, 2H), 1.74 (m, 2H), 1.60 (m, 2H) ppm mp 229-233° C.

Compound 195

(S)-2-Amino-3-(4-{6-[3-((R)-1-methyl-4-phenyl-butyl)-ureido]-pyrido[2,3-b]pyrazin-3-yl}-phenyl)-propionic acid; hydrochloride

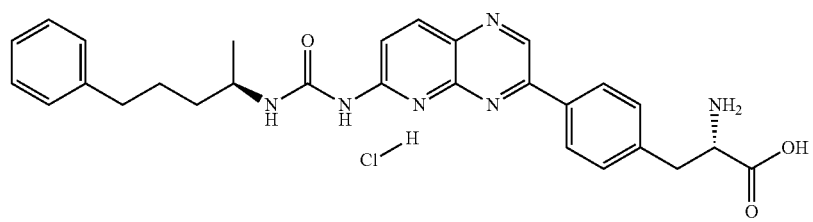

¹H-NMR (DMSO-d₆): δ=13.91 (s, 1H), 10.06 (s, 1H), 9.46 (s, 1H), 9.16 (s, 1H), 8.36 (m, 6H), 7.71 (m, 1H), 7.50 (m, 2H), 7.21 (m, 4H), 7.14 (m, 1H), 4.28 (m, 1H), 3.88 (m, 1H), 3.24 (m, 2H), 2.66 (m, 2H), 1.74 (m, 2H), 1.57 (m, 2H), 1.21 (m, 3H) ppm Compound 196

3-{6-[3-((R)-1-Methyl-4-phenyl-butyl)-ureido]-pyrido[2,3-b]pyrazin-3-yl}-benzoic acid

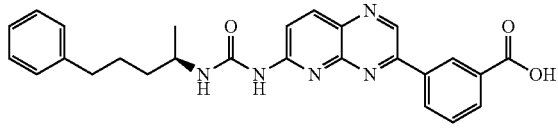 [SMILES: C[C@H](CCCc1ccccc1)NC(=O)Nc1ccc2ncc(-c3cccc(C(=O)O)c3)nc2n1]

¹H-NMR (DMSO-d₆): δ=10.12 (s, 1H), 9.44 (s, 1H), 9.26 (s, 1H), 8.31 (m, 3H), 7.57 (m, 5H), 7.19 (m, 5H), 3.73 (s, 1H), 3.31 (m, 4H), 3.03 (m, 1H), 2.67 (t, 2H), 1.74 (m, 2H), 1.58 (m, 2H) ppm
mp: 230-232° C.

Compound 198

3-{6-[3-(4-Phenyl-butyl)-ureido]-pyrido[2,3-b]pyrazin-3-yl}-benzoic acid

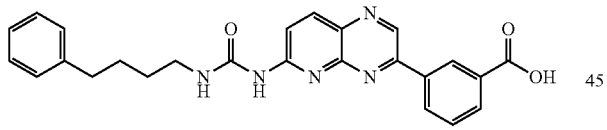

¹H-NMR (DMSO-d₆): δ=13.22 (s, 1H), 10.03 (s, 1H), 9.51 (s, 1H), 9.21 (s, 1H), 8.90 (s, 1H), 8.57 (d, 1H), 8.39 (d, 1H), 8.13 (d, 1H), 7.22 (m, 2H), 7.14 (m, 5H), 3.87 (m, 1H), 2.67 (t, 2H), 1.76 (m, 2H), 1.59 (m, 2H), 1.22 (d, 3H) ppm
mp: 261° C. (dec)

Compound 197

(S)-2-Amino-3-(4-{6-[3-(4-phenyl-butyl)-ureido]-pyrido[2,3-b]pyrazin-3-yl}-phenyl)-propionic acid

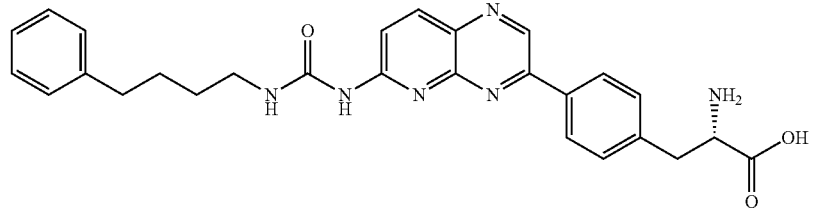 [SMILES: N[C@@H](Cc1ccc(-c2cnc3ccc(NC(=O)NCCCCc4ccccc4)nc3n2)cc1)C(=O)O]

¹H-NMR (DMSO-d₆): δ=13.23 (s, 1H), 10.14 (s, 1H), 9.50 (s, 1H), 9.30 (s, 1H), 8.87 (s, 1H), 8.55 (m, 1H), 8.39 (m, 1H), 8.13 (m, 1H), 7.70 (m, 2H), 7.19 (m, 4H), 7.11 (m, 1H), 3.34 (m, 2H), 2.68 (m, 2H), 1.76 (m, 2H), 1.59 (m, 2H) ppm
mp: 254-256° C.

Compound 200 rac 1-{3-[4-(2-Hydroxy-propoxy)-phenyl]-pyrido[2,3-b]pyrazin-6-yl}-3-(4-phenyl-butyl)-urea

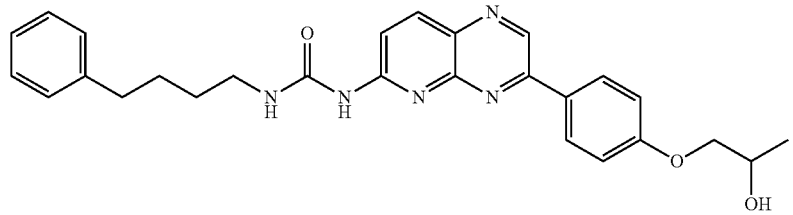 [SMILES: CC(O)COc1ccc(-c2cnc3ccc(NC(=O)NCCCCc4ccccc4)nc3n2)cc1]

¹H-NMR (DMSO-d6) δ=10.82 (s, 1H), 9.41 (s, 1H), 9.32 (s, 1H), 8.32 (d, 1H), 8.29 (d, 2H), 7.59 (d, 1H), 7.22 (m, 4H), 7.11 (m, 3H), 4.90 (s, 1H), 4.00 (m, 1H), 3.91 (m, 2H), 3.31 (m, 2H), 2.68 (t, 2H), 1.75 (m, 2H), 1.59 (m, 2H), 1.18 (d, 3H) ppm
m.p.: 223-224° C.

Compound 201

1-(3-{4-[2-(2-Hydroxy-ethoxy)-ethoxy]-phenyl}-pyrido[2,3-b]pyrazin-6-yl)-3-(4-phenyl-butyl)-urea

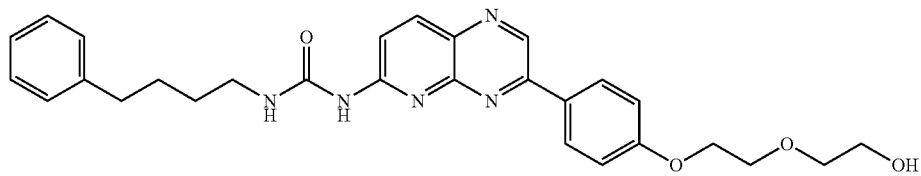 [SMILES: O=C(NCCCCc1ccccc1)Nc1ccc2ncc(-c3ccc(OCCOCCO)cc3)nc2n1]

¹H-NMR (DMSO-d6) δ=10.08 (d, 1H), 9.37 (m, 2H), 8.31 (m, 3H), 7.57 (d, 1H), 7.25 (m, 4H), 7.11 (d, 23H), 4.62 (t, 1H), 4.31 (t, 2H), 3.80 (, t, 2H), 3.52 (m, 4H), 3.34 (m, 2H), 2.68 (t, 2H), 1.75 (m, 2H), 1.60 (m, 2H) ppm
m.p.: 192-194° C.

Compound 202

1-{3-[4-(2-Morpholin-4-yl-ethoxy)-phenyl]-pyrido[2,3-b]pyrazin-6-yl}-3-(4-phenyl-butyl)-urea

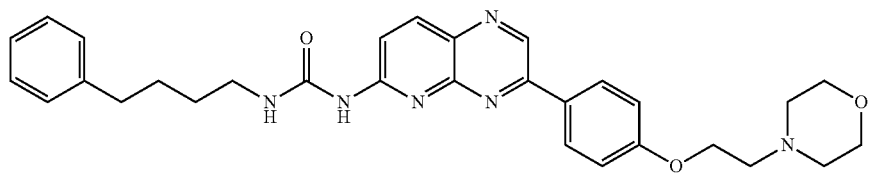 [SMILES: O=C(NCCCCc1ccccc1)Nc1ccc2ncc(-c3ccc(OCCN4CCOCC4)cc3)nc2n1]

¹H-NMR (DMSO-d6) δ=10.08 (s, 1H), 9.41 (s, 1H), 9.35 (s, 1H), 8.31 (d, 1H), 8.29 (d, 2H), 7.59 (d, 1H), 7.22 (m, 4H), 7.12 (d, 3H), 4.22 (m, 2H), 3.68 (s, 4H), 3.32 (m, 2H), 3.29 (s, 4H), 2.78 (m, 2H), 2.68 (m, 2H), 1.73 (m, 2H), 1.59 (m, 2H) ppm
m.p.: 191-192° C.

Compound 203

1-[3-(3-Methoxymethyl-phenyl)-pyrido[2,3-b]pyrazin-6-yl]-3-((R)-1-methyl-4-phenyl-butyl)-urea

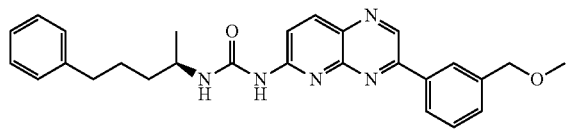 [SMILES: COCc1cccc(-c2cnc3ccc(NC(=O)N[C@H](C)CCCc4ccccc4)nc3n2)c1]

¹H-NMR (DMSO-d6) δ=10.03 (s, 1H), 9.48 (s, 1H), 9.21 (s, 1H), 8.38 (d, 1H), 8.30 (s, 1H), 8.25 (d, 1H), 7.69 (d, 1H), 7.55 (m, 2H), 7.19 (s, 4H), 7.11 (s, 1H), 4.56 (s, 2H), 3.87 (m, 1H), 3.31 (s, 3H), 2.68 (m, 2H), 1.78 (M, 2H), 1.61 (m, 2H), 1.20 (d, 3H) ppm Compound 204: D-119421

1-{3-[3-(2-Methoxy-ethoxymethyl)-phenyl]-pyrido[2,3-b]pyrazin-6-yl}-3-((R)-1-methyl-4-phenyl-butyl)-urea

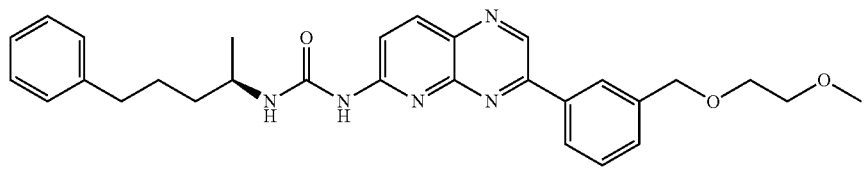 [SMILES: COCCOCc1cccc(-c2cnc3ccc(NC(=O)N[C@H](C)CCCc4ccccc4)nc3n2)c1]

¹H-NMR (DMSO-d6) δ=9.10 (s, 1H), 8.26 (s, 1H), 8.19 (d, 1H); 7.97 (d, 1H), 7.90 (s, 1H), 7.56 (m, 4H), 7.22 (m, 3H), 7.14 (d, 4H), 5.19 (m, 2H), 3.78 (m, 2H), 3.57 (s, 3H), 3.29 (m, 1H), 2.52 (m, 2H), 1.69 (m, 2H), 1.40 (m, 2H), 1.21 (s, 1H), 1.02 (s, 3H) ppm Evidence of the Kinase Inhibition of Compounds According to the Invention Cell-Free Kinase Assays (Using ALPHA Technology)

The inhibitory effect of the compounds according to the invention was tested on various serine/threonine, tyrosine and lipid kinases in enzymatic assays. Recombinant human kinases such as, for example, Erk2, were used in this case, partly as full-length kinases, partly as shortened fragments, but at least consisting of the functional kinase domains. The commercial kinase proteins (Proqinase, Upstate) were used as recombinant fusion proteins with GST (glutathion-S-transferase) or His-Tag. Depending on the type of substrate, the various kinase reactions were quantified by means of suitable ALPHA™ beads (Perkin-Elmer).

Testing

The substance testing is described in detail hereinafter for the Erk assay. Selected test results of the Erk2 alpha assay are given below. To determine the $IC_{50}$ value, the potential inhibitor substances were investigated in 10 semi-logarithmically graded concentrations of 3.16 nM-100 μM.

a) MAPK-ALPHAs (e.g. Erk2): the test substance, 0.625 ng Erk2 (#14-173, Upstate), 10 μM ATP and 15 nM biotinylated MBP (myelin basic protein) substrate were incubated on a 384-well Optiplate (Perkin-Elmer) in a volume of 15 μl for 1 h in 25 mM Tris, 10 mM $MgCl_2$, 0.1% Tween-20, 100 μM $NaVO_4$, 2 mM DTT at pH 7.5. The kinase reaction was then stopped by adding 10 μl of the ALPHA bead mixes (10 μg/ml, #6760617/Perkin-Elmer) pre-incubated with anti-phospho MBP antibody (320 μM, #05-429/Upstate) in 25 mM Tris, 200 mM NaCl, 100 mM EDTA and 0.3% BSA and left to stand overnight.

The fluorescence was detected the following morning in a Envision plate reader (Perkin-Elmer).

Evaluation

The %-inhibition values per substance concentration were calculated by means of the following formula from the raw data determined in the Envision plate reader☐:

% Kinase $inhibition_{(Sample)} =$ $$100 - \left(100 \times \frac{Mean_{(Sample)} - Mean_{(0\% \, Control)}}{Mean_{(100\% \, Control)} - Mean_{(0\% \, Control)}}\right)$$

Eight determinations were made for each control and two for the substance samples. The 0% control either contains no ATP or no substrate, the 100% control (fully active kinase) contains no test substance. The $IC_{50}$ values were determined using GraphPadPrism.

The inventive compounds exhibited effective inhibition of Erk and PI3K $IC_{50}$ values up to 1 nM (see Table 1).

TABLE 1

Erk2 alpha kinase assay test results ($IC_{50}$ [μM] at 10 μM ATP)

| Compound | Erk2 |
|---|---|
| 108 | 0.004 |
| 127 | 0.005 |
| 155 | 0.004 |
| 156 | 0.001 |
| 157 | 0.002 |
| 158 | 0.001 |
| 159 | 0.001 |
| 160 | 0.001 |
| 161 | 0.002 |
| 162 | 0.002 |
| 163 | 0.002 |
| 164 | 0.002 |
| 165 | 0.003 |
| 166 | 0.003 |
| 167 | 0.003 |
| 168 | 0.003 |
| 169 | 0.003 |
| 170 | 0.004 |
| 171 | 0.004 |
| 172 | 0.005 |
| 173 | 0.005 |
| 174 | 0.006 |
| 175 | 0.006 |
| 176 | 0.006 |
| 177 | 0.006 |
| 178 | 0.006 |
| 179 | 0.006 |
| 180 | 0.006 |
| 181 | 0.006 |
| 189 | 0.004 |
| 194 | 0.001 |
| 195 | 0.001 |
| 196 | 0.004 |
| 197 | 0.005 |
| 198 | 0.003 |
| 201 | 0.039 |
| 202 | 0.041 |
| 203 | 0.024 |

Cellular Assay: Testing for Anti-Proliferative Effect (XTT Assay)

The principle of this test is based on the intracellular reduction of the tetrazolium dye XTT (sodium 3'-[1-(phenylaminocarbonyl)-3,4-tetrazolium]-bis(4-methoxy-6-nitro)benzene sulfonic acid, Sigma) to a formazan dye by mitochondrial dehydrogenases. The dye is only formed by metabolically active cells and its photometrically measurable intensity is a quantitative indicator for the presence of living cells. The reduction of dye formation by incubation of the cells with substances serves as a parameter for the anti-proliferative effect.

Testing

The tumour cell lines (ATCC) were injected into 96-well microtitre plates in a defined cell number (1250 cells/well for Hct116) and then incubated overnight in an incubator at 37° C., 5% $CO_2$ and 95% air humidity. The test substances were prepared as stock solutions (10 mM) in DMSO. To determine the $EC_{50}$ values the potential inhibitor substances were added to the cells in half-logarithmically graded dilutions, resulting in final concentrations of 1.58 nM-50 μM. The cell plates were then incubated for ~48 h in an incubator at 37° C., 5% $CO_2$ and 95% air humidity.

For the detection reaction the substrate XTT was mixed with PMS (N-Methyl dibenzopyrazine methylsulfate, Sigma) and added to the cells so that a final concentration of 325 μg XTT/ml and 2.5 μg PMS/ml was obtained. It was then incubated for 3 h at 37° C., 95% air humidity. The formazan salt formed by the cellular dehydrogenases could then be quantified by adsorption at 490 nm.

Evaluation

The % inhibition value was evaluated by means of the following formula from the values for the optical densities measured in each case at 490 nm:

% Inhibition of cell $proliferation_{(Sample)} =$ $$100 - \left(100 \times \frac{Mean_{(Sample)} - Mean_{(0\% \, Control)}}{Mean_{(100\% \, Control)} - Mean_{(0\% \, Control)}}\right)$$

Eight determinations were made for each control and two for the substance samples. The 0% control contains no cells, the 100% control (proliferation control) contains no test substance. The EC$_{50}$ values were determined using GraphPad-Prism.

The compounds according to the invention showed partly effective inhibition of the cell proliferation with EC$_{50}$ values of to <1 μM (see Table 2).

TABLE 2

XTT assay test results (EC$_{50}$ [μM])

| Compound | Hct116 |
| --- | --- |
| 155 | 0.337 |
| 159 | 0.844 |
| 160 | 0.420 |
| 164 | 0.557 |
| 165 | 3.19 |
| 168 | 0.903 |
| 169 | 0.563 |
| 170 | 0.149 |
| 201 | 0.888 |

The invention claimed is:
1. A pyridopyrazine selected from the group consisting of:
1-[3-(4-{2-[2-(2-hydroxy-ethoxy)-ethoxy]-ethoxy}-phenyl)-pyrido[2,3-b]pyrazin-6-yl]-3-(4-phenyl-butyl)-urea;
1-[3-(3,5-dimethyl-1H-pyrazol-4-yl)-pyrido[2,3-b]pyrazin-6-yl]-3-(4-phenyl-butyl)-urea;
1-(4-phenyl-butyl)-3-[3-(2,3,4-trimethoxy-phenyl)-pyrido[2,3-b]pyrazin-6-yl]-urea;
1-[3-(4-methyl-piperazin-1-yl)-pyrido[2,3-b]pyrazin-6-yl]-3-(4-phenyl-butyl)-urea;
1-[3-(3H-benzoimidazol-5-yl)-pyrido[2,3-b]pyrazin-6-yl]-3-(4-phenyl-butyl)-urea;
1-[3-(3-amino-phenyl)-pyrido[2,3-b]pyrazin-6-yl]-3-(4-phenyl-butyl)-urea;
1-(4-phenyl-butyl)-3-(3-piperazin-1-yl-pyrido[2,3-b]pyrazin-6-yl)-urea; hydrochloride;
1-[3-(1-methyl-1H-pyrazol-4-yl)-pyrido[2,3-b]pyrazin-6-yl]-3-(4-p-tolyl-butyl)-urea;
1-[3-(3,4-dimethoxy-phenyl)-pyrido[2,3-b]pyrazin-6-yl]-3-((R)-1-methyl-4-phenyl-butyl)-urea;
1-[4-(4-fluoro-phenyl)-butyl]-3-[3-(1-methyl-1H-pyrazol-4-yl)-pyrido[2,3-b]pyrazin-6-yl]-urea;
1-(4-methyl-4-phenyl-pentyl)-3-[3-(1-propyl-1H-pyrazol-4-yl)-pyrido[2,3-b]pyrazin-6-yl]-urea;
1-[3-(2,4-dimethoxy-phenyl)-pyrido[2,3-b]pyrazin-6-yl]-3-(4-phenyl-butyl)-urea;
1-[3-(2-ethoxy-phenyl)-pyrido[2,3-b]pyrazin-6-yl]-3-(4-phenyl-butyl)-urea;
1-[3-(3,5-dichloro-4-hydroxy-phenyl)-pyrido[2,3-b]pyrazin-6-yl]-3-(4-phenyl-butyl)-urea;
1-[3-(3-hydroxy-phenyl)-pyrido[2,3-b]pyrazin-6-yl]-3-(4-phenyl-butyl)-urea;
1-(4-phenyl-butyl)-3-[3-(2H-pyrazol-3-yl)-pyrido[2,3-b]pyrazin-6-yl]-urea;
1-[3-(4-hydroxy-2-methyl-phenyl)-pyrido[2,3-b]pyrazin-6-yl]-3-(4-phenyl-butyl)-urea;
Acetic acid 4-{6-[3-(4-phenyl-butyl)-ureido]-pyrido[2,3-b]pyrazin-3-yl}-phenyl ester;
1-[3-(1-ethyl-1H-pyrazol-4-yl)-pyrido[2,3-b]pyrazin-6-yl]-3-(4-phenyl-butyl)-urea;
1-[3-(3-bromo-4-hydroxy-phenyl)-pyrido[2,3-b]pyrazin-6-yl]-3-(4-phenyl-butyl)-urea;
1-(4-phenyl-butyl)-3-(3-pyridin-3-yl-pyrido[2,3-b]pyrazin-6-yl)-urea;
1-[3-(1-methyl-1H-pyrazol-4-yl)-pyrido[2,3-b]pyrazin-6-yl]-3-(1,2,3,4-tetrahydro-naphthalen-2-ylmethyl)-urea;
1-[3-(2,3-dimethoxy-phenyl)-pyrido[2,3-b]pyrazin-6-yl]-3-((R)-1-methyl-4-phenyl-butyl)-urea;
1-[3-(5-methyl-1-phenyl-1H-pyrazol-4-yl)-pyrido[2,3-b]pyrazin-6-yl]-3-(4-phenyl-butyl)-urea;
1-[3-(1-butyl-1H-pyrazol-4-yl)-pyrido[2,3-b]pyrazin-6-yl]-3-(4-phenyl-butyl)-urea;
1-[4-(4-methoxy-phenyl)-butyl]-3-[3-(1-methyl-1H-pyrazol-4-yl)-pyrido[2,3-b]pyrazin-6-yl]-urea;
1-(4-phenyl-butyl)-3-[3-(piperidin-4-ylamino)-pyrido[2,3-b]pyrazin-6-yl]-urea;
1-(4-phenyl-butyl)-3-{3-[(pyridin-4-ylmethyl)-amino]-pyrido[2,3-b]pyrazin-6-yl}-urea;
1-[3-(4-methoxy-phenyl)-pyrido[2,3-b]pyrazin-6-yl]-3-(4-phenyl-butyl)-urea;
1-(4-phenyl-butyl)-3-(3-propylamino-pyrido[2,3-b]pyrazin-6-yl)-urea;
1-(4-phenyl-butyl)-3-(3-o-tolyl-pyrido[2,3-b]pyrazin-6-yl)-urea;
3-{6-[3-(4-phenyl-butyl)-ureido]-pyrido[2,3-b]pyrazin-3-yl}-benzoic acid ethyl ester;
Ethyl-carbamic acid 4-{6-[3-(4-phenyl-butyl)-ureido]-pyrido[2,3-b]pyrazin-3-yl}-phenyl ester;
1-[3-(4-amino-3-methoxy-phenyl)-pyrido[2,3-b]pyrazin-6-yl]-3-(4-phenyl-butyl)-urea;
1-[3-(2-methoxy-phenyl)-pyrido[2,3-b]pyrazin-6-yl]-3-(4-phenyl-butyl)-urea;
1-((R)-1-methyl-4-phenyl-butyl)-3-[3-(2,3,4-trimethoxy-phenyl)-pyrido[2,3-b]pyrazin-6-yl]-urea;
1-(1-methyl-4-phenyl-butyl)-3-[3-(1-propyl-1H-pyrazol-4-yl)-pyrido[2,3-b]pyrazin-6-yl]-urea;
1-{3-[1-(2-morpholin-4-yl-ethyl)-1H-pyrazol-4-yl]-pyrido[2,3-b]pyrazin-6-yl}-3-(4-phenyl-butyl)-urea;
1-[3-(2-ethoxy-phenyl)-pyrido[2,3-b]pyrazin-6-yl]-3-((R)-1-methyl-4-phenyl-butyl)-urea;
1-[3-(3-chloro-4-hydroxy-phenyl)-pyrido[2,3-b]pyrazin-6-yl]-3-((R)-1-methyl-4-phenyl-butyl)-urea;
1-[3-(2-amino-phenyl)-pyrido[2,3-b]pyrazin-6-yl]-3-(4-phenyl-butyl)-urea;
1-(4-oxo-4-phenyl-butyl)-3-[3-(1-propyl-1H-pyrazol-4-yl)-pyrido[2,3-b]pyrazin-6-yl]-urea;
Carbonic acid ethyl ester 4-{6-[3-(4-phenyl-butyl)-ureido]-pyrido[2,3-b]pyrazin-3-yl}-phenyl ester;
1-[3-(2-hydroxy-phenyl)-pyrido[2,3-b]pyrazin-6-yl]-3-(4-phenyl-butyl)-urea;
1-[3-(4-hydroxy-cyclohexylamino)-pyrido[2,3-b]pyrazin-6-yl]-3-(4-phenyl-butyl)-urea;
2,2-dimethyl-propionic acid 4-{6-[3-(4-phenyl-butyl)-ureido]-pyrido[2,3-b]pyrazin-3-yl}-phenyl ester;
1-[3-(4-methylsulfanyl-phenyl)-pyrido[2,3-b]pyrazin-6-yl]-3-(4-phenyl-butyl)-urea;
1-[3-(3-cyano-phenyl)-pyrido[2,3-b]pyrazin-6-yl]-3-(4-phenyl-butyl)-urea;
1-(4-phenyl-butyl)-3-[3-(3,4,5-trimethoxy-phenylamino)-pyrido[2,3-b]pyrazin-6-yl]-urea;
1-{3-[(S)-1-(3-chloro-phenyl)-2-hydroxy-ethylamino]-pyrido[2,3-b]pyrazin-6-yl}-3-(4-phenyl-butyl)-urea;
1-[3-(3-hydroxy-4,5-dimethoxy-phenylamino)-pyrido[2,3-b]pyrazin-6-yl]-3-(4-phenyl-butyl)-urea;
1-{3-[1-(3-chloro-phenyl)-2-hydroxy-ethylamino]-pyrido[2,3-b]pyrazin-6-yl}-3-(4-phenyl-butyl)-urea;
1-[3-(4-fluoro-2-hydroxy-phenyl)-pyrido[2,3-b]pyrazin-6-yl]-3-(4-phenyl-butyl)-urea;

1-{3-[4-methoxy-3-(morpholine-4-sulfonyl)-phenyl]-pyrido[2,3-b]pyrazin-6-yl}-3-(4-phenyl-butyl)-urea;
1-[3-(2-methoxy-pyridin-3-yl)-pyrido[2,3-b]pyrazin-6-yl]-3-(4-phenyl-butyl)-urea;
1-[3-(4-hydroxy-phenyl)-pyrido[2,3-b]pyrazin-6-yl]-3-((R)-1-methyl-4-phenyl-butyl)-urea;
1-[3-(3-hydroxy-4-methoxy-phenyl)-pyrido[2,3-b]pyrazin-6-yl]-3-((R)-1-methyl-4-phenyl-butyl)-urea;
1-(3-furan-3-yl-pyrido[2,3-b]pyrazin-6-yl)-3-((R)-1-methyl-4-phenyl-butyl)-urea;
1-((R)-1-methyl-4-phenyl-butyl)-3-(3-pyridin-3-yl-pyrido[2,3-b]pyrazin-6-yl)-urea;
1-[3-(3-hydroxy-4-methoxy-phenyl)-pyrido[2,3-b]pyrazin-6-yl]-3-(4-phenyl-butyl)-urea;
1-(3-furan-3-yl-pyrido[2,3-b]pyrazin-6-yl)-3-(4-phenyl-butyl)-urea;
1-((R)-1-methyl-4-phenyl-butyl)-3-[3-(4-methyl-piperazin-1-yl)-pyrido[2,3-b]pyrazin-6-yl]-urea;
1-((R)-1-methyl-4-phenyl-butyl)-3-(3-piperidin-1-yl-pyrido[2,3-b]pyrazin-6-yl)-urea;
1-[3-(1-methyl-1H-pyrazol-4-yl)-pyrido[2,3-b]pyrazin-6-yl]-3-(4-phenyl-butyl)-urea;
1-[3-(4-hydroxymethyl-2-methoxy-phenyl)-pyrido[2,3-b]pyrazin-6-yl]-3-((R)-1-methyl-4-phenyl-butyl)-urea;
1-((R)-1-methyl-4-phenyl-butyl)-3-(3-pyridin-4-yl-pyrido[2,3-b]pyrazin-6-yl)-urea;
1-[3-(3-hydroxymethyl-2-methoxy-phenyl)-pyrido[2,3-b]pyrazin-6-yl]-3-((R)-1-methyl-4-phenyl-butyl)-urea;
1-(4-phenyl-butyl)-3-[3-(1H-pyrazol-4-yl)-pyrido[2,3-b]pyrazin-6-yl]-urea;
1-[3-(4-hydroxy-phenyl)-pyrido[2,3-b]pyrazin-6-yl]-3-(4-phenyl-butyl)-urea;
1-[3-(2-methoxy-pyridin-3-yl)-pyrido[2,3-b]pyrazin-6-yl]-3-((R)-1-methyl-4-phenyl-butyl)-urea;
1-{3-[1-(3-hydroxy-propyl)-1H-pyrazol-4-yl]-pyrido[2,3-b]pyrazin-6-yl}-3-(4-phenyl-butyl)-urea;
1-{3-[1-(2,2-difluoro-ethyl)-1H-pyrrol-3-yl]-pyrido[2,3-b]pyrazin-6-yl}-3-(4-phenyl-butyl)-urea;
1-(1-methyl-4-phenyl-butyl)-3-[3-(1-methyl-1H-pyrazol-4-yl)-pyrido[2,3-b]pyrazin-6-yl]-urea;
Phosphoric acid mono-(4-{6-[3-(4-phenyl-butyl)-ureido]-pyrido[2,3-b]pyrazin-3-yl}-phenyl)ester;
1-((R)-1-methyl-4-phenyl-butyl)-3-(3-morpholin-4-yl-pyrido[2,3-b]pyrazin-6-yl)-urea;
1-[3-(4-hydroxymethyl-phenyl)-pyrido[2,3-b]pyrazin-6-yl]-3-((R)-1-methyl-4-phenyl-butyl)-urea;
1-((R)-1-methyl-4-phenyl-butyl)-3-{3-[1-(2-morpholin-4-yl-ethyl)-1H-pyrazol-4-yl]-pyrido[2,3-b]pyrazin-6-yl}-urea;
1-(4-methyl-4-phenyl-pentyl)-3-[3-(1-methyl-1H-pyrazol-4-yl)-pyrido[2,3-b]pyrazin-6-yl]-urea;
1-((R)-1-methyl-4-phenyl-butyl)-3-[3-(1-propyl-1H-pyrazol-4-yl)-pyrido[2,3-b]pyrazin-6-yl]-urea;
1-((R)-1-methyl-4-phenyl-butyl)-3-[3-(1H-pyrazol-4-yl)-pyrido[2,3-b]pyrazin-6-yl]-urea;
1-(4-phenyl-butyl)-3-(3-pyrrolidin-1-yl-pyrido[2,3-b]pyrazin-6-yl)-urea;
1-((R)-1-methyl-4-phenyl-butyl)-3-(3-pyrrolidin-1-yl-pyrido[2,3-b]pyrazin-6-yl)-urea;
1-[3-(3-fluoro-4-hydroxy-phenyl)-pyrido[2,3-b]pyrazin-6-yl]-3-(4-phenyl-butyl)-urea;
1-[3-(3-hydroxymethyl-phenyl)-pyrido[2,3-b]pyrazin-6-yl]-3-(4-phenyl-butyl)-urea;
1-(3-morpholin-4-yl-pyrido[2,3-b]pyrazin-6-yl)-3-(4-phenyl-butyl)-urea;
1-[3-(3,5-dimethyl-1H-pyrazol-4-yl)-pyrido[2,3-b]pyrazin-6-yl]-3-((R)-1-methyl-4-phenyl-butyl)-urea;
1-[3-(3,4-dimethoxy-phenyl)-pyrido[2,3-b]pyrazin-6-yl]-3-(4-phenyl-butyl)-urea;
1-[3-(2-methoxy-phenyl)-pyrido[2,3-b]pyrazin-6-yl]-3-((R)-1-methyl-4-phenyl-butyl)-urea;
1-((R)-1-methyl-4-phenyl-butyl)-3-[3-(1-methyl-1H-pyrazol-4-yl)-pyrido[2,3-b]pyrazin-6-yl]-urea;
1-[3-(3-hydroxymethyl-phenyl)-pyrido[2,3-b]pyrazin-6-yl]-3-((R)-1-methyl-4-phenyl-butyl)-urea;
1-[3-(4-hydroxymethyl-phenyl)-pyrido[2,3-b]pyrazin-6-yl]-3-(4-phenyl-butyl)-urea;
1-[3-(2,4-dimethoxy-phenyl)-pyrido[2,3-b]pyrazin-6-yl]-3-((R)-1-methyl-4-phenyl-butyl)-urea;
1-(4-phenyl-butyl)-3-(3-pyridin-4-yl-pyrido[2,3-b]pyrazin-6-yl)-urea;
1-[3-(3-fluoro-4-hydroxy-phenyl)-pyrido[2,3-b]pyrazin-6-yl]-3-((R)-1-methyl-4-phenyl-butyl)-urea;
1-[3-(3-chloro-4-hydroxy-phenyl)-pyrido[2,3-b]pyrazin-6-yl]-3-(4-phenyl-butyl)-urea;
1-[3-((S)-3-methyl-morpholin-4-yl)-pyrido[2,3-b]pyrazin-6-yl]-3-((R)-1-methyl-4-phenyl-butyl)-urea;
1-[3-(4-{2-[2-(2-Hydroxy-ethoxy)-ethoxy]-ethoxy}-phenyl)-pyrido[2,3-b]pyrazin-6-yl]-3-((R)-1-methyl-4-phenyl-butyl)-urea;
1-{3-[1-(2-hydroxy-ethyl)-1H-pyrazol-4-yl]-pyrido[2,3-b]pyrazin-6-yl}-3-(4-phenyl-butyl)-urea;
2-methoxy-4-{6-[3-(4-phenyl-butyl)-ureido]-pyrido[2,3-b]pyrazin-3-yl}-benzoic acid;
(S)-2-amino-3-(4-{6-[3-((R)-1-methyl-4-phenyl-butyl)-ureido]-pyrido[2,3-b]pyrazin-3-yl}-phenyl)-propionic acid; hydrochloride;
3-{6-[3-((R)-1-methyl-4-phenyl-butyl)-ureido]-pyrido[2,3-b]pyrazin-3-yl}-benzoic acid;
(S)-2-amino-3-(4-{6-[3-(4-phenyl-butyl)-ureido]-pyrido[2,3-b]pyrazin-3-yl}-phenyl)-propionic acid;
3-{6-[3-(4-phenyl-butyl)-ureido]-pyrido[2,3-b]pyrazin-3-yl}-benzoic acid;
1-{3-[4-(2-methoxy-ethoxy)-phenyl]-pyrido[2,3-b]pyrazin-6-yl}-3-(4-phenyl-butyl)-urea;
rac 1-{3-[4-(2-hydroxy-propoxy)-phenyl]-pyrido[2,3-b]pyrazin-6-yl}-3-(4-phenyl-butyl)-urea;
1-(3-{4-[2-(2-hydroxy-ethoxy)-ethoxy]-phenyl}-pyrido[2,3-b]pyrazin-6-yl)-3-(4-phenyl-butyl)-urea;
1-{3-[4-(2-morpholin-4-yl-ethoxy)-phenyl]-pyrido[2,3-b]pyrazin-6-yl}-3-(4-phenyl-butyl)-urea;
1-[3-(3-methoxymethyl-phenyl)-pyrido[2,3-b]pyrazin-6-yl]-3-((R)-1-methyl-4-phenyl-butyl)-urea;
1-{3-[3-(2-methoxy-ethoxymethyl)-phenyl]-pyrido[2,3-b]pyrazin-6-yl}-3-((R)-1-methyl-4-phenyl-butyl)-urea;
1-{3-[3-(2-dimethylamino-ethoxymethyl)-phenyl]-pyrido[2,3-b]pyrazin-6-yl}-3-((R)-1-methyl-4-phenyl-butyl)-urea;
Methanesulfonic acid 3-{6-[3-((R)-1-methyl-4-phenyl-butyl)-ureido]-pyrido[2,3-b]pyrazin-3yl}-benzyl ester;
1-((R)-1-methyl-4-phenyl-butyl)-3-{3-[3-(2-morpholin-4yl-ethoxymethyl)phenyl]pyrido[2,3-b]pyrazin-6-yl}-urea;
Ethyl-carbamic acid 3-{6-[3-((R)-1-methyl-4-phenyl-butyl)-ureido]-pyrido[2,3-b]pyrazin-3-yl}-benzyl ester; and
1-((R)-1-methyl-4-phenyl-butyl)-3-{3-[3-((2R,3R,4S,5S,6R)-3,4,5-trihydroxy-6-hydroxymethyl-tetrahydro-pyran-2-yloxymethyl)-phenyl]-pyrido[2,3-b]pyrazin-6-yl}-urea;
or a pharmaceutically acceptable salt, stereoisomer, or tautomer thereof.

2. The pyridopyrazine according to claim 1 which is selected from the group consisting of:

1-[3-(4-{2-[2-(2-hydroxy-ethoxy)-ethoxy]-ethoxy}-phenyl)-pyrido[2,3-b]pyrazin-6-yl]-3-(4-phenyl-butyl)-urea;

1-{3-[1-(2-morpholin-4-yl-ethyl)-1H-pyrazol-4-yl]-pyrido[2,3-b]pyrazin-6-yl}-3-(4-phenyl-butyl)-urea;

1-[3-(1-methyl-1H-pyrazol-4-yl)-pyrido[2,3-b]pyrazin-6-yl]-3-(4-phenyl-butyl)-urea;

1-((R)-1-methyl-4-phenyl-butyl)-3-{3-[1-(2-morpholin-4-yl-ethyl)-1H-pyrazol-4-yl]-pyrido[2,3-b]pyrazin-6-yl}-urea; and 1-((R)-1-methyl-4-phenyl-butyl)-3-[3-(1-propyl-1H-pyrazol-4-yl)-pyrido[2,3-b]pyrazin-6-yl]-urea;

or a pharmaceutically acceptable salt, stereoisomer, or tautomer thereof.

3. A pharmaceutical composition which comprises a pharmaceutically active amount of at least one compound according to claim 2, and a pharmaceutically acceptable carrier.

4. A pharmaceutical composition which comprises a pharmaceutically active amount of at least one compound according to claim 1, and a pharmaceutically acceptable carrier.

5. The pharmaceutical composition according to claim 4, wherein the at least one compound is present in a unit dose of 0.001 mg to 100 mg per kg body weight of a patient.

6. The pharmaceutical composition according to claim 4, which comprises a pharmaceutically active amount of 1-[3-(4-{2-[2-(2-hydroxy-ethoxy)-ethoxy]-ethoxy}-phenyl)-pyrido[2,3-b]pyrazin-6-yl]-3-(4-phenyl-butyl)-urea.

7. The pharmaceutical composition according to claim 4, which comprises a pharmaceutically active amount of 1-{3-[1-(2-morpholin-4-yl-ethyl)-1H-pyrazol-4-yl]-pyrido[2,3-b]pyrazin-6-yl}-3-(4-phenyl-butyl)-urea.

8. The pharmaceutical composition according to claim 4, which comprises a pharmaceutically active amount of 1-[3-(1-methyl-1H-pyrazol-4-yl)-pyrido[2,3-b]pyrazin-6-yl]-3-(4-phenyl-butyl)-urea.

9. The pharmaceutical composition according to claim 4, which comprises a pharmaceutically active amount of 1-((R)-1-methyl-4-phenyl-butyl)-3-{3-[1-(2-morpholin-4-yl-ethyl)-1H-pyrazol-4-yl]-pyrido[2,3-b]pyrazin-6-yl}-urea.

10. The pharmaceutical composition according to claim 4, which comprises a pharmaceutically active amount of 1-((R)-1-methyl-4-phenyl-butyl)-3-[3-(1-propyl-1H-pyrazol-4-yl)-pyrido[2,3-b]pyrazin-6-yl]urea.

* * * * *